United States Patent
Alabugin et al.

(10) Patent No.: US 9,676,679 B2
(45) Date of Patent: Jun. 13, 2017

(54) TRACELESS DIRECTING GROUPS IN RADICAL CASCADES: FROM OLIGOALKYNES TO FUSED HELICENES WITHOUT TETHERED INITATORS

(71) Applicant: The Florida State University Research Foundation, Inc., Tallahassee, FL (US)

(72) Inventors: Igor V. Alabugin, Tallahassee, FL (US); Kamalkishore Pati, Tallahassee, FL (US)

(73) Assignee: The Florida State University Research Foundation, Inc., Tallahassee, FL (US)

( * ) Notice: Subject to any disclaimer, the term of this patent is extended or adjusted under 35 U.S.C. 154(b) by 0 days.

(21) Appl. No.: 14/930,860

(22) Filed: Nov. 3, 2015

(65) Prior Publication Data
US 2016/0145276 A1    May 26, 2016

Related U.S. Application Data

(60) Provisional application No. 62/083,520, filed on Nov. 24, 2014.

(51) Int. Cl.
C07F 7/22 (2006.01)
C07C 1/32 (2006.01)
(Continued)

(52) U.S. Cl.
CPC .............. *C07C 1/325* (2013.01); *C07C 17/26* (2013.01); *C07C 41/18* (2013.01); *C07C 45/67* (2013.01);
(Continued)

(58) Field of Classification Search
CPC ....... C07F 7/2212; C07C 1/325; C07C 41/18; C07C 45/67; C07C 253/30; C07C 17/26; C07D 221/18; C07D 317/70
(Continued)

(56) References Cited

U.S. PATENT DOCUMENTS

| 8,410,303 B2 | 4/2013 | Alabugin et al. |
| 8,927,728 B2 | 1/2015 | Alabugin et al. |

(Continued)

FOREIGN PATENT DOCUMENTS

WO    2012037062 A3    3/2012

OTHER PUBLICATIONS

Mallory, Frank B. et al., Phenacenes: a family of graphite ribbons. Part 3: Iterative strategies for the synthesis of large phenacenes, Tetrahedron, 57, © 2001 Elsevier Science Ltd., (2001) pp. 3715-3724.

(Continued)

*Primary Examiner* — Porfirio Nazario Gonzalez
(74) *Attorney, Agent, or Firm* — Armstrong Teasdale LLP

(57) ABSTRACT

The present disclosure is directed to a traceless directing group in a radical cascade. The chemo- and regioselectivity of the initial attack in skipped oligoalkynes is controlled by a propargyl alkoxy moiety. Radical translocations lead to the boomerang return of radical center to the site of initial attack where it assists to the elimination of the directing functionality via β-scission in the last step of the cascade. In some aspects, the reaction of the present invention is catalyzed by a stannane moiety, which allows further via facile reactions with electrophiles as well as Stille and Suzuki cross-coupling reactions. This selective radical transformation opens a new approach for the controlled transformation of skipped oligoalkynes into polycyclic ribbons of tunable dimensions.

44 Claims, 21 Drawing Sheets

(51) Int. Cl.
    C07D 221/18    (2006.01)
    C07D 317/70    (2006.01)
    C07C 41/18     (2006.01)
    C07C 45/67     (2006.01)
    C07C 253/30    (2006.01)
    C07C 17/26     (2006.01)
(52) U.S. Cl.
    CPC .......... C07C 253/30 (2013.01); C07D 221/18
        (2013.01); C07D 317/70 (2013.01); C07C
        2103/40 (2013.01); C07C 2103/54 (2013.01)
(58) Field of Classification Search
    USPC ........................................................ 556/95
    See application file for complete search history.

(56)                References Cited

U.S. PATENT DOCUMENTS 8,927,778 B2    1/2015   Alabugin et al.
    9,206,100 B2   12/2015   Alabugin et al.
    9,273,023 B2    3/2016   Alabugin et al.
    2013/0196985 A1 8/2013   Ding et al.

OTHER PUBLICATIONS

Wu, Jishan et al., Graphenes as Potential Material for Electronics, Chemical Reviews, vol. 107, No. 3, © 2007 American Chemical Society, (2007), pp. 718-747.
Berresheim, Alexander J. et al., Polyphenylene Nanostructures, Chemical Reviews, vol. 99, No. 7, © 1999 American Chemical Society, (1999), pp. 1747-1785.
Geim, A.K. et al., The Rise of Graphene, Nature Materials, vol. 6, © 2007 Nature Publishing Group, (Mar. 2007), pp. 183-191.
Kuninobu, Yoichiro et al., Synthesis of Functionalized Pentacenes from Isobenzofurans Derived from C—H Bond Activation, Organic Letters, vol. 12, No. 22, © 2010 American Chemical Society, (Oct. 20, 2010), pp. 5287-5289.
Scherf, Ullrich, Ladder-type materials, J. Mater. Chem., vol. 9, 1999, pp. 1853-1864.
Allen, Matthew J. et al., Honeycomb Carbon: A Review of Graphene, Chemical Reviews, vol. 110, No. 1, © 2010 American Chemical Society, (Jul. 17, 2009), pp. 132-145.
Goldfinger, Marc B. et al., Fused Polycyclic Aromatics via Electrophile-Induced Cyclization Reactions: Application to the Synthesis of Graphite Ribbons, J. Am. Chem. Soc., vol. 116, No. 17, © 1994 American Chemical Society, (1994), pp. 7895-7896.
Swartz, Christopher R. et al., Synthesis and Characterization of Electron-Deficient Pentacenes, Organic Letters, vol. 7, No. 15, © 2005 American Chemical Society, (Jun. 30, 2005), pp. 3163-3166.
Li, Xiaolin et al., Chemically Derived, Ultrasmooth Graphene Nanoribbon Semiconductors, Science, vol. 319, © 2008 by the American Association for the Advancement of Science, (Feb. 29, 2008), pp. 1229-1232.
Paquette, Lee et al., The Square Ester—Polyquinane Connection. An Analysis of the Capacity of Achiral Divinyl Adducts to Rearrange Spontaneously to Polycyclic Networks Housing Multiple Sterogenic Centers, J. American Chemical Society, 1997, vol. 119, pp. 1230-1241.
Pollart, Daniel J. et al., Generation of (Trimethylsiloxy)(phenylethynyl)ketene and (Trimethylsiloxy)cyanoketene and Their Reactions with Some Alkynes, Journal of Org. Chemical, 1989, vol. 54, pp. 5444-5448.

Arns, Steve et al., Cascading pericyclic reactions: building complex carbon frameworks for natural product synthesis, Chem. Commun., 2007, pp. 2211-2221, The Royal Society of Chemistry.
Baldwin, Jack E. et al., Rules for Ring Closure: Application to Intramolecular Aldol Condensations in Polyketonic Substrates, Tetrahedron, 1982, pp. 2939-2947, vol. 38, No. 19, Great Britain.
Butenschon, Holger, Arene chromium complexes with functionalized anellated rings. Selective formation of highly substituted polycycles, Pure Appl. Chem., 2002, pp. 57-62; vol. 74, No. 1, IUPAC.
Carpenter, Barry K., A Simple Model for Predicting the Effect of Substituents on the Rates of Thermal Pericyclic Reactions, Tetrahedron, 1978, pp. 1877-1884, vol. 34, Pergamon Press Ltd.
Dahnke, Karl R. et al., Exploratory Synthetic Studies Involving the Tricyclo[9.3.0.0^2,8]tetradecane Ring System Peculiar to the Cyathins, J. Org. Chem., 1994, pp. 885-899, vol. 59, American Chemical Society.
Gentric, Lionel et al., Rate Acceleration of Anionic Oxy-Cope Rearrangements Induced by an Additional Unsaturation, Organic Letters, 2003, pp. 3631-3634, vol. 5, No. 20, American Chemical Society.
Graulich, Nicole et al., Heuristic thinking makes a chemist smart, Chemical Society Reviews, 2010, pp. 1503-1512, vol. 39, The Royal Society of Chemistry.
Huntsman, William D. et al., The Thermal Rearrangement of 1,5-Hexadiyne and Related Compounds, J. Org. Chem., Jan. 18, 1967, pp. 342-347, vol. 89, No. 2, Journal of the American Chemical Society.
Evans, D.A. et al., [3,3] Sigmatropic Rearrangements of 1,5-Diene Alkoxides. The Powerful Accelerating Effects of the Alkoxide Substituent, Journal of the American Chemical Society, Aug. 6, 1975, pp. 4765-4766, vol. 97, No. 16, American Chemical Society.
Evans, D.A. et al., A General Approach to the Synthesis of 1,6 Dicarbonyl Substrates. New Applications of Base-Accelerated Oxy-Cope Rearrangements, Journal of the American Chemical Society, Mar. 29, 1978, pp. 2242-2244, vol. 100, No. 7, American Chemical Society.
Jacobi, Peter A. et al., Bis Heteroannulation. 7. Total Syntheses of (+)-Chididione and (+)-Isognididione, J. Am. Chem. Soc., 1987, pp. 3041-3043, vol. 106, Amerian Chemical Society.
Paquette, Leo A., Recent Applications of Anionic Oxy-Cope Rearrangements, Tetrahedron Report No. 429, 1997, pp. 13971-14020, vol. 52, No. 41, Elsevier Science Ltd, Great Britian.
Roth, Wolfgang R. et al., A "Frustrated" Cope Rearrangement: Thermal Interconversion of 2,6-Diphenylhepta-1,6-diene and 1,5-Diphenylbicyclo[3.2.0]heptain, Journal of the American Chemical Society, 1990, pp. 1722-1732, vol. 112, American Chemical Society.
Pal, Runa et al., Fast Oxy-Cope Rearrangements of Bis-alkynes: Competition with Central C—C Bond Fragmentation and Incorporation in Tunable Cascades Diverging from a Common Bis-allenic Intermediate, JOC Note, 2010, pp. 8689-8692, vol. 75, J. Org. Chem.
Zimmerman, Howard E., Kinetic Protonation of Enols, Enolates, and Analogues. The Stereochemistry of Ketonization, Acc. Chem. Res., 1987, pp. 263-268, vol. 20, American Chemical Society.
Zimmerman, Howard E. et al, the Stereochemistry of Allenic Enol Tautomerism—Independent Generation and Reactivity of he Enolates, Eur. J. Org. Chem., 2006, pp. 3491-3497, Wiley-VCH Verlag GmbH & Co.
Pati, Kamalkishore, et al., Exo-Dig Radical Cascades of Skipped Enediynes: Building a Naphthalene Moiety within a Polycyclic Framework, Chemistry, A European Journal, 2014, vol. 20, pp. 390-393.

TRACELESS DIRECTING GROUPS IN RADICAL CASCADES: FROM OLIGOALKYNES TO FUSED HELICENES WITHOUT TETHERED INITATORS

CROSS REFERENCE TO RELATED APPLICATION(S)

This application claims the benefit of U.S. Provisional Application Ser. No. 62/083,520, filed Nov. 24, 2014 and titled TRACELESS DIRECTING GROUPS IN RADICAL CASCADES: FROM OLIGOALKYNES TO FUSED HELICENES WITHOUT TETHERED INITIATORS. The priority provisional application is incorporated by reference herein as if set forth in its entirety.

STATEMENT REGARDING FEDERALLY SPONSORED RESEARCH OR DEVELOPMENT

This invention was made with Government support under Grants CHE-1152491 and CHE-1213578 awarded by the National Science Foundation. The Government has certain rights in the invention.

FIELD OF THE INVENTION

The present invention relates to a method of preparing a polycyclic aromatic compound, such as a substituted benzo[a]fluorene, substituted heteroaromatic analogues, and larger polycyclic aromatic structures.

BACKGROUND OF THE INVENTION

Chemists have a love/hate relationship with protecting and directing groups. See Young, I. S. Baran, P. S. *Nature Chemistry*, 2009, 1, 193. Although such groups are very often needed to achieve the desired chemo- and regioselectivity of the key chemical transformation in the presence of multiple targets, but like lingering guests, they remain long after they have overstayed their welcome. However, use of such groups is often unavoidable for achieving sufficient selectivity in cascade transformations of multifunctional reactants.

The problem of selectivity comes to the fore in cascades aimed at the preparation of polyaromatic ribbons from conjugated and skipped oligoalkynes. See a) Intermolecular initiation: Alabugin, I. V.; Gilmore, K.; Patil, S.; Manoharan, M.; Kovalenko, S. V.; Clark, R. J.; Ghiviriga, I. *J. Am. Chem. Soc.* 2008, 130, 11535; b) Intramolecular initiation: Byers, P. M.; Alabugin, I. V. *J. Am. Chem. Soc.* 2012, 134, 9609; and further see Pati, K.; Hughes, A. M.; Phan, H.; Alabugin, I. V. *Chem. Eur. J.* 2014, 20, 390. These processes correspond to controlled "polymerization" of alkyne moieties positioned between the two rows of aromatic rings via a selective sequence of "all-exo" cyclizations. See "All endo-dig" cascades require a different activation mode: Byers, P. M.; Rashid, J. I.; Mohamed, R. K.; Alabugin, I. V. *Org. Lett.* 2012, 14, 6032. Although the regioselectivity of cyclizations is well controlled by the exo-preference for alkyne cyclizations, the key remaining challenge in the design of these cascades involves achieving control over chemoselectivity of initial radical attack. See General discussion of exo-selectivity in radical reactions: a) Beckwith, A. L. J. *Tetrahedron* 1981, 37, 3073; b) Beckwith, A. L. J.; Schiesser, C. H. *Tetrahedron* 1985, 41, 3925; General discussion of selectivity of alkyne cyclizations: c) Gilmore, K.; Alabugin, I. V. *Chem. Rev.* 2011, 111, 6513; d) Alabugin, I. V.; Gilmore, K.; Manoharan, M. *J. Am. Chem. Soc.* 2011, 133, 12608; e) 5-Exo/6-endo competition in conjugated systems: Alabugin, I. V.; Manoharan, M. *J. Am. Chem. Soc.* 2005, 127, 12583. The secondary challenge lies in avoiding the formation of pentagonal units at initiation and termination points of the oligoalkyne cascade. We discuss these challenges below.

For the "polymerization cascade" to proceed to completion by utilizing each of the triple bonds, the initial radical attack should proceed exclusively at the central alkyne of the oligoalkyne precursor. See FIG. 1, which is an illustration of the connection between benzannelated oligoalkynes and graphene ribbons. See Beckwith, A. L. J. *Tetrahedron* 1981, 37, 3073. Such chemoselectivity is difficult to achieve because of the close similarity in the electronic and steric properties of the multiple alkyne units. Initially, we addressed this challenge via covalent attachment of a tethered initiator ("the weak link") which is directed at the correct alkyne target by geometric restraints imposed by the intramolecular trajectory. See Beckwith, A. L. J.; Schiesser, C. H. *Tetrahedron* 1985, 41, 3925. Although this approach solves the problem of chemoselectivity of activation, the solution is not ideal because atoms of the tether remain in the molecule after the cascade.

Furthermore, when conjugated oligoalkynes are used as reactants, ring formation from the first two alkyne moieties of benzannelated oligoalkynes, has to proceed via a 5-exo-dig path. See FIG. 2, which illustrates the evolution of molecular design for the conversion of oligoalkynes into polyaromatic ribbons. FIG. 2 includes a depiction of earlier work ("Earlier Work"), and further includes a depiction of the process according to the present invention ("Present Work"). As a consequence, the "polyacetylene ribbon" formed from the oligoalkyne always contained a pentagonal unit.

SUMMARY OF THE INVENTION

According to the method of the present invention and with an exemplary, non-limiting embodiment depicted in FIG. 2 under "Present Work," we have shown that the presence of this pentagon can be avoided when the first reaction between the two alkynes are engineered to follow a 6-exo path, when the starting oligoalkynes are changed from conjugated to "skipped" by adding one extra carbon.

The present invention is therefore directed to a method of preparing a polycyclic aromatic compound. The method comprises contacting a compound having structure (I) with a stannane compound in the presence of a radical initiator to thereby prepare the polycyclic aromatic compound. The polycyclic aromatic compound has a structure (1-a) as follows:

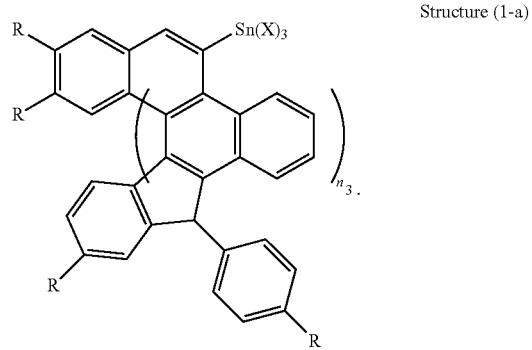

Structure (1-a)

The compound having structure (I) is as follows:

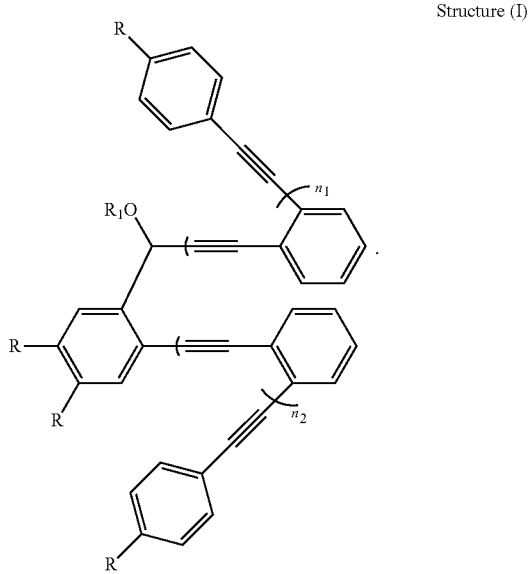

Structure (I)

Other objects and features will be in part apparent and in part pointed out hereinafter.

BRIEF DESCRIPTION OF THE DRAWINGS

FIG. 3 illustrates translocation of a radical coupled with loss of X.

FIG. 5 is the ORTEP diagram for 2a.

DESCRIPTION OF THE EMBODIMENT(S) OF THE INVENTION

One aspect of the invention is a strategy for chemoselective reactions of oligoalkynes that does not rely on the weak link for radical initiation. Instead, it achieves selective intermolecular attack by using a propargylic alkoxy, e.g., a methoxy, group at the skipped alkynes for directing tin radical at the correct position where it initiates the full cascade. The use of 0-directing functionalities in Sn-radical attack at alkynes has been documented with many interesting examples in the recent work of Hale and Organ. See a) Konoike, T.; Araki, Y. *Tetrahedron Lett*. 1992, 33, 5093; b) Nativi, C.; Taddei, M. *J. Org. Chem*. 1988, 53, 820; c)

Ensley, H. E.; Buescher, R. R.; Lee, K. *J. Org. Chem.* 1982, 47, 404; d) Benechie, M.; Skrydstrup, T.; Khuong-Huu, F. *Tetrahedron Lett.* 1991, 32, 7535; e) Addi, K.; Skrydstrup, T.; Benechie, M.; Khuong-Huu, F. *Tetrahedron Lett.* 1993, 34, 6407; f) Lautens, M.; Huboux, A. H. *Tetrahedron Lett.* 1990, 31, 3105; g) Betzer, J. F.; Delaloge, F.; Muller, B.; Pancrazi, A.; Prunet, J. *J. Org. Chem.* 1997, 62, 7768; h) Willem, R.; Delmotte, A.; De Borger, I.; Biesemans, M.; Gielen, M.; Kayser, F. *J. Organomet. Chem.* 1994, 480, 255; i) Creative applications in total synthesis: Hale, K. J.; Grabski, M.; Manaviazar, S.; Maczka, M. Org. Lett., 2014, 16, 1164; j) Micoine, K.; Persich, P.; Llaveria, J.; Lam, M. H.; Maderna, A.; Loganzo, F.; Fürstner, A. *Chem. Eur. J.* 2013, 19, 7370. See a) Dimopoulos, P.; Athlan, A.; George, J.; Manaviazar, S.; Walters, M.; Lazarides, L.; Aliev, A. E.; Hale, K. J. *Org. Lett.* 2005, 7, 5369; b) Dimopoulos, P.; Athlan, A.; Manaviazar, S.; Hale, K. J. *Org. Lett.* 2005, 7, 5373; c) Dimopoulos, P.; George, J.; Tocher, D. A.; Manaviazar, S.; Hale, K. J. *Org. Lett.* 2005, 7, 5377; d) Manaviazar, S.; Hale, K. J.; LeFranc, A. *Tetrahedron Lett.* 2011, 52, 2080. The Organ group offered an interesting mechanistic explanation of this selectivity based on the transient formation of Sn-Cations in a $O_2$-mediated catalytic cycle: a) Oderinde, M. S.; Hunter, H. N.; Organ, M. G. *Chem. Eur. J.* 2012, 18, 10817; b) Oderinde, M. S.; Hunter, H. N.; Froese, R. D. J.; Organ, M. G. *Chem. Eur. J.* 2012, 18, 10821; c) Oderinde, M. S.; Organ, M. G. *Angew. Chem. Int. Ed.* 2012, 51, 9834; d) Oderinde, M. S.; Organ, M. G. *Chem. Eur. J.* 2013, 19, 2615; e) Oderinde, M. S.; Froese, R. D. J.; Organ, M. G. *Angew. Chem. Int. Ed.* 2013, 52, 11334; f) Oderinde, M. S.; Froese, R. D. J.; Organ, M. G. *Chem. Eur. J.* 2014, 20, 8579.

Figure 1:
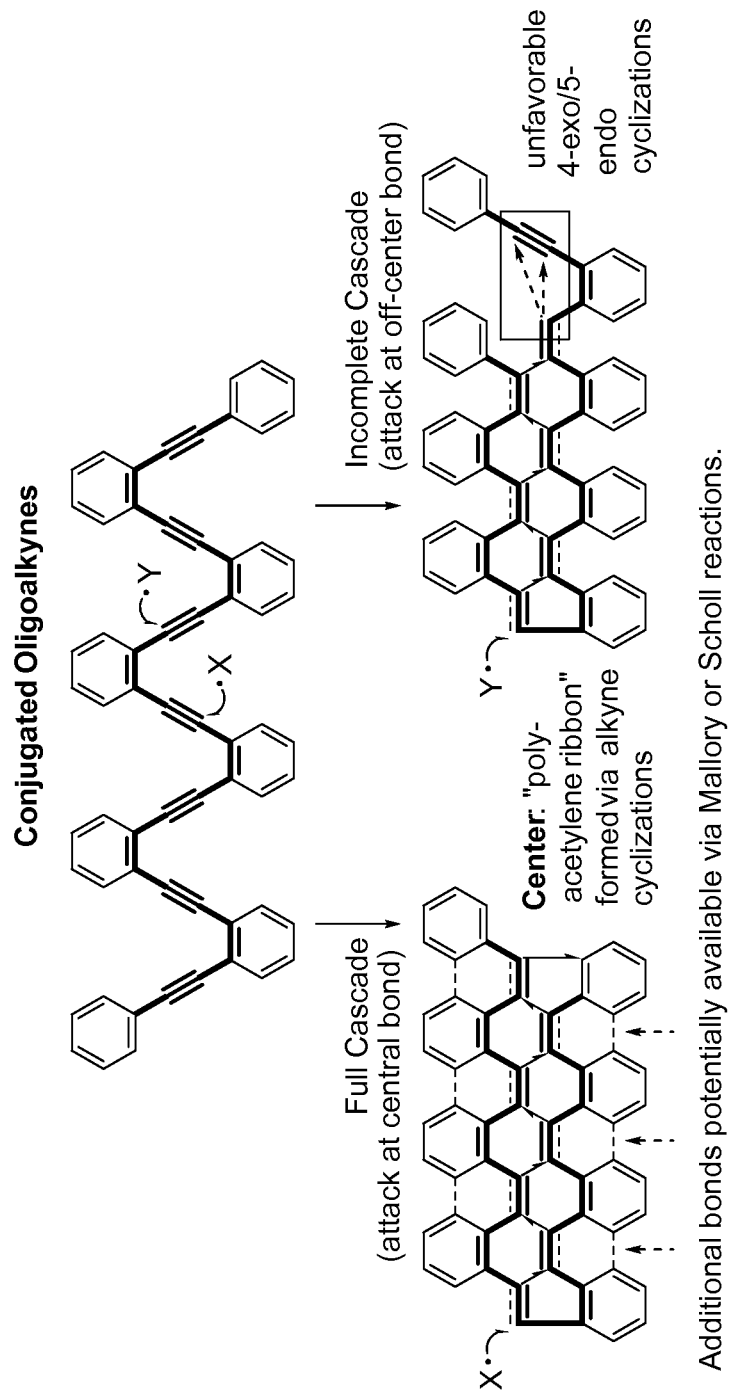
FIG. 1 is a drawing illustrating the connection between benzannelated oligoalkynes and graphene ribbons.
Figure 2:
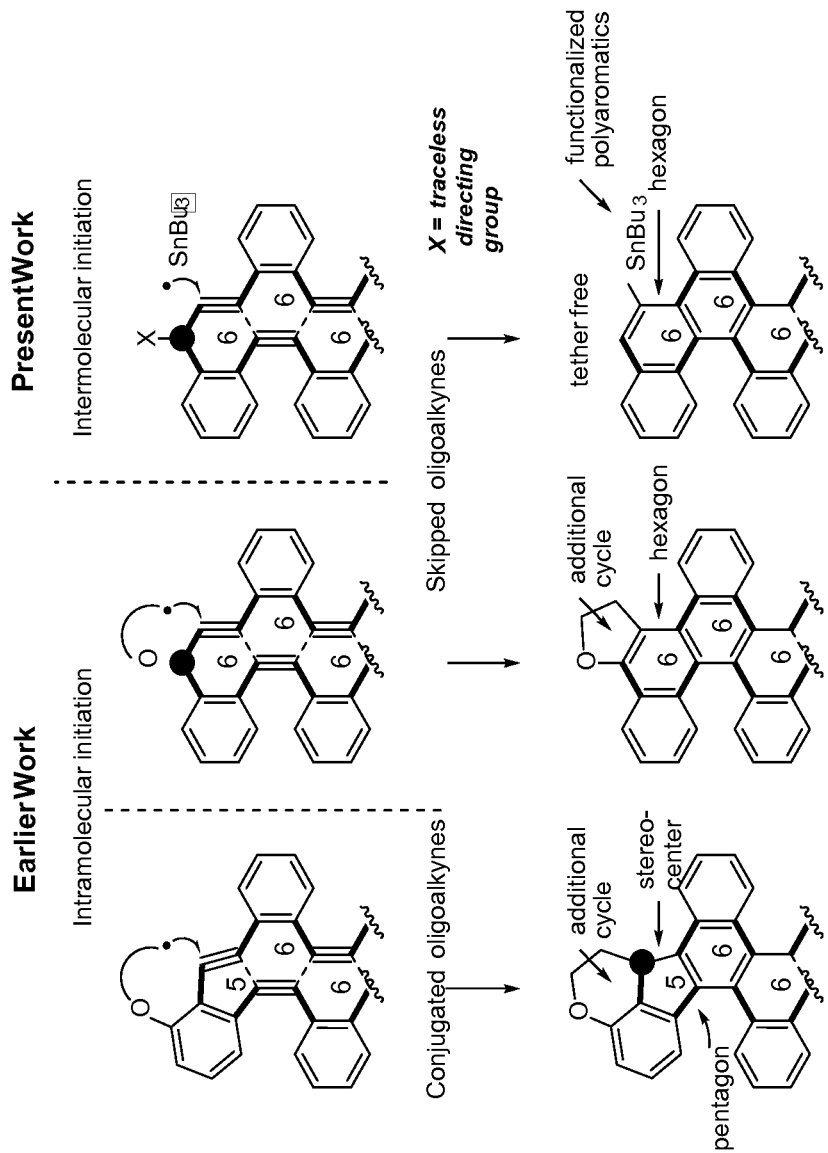
FIG. 2 is a drawing illustrating the evolution of molecular design for the conversion of oligoalkynes into polyaromatic ribbons.
Figure 3:
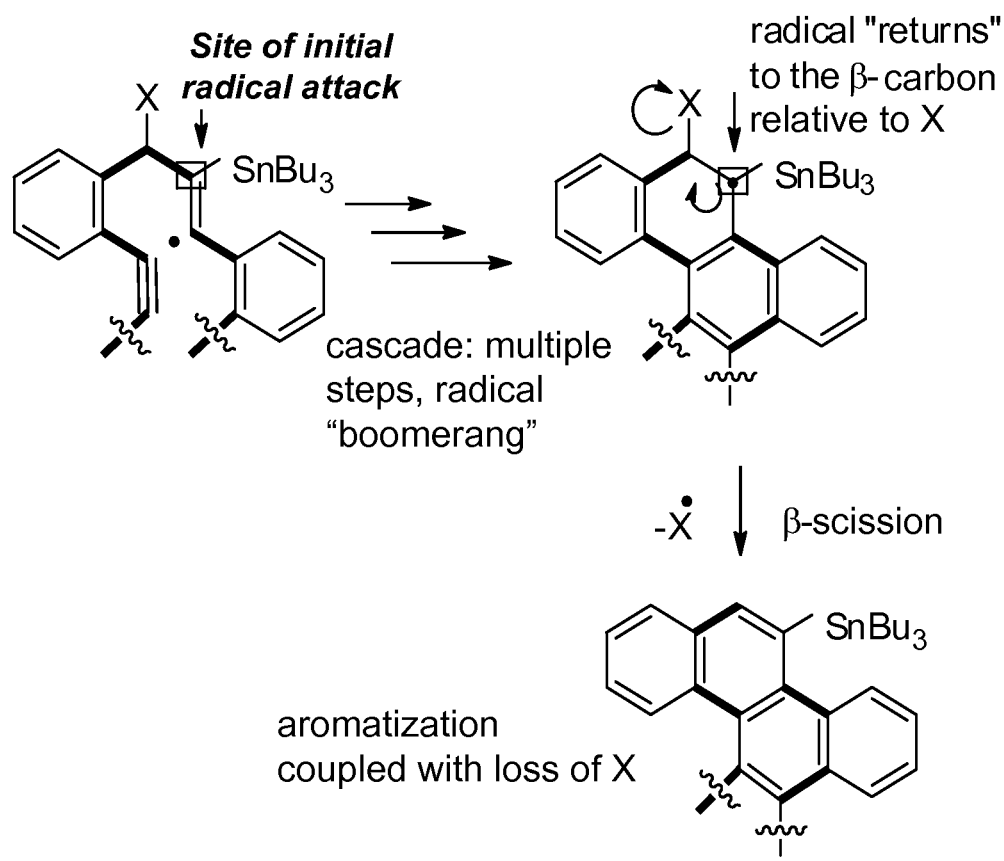
FIG. 3 illustrates a mechanism of a reaction according to the present invention. More specifically.

In order to avoid incorporation of the directing group in the final product, the sequence of bond forming and bond breaking steps in the cascade has to be coordinated to eliminate the directing group at the last step of the cascade, with concomitant aromatization of the polycyclic ribbon. Our hypothesis was that the removal of the alkoxy, e.g., a methoxy, group would benefit from translocation of the radical center if one can design a process where the radical, as a boomerang, returns to the position of the initial intermolecular radical attack to the β-carbon relative to the departing group. See FIG. 3, which is a drawing illustrating a mechanism of a reaction according to the present invention. More specifically, FIG. 3 illustrates translocation of a radical coupled with loss of X.

Under this condition, the loss of directing group occurs via fast β-scission as the last part of a one-pot transformation and, thus, such group can be considered a traceless directing group. See Zhang, F.; David, S. *Chem. Soc. Rev.* 2014, 43, 6906. Not only does this new strategy provide a concise synthetic approach to the defect-free preparation of the top part of the polyaromatic ribbon, but it also retains a stannane substituent, e.g., a $Bu_3Sn$-substituent, as a convenient synthetic handle for further synthetic modifications of the polycyclic framework.

I. DEFINITIONS

It is noted that, as used in this specification and the intended claims, the singular form "a," "an," and "the" include plural referents unless the context clearly dictates otherwise. Thus, for example, reference to "a compound" includes a single compound as well as one or more of the same or different compounds.

As used in the specification and the appended claims, unless specified to the contrary, the following terms have the meaning indicated:

The term "alkenyl", as used herein, means a straight or branched hydrocarbon chain containing from 2 to 10 carbons and containing at least one carbon-carbon double bond. In some embodiments, alkenyl may comprise a straight or branched hydrocarbon chain containing from 2 to 6 carbons and containing at least one carbon-carbon double bond. The term "$C_2$-$C_4$ alkenyl" means an alkenyl group containing 2-4 carbon atoms. Non-limiting examples of alkenyls include buta-2,3-dienyl, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkenylene", as used herein, means a divalent group derived from a straight or branched chain hydrocarbon of 2 to 4 carbon atoms and contains at least one carbon-carbon double. Representative examples of alkenylene include, but are not limited to, —CH=CH— and —$CH_2$CH=CH—.

The term "alkyl", as used herein, means a straight or branched, saturated hydrocarbon chain containing from 1 to 10 carbon atoms, such as from 1 to 8 carbon atoms, or from 1 to 6 carbon atoms. In some embodiments, an alkyl comprises a straight or branched, saturated hydrocarbon chain containing from 1 to 6 carbon atoms. The term "$C_x$-$C_y$ alkyl" means a straight or branched chain, saturated hydrocarbon containing x to y carbon atoms. For example "$C_1$-$C_6$ alkyl" means a straight or branched chain, saturated hydrocarbon containing 1 to 6 carbon atoms. Examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 2-methylpentyl, 2,2-dimethylbutyl, 2-methylhexyl, 3-methylhexyl, 2,2-dimethylpentyl, 2,3-dimethylpentyl, n-heptyl, n-octyl, 2-methylheptyl, 3-methylheptyl, 2,3-dimethylheptyl, isooctyl, n-nonyl, and n-decyl.

The term "alkylene", as used herein, means a divalent group derived from a straight or branched, saturated hydrocarbon chain of 1 to 10 carbon atoms, for example, of 1 to 8 carbon atoms, or of 1 to 6 carbon atoms. The term "$C_1$-$C_6$ alkylenyl", as used herein, means a divalent group derived from a straight or branched hydrocarbon chain of 1 to 6 carbon atoms. Examples of an alkylene include, but are not limited to, —$CH_2$—, —C(H)($CH_3$)—, —$CH_2CH_2$—, —$CH_2CH_2CH_2$—, —$CH_2$CH($CH_3$)—, —$CH_2CH_2CH_2CH_2$—, —$CH_2$CH($CH_3$)$CH_2$—, and —$CH_2$C($CH_3$)$_2CH_2$—.

The term "alkoxy", as used herein, means a straight or branched, saturated hydrocarbon chain containing from 1 to 6 carbon atoms and —O— terminating the hydrocarbon chain. The term "$C_x$-$C_y$ alkoxy," as used herein, means a straight or branched chain, saturated hydrocarbon containing x to y carbon atoms and —O— terminating the hydrocarbon chain. For example "$C_1$-$C_6$ alkoxy" means a straight or branched chain, saturated hydrocarbon containing 1 to 6 carbon atoms and —O— terminating the hydrocarbon chain. Examples of an alkoxy include, but are not limited to, methoxy, ethoxy, n-propoxy, iso-propoxy, n-butoxy, sec-butoxy, iso-butoxy, tert-butoxy, n-pentoxy, isopentoxy, neopentoxy, n-hexoxy, 2-methylpentoxy, and 2,2-dimethylbutoxy.

The term "alkynyl", as used herein, means a straight or branched chain hydrocarbon group containing from 2 to 10 carbon atoms and containing at least one carbon-carbon triple bond. The term "$C_2$-$C_4$ alkynyl", as used herein, means an alkynyl group containing from 2 to 4 carbon atoms. Representative examples of alkynyl include, but are not limited, to acetylenyl, 1-propynyl, 2-propynyl, 3-butynyl, 2-pentynyl, 1-butynyl, and 2-butynyl.

The term "aryl", as used herein, means a phenyl or a bicyclic aryl. The bicyclic aryl may be naphthyl, or a phenyl fused to a monocyclic cycloalkyl, or a phenyl fused to a monocyclic cycloalkenyl. Non-limiting examples of the aryl groups include phenyl, dihydroindenyl (e.g. 2,3-dihydro-1H-inden-1-yl), indenyl, naphthyl, dihydronaphthalenyl, and tetrahydronaphthalenyl (e.g. 1,2,3,4-tetrahydronaphthalen-1-yl). The aryl groups can be unsubstituted or substituted, e.g., with alkyl, halo, haloalkyl, alkoxy, cyano, heterocyclo, etc., and the bicyclic aryl is attached to the parent molecular moiety through any substitutable carbon atom contained within the bicyclic ring system.

The term "cycloalkyl" or "cycloalkane", as used herein, means a monocyclic or a bicyclic ring system. The term "monocyclic cycloalkyl", as used herein, is a carbocyclic ring system containing three to eight carbon atoms, such as three to six carbon atoms, zero heteroatoms and zero double bonds. Examples of monocyclic ring systems include cyclopropyl, cyclobutyl, cyclopentyl, cyclohexyl, cycloheptyl, and cyclooctyl. The bicyclic cycloalkyl is a monocyclic cycloalkyl fused to a monocyclic cycloalkyl ring. The monocyclic or bicyclic cycloalkyl ring may contain one or two alkylene bridges, each consisting of one, two, three, or four carbon atoms, each linking two non-adjacent carbon atoms of the ring system. Non-limiting examples of such bridged cycloalkyl ring systems include bicyclo[3.1.1]heptane, bicyclo[2.2.1]heptane, bicyclo[2.2.2]octane, bicyclo[3.2.2]nonane, bicyclo[3.3.1]nonane, bicyclo[4.2.1]nonane, tricyclo[3.3.1.0$^{3,7}$]nonane (octahydro-2,5-methanopentalene or noradamantane), and tricyclo[3.3.1.1$^{3,7}$]decane (adamantane). The monocyclic and the bicyclic cycloalkyls can be unsubstituted or substituted, e.g., with alkyl, halo, haloalkyl, alkoxy, cyano, heterocyclo, etc., and are attached to the parent molecular moiety through any substitutable atom contained within the ring system.

The term "cycloalkenyl" or "cycloalkene", as used herein, means a monocyclic or a bicyclic hydrocarbon ring system. The monocyclic cycloalkenyl has four, five, six, seven, eight, nine, or ten carbon atoms, e.g., $C_4$-$C_{10}$, or $C_5$-$C_{10}$ cycloalkenyl, and zero heteroatoms. The four-membered ring systems have one double bond, the five- or six-membered ring systems have one or two double bonds, and the seven- or eight-membered ring systems have one, two, or three double bonds. Representative examples of monocyclic cycloalkenyl groups include, but are not limited to, cyclobutenyl, cyclopentenyl, cyclohexenyl, cycloheptenyl, cyclooctenyl, cyclononenyl, cyclodecenyl. The bicyclic cycloalkenyl is a monocyclic cycloalkenyl fused to a monocyclic cycloalkyl group, or a monocyclic cycloalkenyl fused to a monocyclic cycloalkenyl group. The monocyclic or bicyclic cycloalkenyl ring may contain one or two alkylene bridges, each consisting of one, two, three, or four carbon atoms, each linking two non-adjacent carbon atoms of the ring system. Representative examples of the bicyclic cycloalkenyl groups include, but are not limited to, 4,5,6,7-tetrahydro-3aH-indene, octahydronaphthalenyl, and 1,6-dihydro-pentalene. The monocyclic and bicyclic cycloalkenyl can be unsubstituted or substituted, e.g., with alkyl, halo, haloalkyl, alkoxy, cyano, heterocyclo, etc., and are attached to the parent molecular moiety through any substitutable atom contained within the ring systems, and can be unsubstituted or substituted.

The term "halo" or "halogen" or "halide", as used herein, means Cl, Br, I, or F.

The term "haloalkyl", as used herein, means an alkyl group, as defined herein, in which one, two, three, four, five or six hydrogen atoms are replaced by halogen. The term "$C_1$-$C_6$ haloalkyl", as used herein, means a $C_1$-$C_6$ alkyl group, as defined herein, in which one, two, three, four, five, or six hydrogen atoms are replaced by halogen. The term "$C_1$-$C_4$ haloalkyl", as used herein, means a $C_1$-$C_4$ alkyl group, as defined herein, in which one, two, three, four, five, or six hydrogen atoms are replaced by halogen. Representative examples of haloalkyl include, but are not limited to, chloromethyl, fluoromethyl, 2-fluoroethyl, 2,2,2-trifluoroethyl, trifluoromethyl, difluoromethyl, pentafluoroethyl, 2-chloro-3-fluoropentyl, trifluorobutyl (such as, but not limited to, 4,4,4-trifluorobutyl), and trifluoropropyl (such as, but not limited thereto, 3,3,3-trifluoropropyl).

The term "haloaryl", as used herein, means a phenyl or bicyclic aryl in which one, two, three, four, five, six, seven, or eight hydrogen atoms are replaced by halogen. Non-limiting examples of the aryl groups include fluorophenyl, chlorophenyl, bromophenyl, iodophenyl, fluoro-, chloro-, bromo-, or iodo-dihydroindenyl (e.g. 2,3-dihydro-1H-inden-1-yl), fluoro-, chloro-, bromo-, or iodo-indenyl, fluoro-, chloro-, bromo-, or iodo-naphthyl, fluoro-, chloro-, bromo-, or iodo-dihydronaphthalenyl, and fluoro-, chloro-, bromo-, or iodo-tetrahydronaphthalenyl (e.g. 1,2,3,4-tetrahydronaphthalen-1-yl).

The term "heterocycle" or "heterocyclic", as used herein, means a monocyclic heterocycle or a bicyclic heterocycle. The monocyclic heterocycle, as used herein, is a three-, four-, five-, six-, seven-, eight-, nine-, or ten-membered ring containing at least one heteroatom independently selected from the group consisting of O, N, and S. The three-, four-, five-, six-, seven-, eight-, nine-, or ten-membered ring contains zero or one double bond, and one heteroatom selected from the group consisting of O, N, and S. The four-, five-, six-, seven-, eight-, nine-, or ten-membered heterocyclic ring contains zero or one double bond, and one heteroatom selected from the group consisting of O, N, and S. The five-membered ring contains zero or one double bond and one, two, or three heteroatoms selected from the group consisting of O, N, and S. The six-membered ring contains zero, one, or two double bonds and one, two, or three heteroatoms selected from the group consisting of O, N, and S. The seven- and eight-membered rings contains zero, one, two, or three double bonds and one, two, or three heteroatoms selected from the group consisting of O, N, and S. Non-limiting examples of monocyclic heterocycles include azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, oxetanyl, piperazinyl, piperidinyl, pyranyl, pyrazolinyl, pyrazolidinyl, pyrrolinyl, pyrrolidinyl, tetrahydrofuranyl, tetrahydropyranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl. The bicyclic heterocycle, as used herein, is a monocyclic heterocycle fused to a phenyl group, or a monocyclic heterocycle fused to a monocyclic cycloalkyl, or a monocyclic heterocycle fused to a monocyclic cycloalkenyl, or a monocyclic heterocycle fused to a monocyclic heterocycle. Non-limiting examples of bicyclic heterocycles include e.g. dihydrochromenyl (e.g. 3,4-dihydro-2H-chromen-4-yl), benzopyranyl, benzothiopyranyl, 2,3-dihydrobenzofuranyl, 2,3-dihydrobenzothienyl, and 2,3-dihydro-1H-indolyl. The monocyclic and the bicyclic heterocycles may contain an alkenylene bridge of two, three, or four carbon atoms, or one or two alkylene bridges of 1, 2, 3, or 4 carbon atoms, or combinations thereof, wherein each bridge links two non-adjacent atoms of the ring system. Non-limiting examples of such bridged heterocycles include octahydro-2,5-epoxypentalene, azabicyclo [2.2.1]heptyl (including 2-azabicyclo[2.2.1]hept-2-yl), hexahydro-2H-2,5-methanocyclopenta[b]furan, hexahydro-1H-1,4-methanocyclopenta[c]furan, aza-admantane (1-azatricyclo[3.3.1.1$^{3,7}$]decane), and oxa-adamantane (2-oxatricyclo[3.3.1.1$^{3,7}$]decane). In some embodiments, a 4- to 10-membered ring heterocyclyl may be selected from among 2,3-dihydrofuranyl, 2,5-dihydrofuranyl, tetrahydrofuranyl, 1,3-dioxolanyl, 1,3-dioxanyl, tetrahydro-2H-pyranyl, 3,4-dihydro-2H-pyranyl, 3,6-dihydro-2H-pyranyl, 2H-pyranyl, 4H-pyranyl, pyrrolidinyl, 2,3-dihydro-1H-pyrrolyl, 2,5-dihydro-1H-pyrrolyl, 4H-1,3-dioxinyl, 1,4-dioxanyl, 2,3-dihydro-1,4-dioxinyl, piperidinyl, 2-oxa-7-azaspiro [3.5]nonanyl, 1,2-dihydropyridinyl, 1,4-dihydropyridinyl, 2,3-dihydropyridinyl, 3,4-dihydropyridinyl, 1,2,3,6-tetrahydropyridinyl, isoxazolidinyl, oxazolidinyl, 2,3-dihydroisoxazolyl, 2,5-dihydroisoxazolyl, and morpholino, each of which may be substituted or unsubstituted. The monocyclic and the bicyclic heterocycles can be unsubstituted or substituted, e.g., with alkyl, halo, haloalkyl, alkoxy, cyano, heterocyclo, cycloalkyl, sulfonyl, etc., and are connected to the parent molecular moiety through any substitutable carbon atom or any substitutable nitrogen atom contained within the rings. The nitrogen and sulfur heteroatoms in the heterocycle rings may optionally be oxidized and the nitrogen atoms may optionally be quaternized.

The term "heteroaryl", as used herein, means a monocyclic heteroaryl or a bicyclic heteroaryl. The heteroaryl may comprise 5- to 10-membered ring. The monocyclic heteroaryl is a five- or six-membered ring. The five-membered ring contains two double bonds. The five membered ring may contain one heteroatom selected from O or S; or one, two, three, or four nitrogen atoms and optionally one oxygen or one sulfur atom. The six-membered ring contains three double bonds and one, two, three or four nitrogen atoms. Representative examples of monocyclic heteroaryl include, but are not limited to, furanyl, imidazolyl, isoxazolyl, isothiazolyl, oxadiazolyl, 1,3-oxazolyl, pyridinyl, pyridazinyl, pyrimidinyl, pyrazinyl, pyrazolyl, pyrrolyl, tetrazolyl, thiadiazolyl, 1,3-thiazolyl, thienyl, triazolyl, and triazinyl. The bicyclic heteroaryl consists of a monocyclic heteroaryl fused to a phenyl, or a monocyclic heteroaryl fused to a monocyclic cycloalkyl, or a monocyclic heteroaryl fused to a monocyclic cycloalkenyl, or a monocyclic heteroaryl fused to a monocyclic heteroaryl, or a monocyclic heteroaryl fused to a monocyclic heterocycle. Non-limiting examples of bicyclic heteroaryl groups include benzofuranyl, benzothienyl, benzoxazolyl, benzimidazolyl, benzoxadiazolyl, 6,7-dihydro-5H-cyclopenta[b]pyridinyl (e.g. 6,7-dihydro-5H-cyclopenta[b]pyridin-7-yl), 6,7-dihydro-1,3-benzothiazolyl, imidazo[1,2-a]pyridinyl, indazolyl, indolyl, isoindolyl, isoquinolinyl, naphthyridinyl, pyridoimidazolyl, quinolinyl, thiazolo[5,4-b]pyridin-2-yl, thiazolo[5,4-d]pyrimidin-2-yl, and 5,6,7,8-tetrahydroquinolinyl (e.g. 5,6,7,8-tetrahydroquinolin-5-yl, 5,6,7,8-tetrahydroquinolin-8-yl). In some embodiments, 5- to 10-membered ring heteroaryl may be selected from among pyridinyl, pyrimidinyl, pyrazinyl, 1H-indolyl, 2H-indolyl, pyrazolyl, 1H-imidazolyl, oxazolyl, isoxazolyl, pyrazolyl, quinolinyl, isoquinolinyl, furo[3,2-b] pyridinyl, furo[4,3-b]pyridinyl, furo[5,4-b]pyridinyl, and benzo[c][1,2,5]oxadiazol-5-yl, each of which may be substituted or unsubstituted. The monocyclic and bicyclic heteroaryl groups can be substituted, e.g., with alkyl, halo, haloalkyl, alkoxy, cyano, heterocyclo, cycloalkyl, sulfonyl, etc., or unsubstituted and are connected to the parent molecular moiety through any substitutable carbon atom or any substitutable nitrogen atom contained within the ring systems.

The term "heteroatom", as used herein, means a nitrogen, oxygen, or sulfur atom.

The term "oxo", as used herein, means a =O group.

The term "carbonyl", as used herein, means a

group. A "carbonyl" group may alternatively be disclosed as —C(O)—.

The term "carboxy" or "carboxyl", as used herein, means a

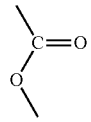

group. A "carboxy" or "carboxyl" group may alternatively be disclosed as —C(O)O—.

The term "hydroxy" or "hydroxyl", as used herein, means a —OH group. In some embodiments, a hydroxy or hydroxyl group may be bonded to an alkyl thereby forming an hydroxyalkyl, such as, but not limited to hydroxymethyl, hydroxyethyl, etc.

The term "cyano", as used herein, means a —C≡N group.

The term "imino", as used herein, means a

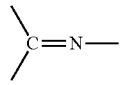

group. The imino may be bonded to one, two, or three groups, such as, but not limited to, alkyl, hydroxyl, alkoxy.

The term "thio", as used herein, means a group comprising a —S— group.

The term "sulfonyl", as used herein, means a group comprising a

group.

The term "phosphate", as used herein, means a —PO$_3$H$_2$ group. One or both hydrogens in a phosphate may be replaced with cations, such as sodium or potassium.

II. SYNTHESIS

In some embodiments, the method of the present invention is directed to the synthesis of a polycyclic aromatic compound. In some embodiments, the polycyclic aromatic compound has a structure (1-a) as follows:

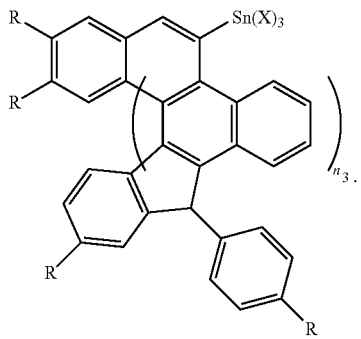

Structure (1-a)

In some embodiments of the compound having structure (1-a), each R is independently selected from the group consisting of hydrogen, halogen, cyano, $C_1$-$C_6$ alkyl, and $C_1$-$C_6$ alkoxy. In some embodiments of the compound having structure (1-a), each R is independently selected from the group consisting of hydrogen, methoxy, trifluoromethyl, cyano, fluoro, and n-butyl carbonyl. In some embodiments, each R is hydrogen.

In the compound having structure (1-a), X is a $C_1$-$C_6$ alkyl or phenyl.

In the compound having structure (1-a), $n_3$ has a value between 1 and about 100, such as between 1 and about 50, such as between 1 and about 20. In some embodiments, $n_3$ has a value of 1, 2, 3, 4 or more.

In some embodiments, a compound having structure (1-a) may be prepared by contacting a compound having structure (I) with a stannane compound in the presence of a radical initiator to thereby prepare the polycyclic aromatic compound.

In some embodiments, the reactant compound having structure (I) is as follows:

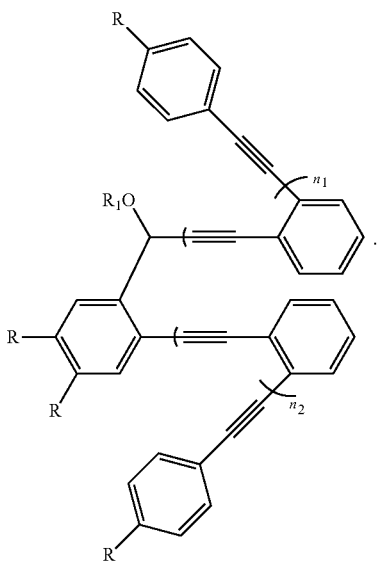

Structure (I)

In some embodiments of the compound having structure (I), each R is independently selected from the group consisting of hydrogen, halogen, cyano, $C_1$-$C_6$ alkyl, and $C_1$-$C_6$ alkoxy. In some embodiments of the compound having structure (I), each R is independently selected from the group consisting of hydrogen, methoxy, trifluoromethyl, cyano, fluoro, and n-butyl carbonyl. In some embodiments, each R is hydrogen.

In the compound having structure (I), $R_1$ is selected from the group consisting of $C_1$-$C_6$ alkyl, —$CH_2OCH_3$, and —$CH_2CH_2OCH_3$. In some embodiments, $R_1$ is selected from the group consisting of $C_1$-$C_6$ alkyl, such as methyl, ethyl, isopropyl, n-propyl, and the like. In some embodiments, $R_1$ is methyl.

In the compound having structure (I), $n_1$ and $n_2$ each independently have a value between 0 and 50. In some embodiments, $n_1$ and $n_2$ have the same value. In some embodiments, $n_1=n_2+1$. $n_3$ from structure (1-a) is related to $n_1$ and $n_2$ in that $n_3$ has a value of $n_1+n_2$.

In some embodiments, $n_1$ and $n_2$ each independently have a value between 0 and 25, such as between about 1 and about 25, or between about 1 and about 5. Further, $n_1$ and $n_2$ have the same value.

In some embodiments, $n_1$ and $n_2$ each independently have a value between 0 and 25, such as between about 1 and about 25, or between about 1 and about 5. Further, $n_1=n_2+1$.

In some embodiments, the stannane compound has a general formula $X_3SnH$, wherein X is a $C_1$-$C_6$ alkyl or phenyl. In some embodiments, the stannane compound is selected from the group consisting of trimethyl stannane, triethyl stannane, tri(n-propyl)stannane, tri(isopropyl)stannane, tri(n-butyl)stannane, tri(isobutyl)stannane, triphenyl stannane, and any combination there. The identity of X in structure (1-a) is determined primarily, if not wholly, by the stannane compound. In some preferred embodiments, the stannane compound is tri(n-butyl)stannane.

In some embodiments, the radical initiator is any compound that can provide radicals for the initiation step of a radical chain reaction. In some embodiments, the radical initiator is any compound that converts the stannane compound (generally, $X_3SnH$, wherein X is a $C_1$-$C_6$ alkyl or phenyl) into $X_3Sn$ radical. Suitable radical initiators include azo compounds, inorganic peroxides, or organic peroxides. In some embodiments, the radical initiator is Azobisisobutyronitrile (2,2'-azobis(2-methylpropionitrile), AIBN). In some embodiments, the radical initiator is 1,1'-Azobis(cyclohexanecarbonitrile) (ABCN), In some embodiments, the radical initiator is di-tert-butyl peroxide (TOOT, or DTBPB). In some embodiments, the radical initiator is benzoyl peroxide.

The contact may occur in a solvent, suitably an aprotic solvent. Solvents suitable for the reaction of the present invention include benzene, diethyl ether, toluene, tetrahydrofuran, hexane, and dichloromethane. In some preferred embodiments, the solvent is toluene or benzene, with toluene being particularly preferred.

After synthesis of the polycyclic aromatic compound having structure (1-a), this reaction comprises a stannyl moiety, which may be removed by contact with acid or contacted with other reagents in order to incorporate functionality onto the polycyclic aromatic compound.

In some embodiments, the polycyclic aromatic compound having structure (1-a) is contacted with an acid to remove the stannyl moiety and thereby prepare a polycyclic aromatic compound having structure (1-b):

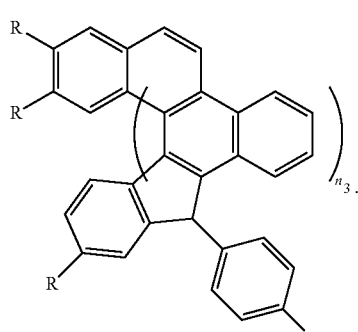

Structure (1-b)

In some embodiments of the compound having structure (1-b), each R is independently selected from the group consisting of hydrogen, halogen, cyano, $C_1$-$C_6$ alkyl, and $C_1$-$C_6$ alkoxy. In some embodiments of the compound having structure (1-b), each R is independently selected from the group consisting of hydrogen, methoxy, trifluoromethyl, cyano, fluoro, and n-butyl carbonyl. In some embodiments, each R is hydrogen.

In the compound having structure (1-b), $n_3$ has a value between 1 and about 100, such as between 1 and about 50, such as between 1 and about 20. In some embodiments, $n_3$ has a value of 1, 2, 3, 4 or more.

Any acid suitable for removing the stannyl functional group may be used, such as hydrochloric acid, hydrobromic acid, hydroiodic acid, nitric acid, sulfuric acid, and the like.

In some embodiments, the polycyclic aromatic compound having structure (1-a) has the following structure (1-c), wherein the value of $N_3$ is 1:

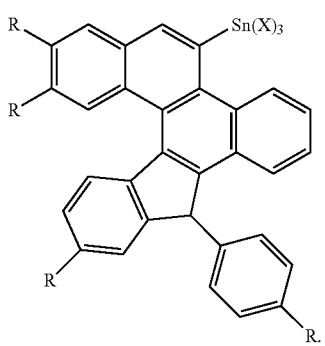

Structure (1-c)

In some embodiments of the compound having structure (1-c), each R is independently selected from the group consisting of hydrogen, halogen, cyano, $C_1$-$C_6$ alkyl, and $C_1$-$C_6$ alkoxy. In some embodiments of the compound having structure (1-c), each R is independently selected from the group consisting of hydrogen, methoxy, trifluoromethyl, cyano, fluoro, and n-butyl carbonyl. In some embodiments, each R is hydrogen.

In the compound having structure (1-c), X is a $C_1$-$C_6$ alkyl or phenyl.

In some embodiments, the polycyclic aromatic compound having structure (1-c) is contacted with an acid to thereby prepare a polycyclic aromatic compound having structure (1-d):

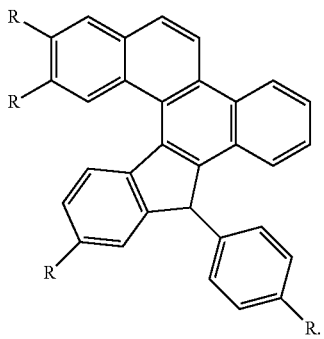

Structure (1-d)

In some embodiments of the compound having structure (1-d), each R is independently selected from the group consisting of hydrogen, halogen, cyano, $C_1$-$C_6$ alkyl, and $C_1$-$C_6$ alkoxy. In some embodiments of the compound having structure (1-d), each R is independently selected from the group consisting of hydrogen, methoxy, trifluoromethyl, cyano, fluoro, and n-butyl carbonyl. In some embodiments, each R is hydrogen.

In some embodiments, the polycyclic aromatic compound having structure (1-a) has the following structure (1-e), wherein the value of $N_3$ is 2:

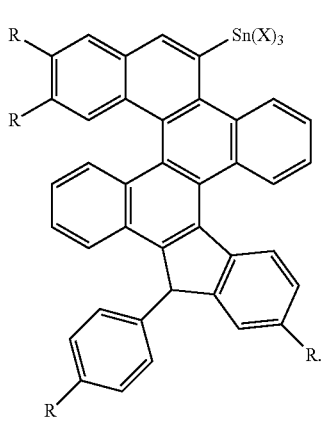

Structure (1-e)

In some embodiments of the compound having structure (1-e), each R is independently selected from the group consisting of hydrogen, halogen, cyano, $C_1$-$C_6$ alkyl, and $C_1$-$C_6$ alkoxy. In some embodiments of the compound having structure (1-e), each R is independently selected from the group consisting of hydrogen, methoxy, trifluoromethyl, cyano, fluoro, and n-butyl carbonyl. In some embodiments, each R is hydrogen.

In the compound having structure (1-c), X is a $C_1$-$C_6$ alkyl or phenyl.

In some embodiments, the polycyclic aromatic compound having structure (1-e) is contacted with an acid to thereby prepare a polycyclic aromatic compound having structure (1-f):

Structure (1-f)

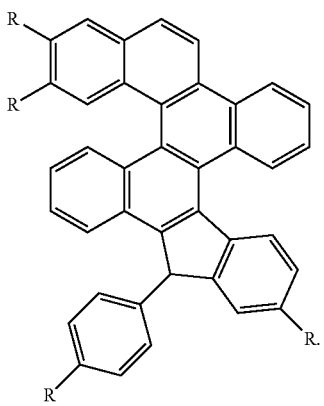

In some embodiments of the compound having structure (1-f), each R is independently selected from the group consisting of hydrogen, halogen, cyano, $C_1$-$C_6$ alkyl, and $C_1$-$C_6$ alkoxy. In some embodiments of the compound having structure (1-f), each R is independently selected from the group consisting of hydrogen, methoxy, trifluoromethyl, cyano, fluoro, and n-butyl carbonyl. In some embodiments, each R is hydrogen.

Any acid suitable for removing the stannyl functional group may be used, such as hydrochloric acid, hydrobromic acid, hydroiodic acid, nitric acid, sulfuric acid, and the like.

In some embodiments, polycyclic aromatic compounds of increasing number of conjugated rings may be prepared by using starting reactant compound having structure (I) having higher values of $n_1$ and $n_2$. For example, the following stannylated structures may be prepared by the method of the present invention:

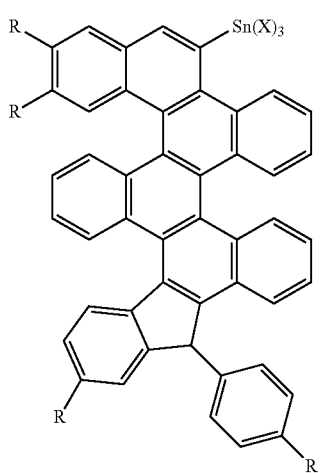

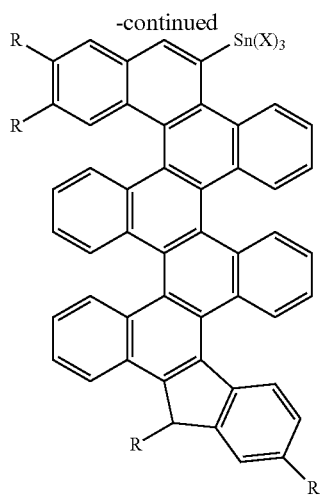

In the above exemplary compounds, each R is independently selected from the group consisting of hydrogen, halogen, cyano, $C_1$-$C_6$ alkyl, and $C_1$-$C_6$ alkoxy. In some embodiments, each R is independently selected from the group consisting of hydrogen, methoxy, trifluoromethyl, cyano, fluoro, and n-butyl carbonyl. In some embodiments, each R is hydrogen. X is a $C_1$-$C_6$ alkyl or phenyl. These compounds may be reacted with acid in order to remove the stannyl moiety. Still higher levels of conjugation may be achieved from increasingly larger starting oligoalkynes.

In some embodiments, the method of the present invention is directed to preparing a polycyclic aromatic compound having a structure (1-g) as follows:

Structure (1-g)

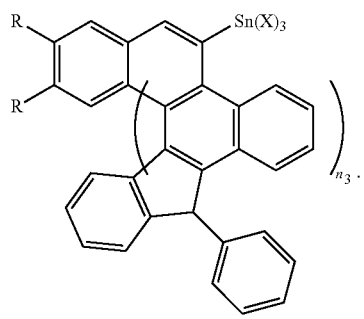

In some embodiments of the compound having structure (1-g), each R is independently selected from the group consisting of hydrogen, halogen, cyano, $C_1$-$C_6$ alkyl, and $C_1$-$C_6$ alkoxy. In some embodiments of the compound having structure (1-g), each R is independently selected from the group consisting of hydrogen, methoxy, trifluoromethyl, cyano, fluoro, and n-butyl carbonyl. In some embodiments, each R is hydrogen.

In the compound having structure (1-g), X is a $C_1$-$C_6$ alkyl or phenyl.

In the compound having structure (1-g), $n_3$ has a value between 1 and about 100, such as between 1 and about 50, such as between 1 and about 20. In some embodiments, $n_3$ has a value of 1, 2, 3, 4 or more.

In some embodiments, a compound having structure (1-g) may be prepared by contacting a compound having structure (II) with a stannane compound in the presence of a radical initiator to thereby prepare the polycyclic aromatic compound.

In some embodiments, the reactant compound having structure (II) is as follows:

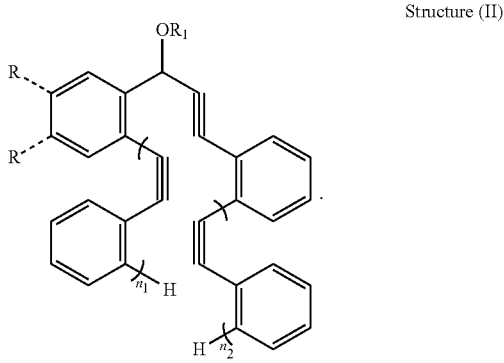

Structure (II)

In the compound having structure (II), each R is independently selected from the group consisting of hydrogen, halogen, cyano, $C_1$-$C_6$ alkyl, and $C_1$-$C_6$ alkoxy. In some embodiments of the compound having structure (II), each R is independently selected from the group consisting of hydrogen, methoxy, trifluoromethyl, cyano, fluoro, and n-butyl carbonyl. In some embodiments, each R is hydrogen.

In the compound having structure (II), $R_1$ is selected from the group consisting of $C_1$-$C_6$ alkyl, —$CH_2OCH_3$, and —$CH_2CH_2OCH_3$. In some embodiments, $R_1$ is selected from the group consisting of $C_1$-$C_6$ alkyl, such as methyl, ethyl, isopropyl, n-propyl, and the like. In some embodiments, $R_1$ is methyl.

In the compound having structure (II), $n_1$ and $n_2$ each independently have a value between 0 and 50. In some embodiments, $n_1$ and $n_2$ have the same value. In some embodiments, $n_1$=$n_2$+1. $n_3$ from structure (1-g) is related to $n_1$ and $n_2$ in that $n_3$ has a value of $n_1$+$n_2$.

In some embodiments, $n_1$ and $n_2$ each independently have a value between 0 and 25, such as between about 1 and about 25, or between about 1 and about 5. Further, $n_1$ and $n_2$ have the same value.

In some embodiments, $n_1$ and $n_2$ each independently have a value between 0 and 25, such as between about 1 and about 25, or between about 1 and about 5. Further, $n_1$=$n_2$+1.

In some embodiments, the stannane compound has a general formula $X_3SnH$, wherein X is a $C_1$-$C_6$ alkyl or phenyl. In some embodiments, the stannane compound is selected from the group consisting of trimethyl stannane, triethyl stannane, tri(n-propyl)stannane, tri(isopropyl)stannane, tri(n-butyl)stannane, tri(isobutyl)stannane, triphenyl stannane, and any combination there. The identity of X in structure (1-g) is determined primarily, if not wholly, by the stannane compound. In some preferred embodiments, the stannane compound is tri(n-butyl)stannane.

In some embodiments, the radical initiator is any compound that can provide radicals for the initiation step of a radical chain reaction. In some embodiments, the radical initiator is any compound that converts the stannane compound (generally, $X_3SnH$, wherein X is a $C_1$-$C_6$ alkyl or phenyl) into $X_3Sn$ radical. Suitable radical initiators include azo compounds, inorganic peroxides, or organic peroxides. In some embodiments, the radical initiator is Azobisisobutyronitrile (2,2'-azobis(2-methylpropionitrile), AIBN). In some embodiments, the radical initiator is 1,1'-Azobis(cyclohexanecarbonitrile) (ABCN). In some embodiments, the radical initiator is di-tert-butyl peroxide (TOOT, or DTBPB). In some embodiments, the radical initiator is benzoyl peroxide.

The contact may occur in a solvent, suitably an aprotic solvent. Solvents suitable for the reaction of the present invention include benzene, diethyl ether, toluene, tetrahydrofuran, hexane, and dichloromethane. In some preferred embodiments, the solvent is toluene or benzene, with toluene being particularly preferred.

After synthesis of the polycyclic aromatic compound having structure (1-g), this reaction comprises a stannyl moiety, which may be removed by contact with acid or contacted with other reagents in order to incorporate functionality onto the polycyclic aromatic compound.

In some embodiments, the polycyclic aromatic compound having structure (1-g) is contacted with an acid to remove the stannyl moiety and thereby prepare a polycyclic aromatic compound having structure (1-h):

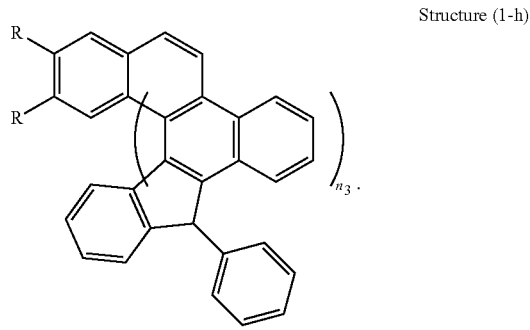

Structure (1-h)

In the compound having structure (1-h), each R is independently selected from the group consisting of hydrogen, halogen, cyano, $C_1$-$C_6$ alkyl, and $C_1$-$C_6$ alkoxy. In some embodiments of the compound having structure (1-h), each R is independently selected from the group consisting of hydrogen, methoxy, trifluoromethyl, cyano, fluoro, and n-butyl carbonyl. In some embodiments, each R is hydrogen.

In the compound having structure (1-h), $n_3$ has a value between 1 and about 100, such as between 1 and about 50, such as between 1 and about 20. In some embodiments, $n_3$ has a value of 1, 2, 3, 4 or more. Any acid suitable for removing the stannyl functional group may be used, such as hydrochloric acid, hydrobromic acid, hydroiodic acid, nitric acid, sulfuric acid, and the like.

According to the method of the present invention, still higher levels of conjugation may be achieved from increasingly larger starting oligoalkynes.

In some embodiments, the method of the present invention is directed to preparing a polycyclic aromatic compound having a structure (2-a) as follows:

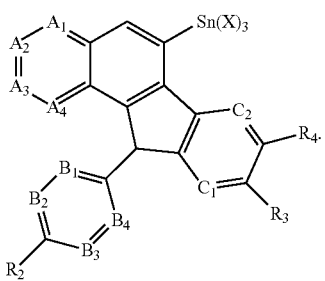

Structure (2-a)

In the context of Structure (2-a), $A_1$, $A_2$, $A_3$, and $A_4$ are either C—R or N, wherein at least two of $A_1$, $A_2$, $A_3$, and $A_4$ are C—R, and each R is independently selected from the group consisting of hydrogen, halogen, $C_1$-$C_6$ alkyl, and $C_1$-$C_6$ alkoxy. In some embodiments, $A_1$, $A_2$, $A_3$, and $A_4$ are each C—H. In some embodiments, $A_1$, $A_2$, $A_3$ are each C—H and $D_1$ is N.

In the context of Structure (2-a), $B_1$, $B_2$, $B_3$, and $B_4$ are either C—R or N, wherein at least two of $B_1$, $B_2$, $B_3$, and $B_4$ are C—R, and each R is independently selected from the group consisting of hydrogen, halogen, $C_1$-$C_6$ alkyl, and $C_1$-$C_6$ alkoxy. In some embodiments, $B_1$, $B_2$, $B_3$, and $B_4$ are each C—H.

In the context of Structure (2-a), $C_1$ and $C_2$ are either C—R or N, and each R is independently selected from the group consisting of hydrogen, halogen, $C_1$-$C_6$ alkyl, and $C_1$-$C_6$ alkoxy. In some embodiments, $C_1$ and $C_2$ are each C—H.

In the context of Structure (2-a), $R_2$, $R_3$, and $R_4$ are each independently selected from the group consisting of hydrogen, halogen, cyano, nitro, $C_1$-$C_6$-alkyl, $C_1$-$C_6$ alkoxy, hydroxy-$C_1$-$C_6$-alkyl, halo-$C_1$-$C_6$-alkyl cyano-$C_1$-$C_6$-alkyl, $C_1$-$C_6$-alkoxy-$C_1$-$C_6$-alkyl, $C_1$-$C_6$-alkylcarbonyl, $C_1$-$C_6$-alkoxycarbonyl, $C_1$-$C_6$-alkoxycarbonyl-$C_1$-$C_6$-alkyl, $C_3$-$C_6$-cycloalkyl, $C_3$-$C_6$-cycloalkyl-$C_1$-$C_6$-alkyl, $C_5$-$C_{10}$-cycloalkenyl, aryl, aryl-$C_1$-$C_6$-alkyl, 4- to 10-membered ring heterocyclyl, 4- to 10-membered ring heterocyclyl-$C_1$-$C_6$-alkyl, 5- to 10-membered ring heteroaryl, 5- to 10-membered ring heteroaryl-$C_1$-$C_6$-alkyl, —$OR^{104}$, —$C(O)OR^{105}$, —$N(R^{106})C(O)R^{107}$, —$N(R^{108})C(O)NR^{109}R^{110}$, —$S(O)_2R^{111}$, —$S(O)_2NR^{112}R^{113}$, and —$NS(O)_2NR^{112}R^{113}$; wherein $R^{104}$, $R^{105}$, $R^{106}$, $R^{107}$, $R^{107}$, $R^{109}$, $R^{110}$, $R^{111}$, $R^{112}$, and $R^{113}$ are independently selected from the group consisting of hydrogen, $C_1$-$C_8$-alkyl, $C_1$-$C_8$-alkoxy, halo-$C_1$-$C_8$-alkyl, cyano-$C_1$-$C_8$-alkyl, $C_3$-$C_6$-cycloalkyl, halo-$C_3$-$C_6$-cycloalkyl, 4- to 10-membered ring heterocyclyl, 4- to 10-membered ring heterocyclyl-$C_1$-$C_8$-alkyl, aryl, haloaryl, and $C_1$-$C_8$-alkylaryl.

In some embodiments, $R_2$, $R_3$, and $R_4$ are each independently selected from the group consisting of hydrogen, methoxy, trifluoromethyl, cyano, fluoro, and n-butyl carbonyl. In some embodiments, $R_2$, $R_3$, and $R_4$ are each hydrogen. In some embodiments, $R_2$ is hydrogen, and $R_3$ and $R_4$ together with the phenyl ring to which they are bonded form a naphthalene ring.

In the context of Structure (2-a), X is a $C_1$-$C_6$ alkyl or phenyl.

In some embodiments, a compound having structure (2-a) may be prepared by contacting a compound having structure (III) with a stannane compound in the presence of a radical initiator to thereby prepare the polycyclic aromatic compound.

In some embodiments, the reactant compound having structure (III) is as follows:

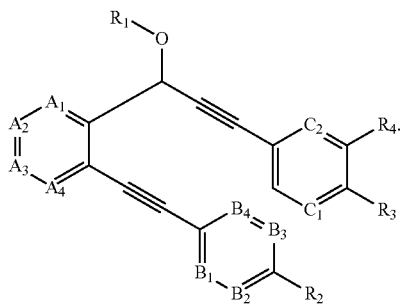

Structure (III)

In the context of Structure (III), $A_1$, $A_2$, $A_3$, and $A_4$ are either C—R or N, wherein at least two of $A_1$, $A_2$, $A_3$, and $A_4$ are C—R, and each R is independently selected from the group consisting of hydrogen, halogen, $C_1$-$C_6$ alkyl, and $C_1$-$C_6$ alkoxy. In some embodiments, $A_1$, $A_2$, $A_3$, and $A_4$ are each C—H. In some embodiments, $A_1$, $A_2$, $A_3$ are each C—H and $D_1$ is N.

In the context of Structure (III), $B_1$, $B_2$, $B_3$, and $B_4$ are either C—R or N, wherein at least two of $B_1$, $B_2$, $B_3$, and $B_4$ are C—R, and each R is independently selected from the group consisting of hydrogen, halogen, $C_1$-$C_6$ alkyl, and $C_1$-$C_6$ alkoxy. In some embodiments, $B_1$, $B_2$, $B_3$, and $B_4$ are each C—H.

In the context of Structure (III), $C_1$ and $C_2$ are either C—R or N, and each R is independently selected from the group consisting of hydrogen, halogen, $C_1$-$C_6$ alkyl, and $C_1$-$C_6$ alkoxy. In some embodiments, $C_1$ and $C_2$ are each C—H.

In the context of Structure (III), $R_1$ is selected from the group consisting of $C_1$-$C_6$ alkyl, —$CH_2OCH_3$, and —$CH_2CH_2OCH_3$. In some embodiments, $R_1$ is selected from the group consisting of $C_1$-$C_6$ alkyl, such as methyl, ethyl, isopropyl, n-propyl, and the like. In some embodiments, $R_1$ is methyl.

In the context of Structure (III), $R_2$, $R_3$, and $R_4$ are each independently selected from the group consisting of hydrogen, halogen, cyano, nitro, $C_1$-$C_6$-alkyl, $C_1$-$C_6$ alkoxy, hydroxy-$C_1$-$C_6$-alkyl, halo-$C_1$-$C_6$-alkyl, cyano-$C_1$-$C_6$-alkyl, $C_1$-$C_6$-alkoxy-$C_1$-$C_6$-alkyl, $C_1$-$C_6$-alkylcarbonyl, $C_1$-$C_6$-alkoxycarbonyl, $C_1$-$C_6$-alkoxycarbonyl-$C_1$-$C_6$-alkyl, $C_3$-$C_6$-cycloalkyl, $C_3$-$C_6$-cycloalkyl-$C_1$-$C_6$-alkyl, $C_5$-$C_{10}$-cycloalkenyl, aryl, aryl-$C_1$-$C_6$-alkyl, 4- to 10-membered ring heterocyclyl, 4- to 10-membered ring heterocyclyl-$C_1$-$C_6$-alkyl, 5- to 10-membered ring heteroaryl, 5- to 10-membered ring heteroaryl-$C_1$-$C_6$-alkyl, —$OR^{104}$, —$C(O)OR^{105}$, —$N(R^{106})C(O)^{107}$, —$N(R^{108})C(O)NR^{109}R^{110}$, —$S(O)_2R^{111}$, —$S(O)_2NR^{112}R^{113}$, and —$NS(O)_2NR^{112}R^{113}$; wherein $R^{104}$, $R^{105}$, $R^{106}$, $R^{107}$, $R^{107}$, $R^{109}$, $R^{110}$, $R^{111}$, $R^{112}$, and $R^{113}$ are independently selected from the group consisting of hydrogen, $C_1$-$C_8$-alkyl, $C_1$-$C_8$-alkoxy, halo-$C_1$-$C_8$-alkyl, cyano-$C_1$-$C_8$-alkyl, $C_3$-$C_6$-cycloalkyl, halo-$C_3$-$C_6$-cycloalkyl, 4- to 10-membered ring heterocyclyl, 4- to 10-membered ring heterocyclyl-$C_1$-$C_8$-alkyl, aryl, haloaryl, and $C_1$-$C_8$-alkylaryl.

In some embodiments, $R_2$, $R_3$, and $R_4$ are each independently selected from the group consisting of hydrogen, methoxy, trifluoromethyl, cyano, fluoro, and n-butyl carbonyl. In some embodiments, $R_2$, $R_3$, and $R_4$ are each hydrogen. In some embodiments, R$_2$ is hydrogen, and R$_3$, and R$_4$ together with the phenyl ring to which they are bonded form a naphthalene ring.

In some embodiments, the stannane compound has a general formula X$_3$SnH, wherein X is a C$_1$-C$_6$ alkyl or phenyl. In some embodiments, the stannane compound is selected from the group consisting of trimethyl stannane, triethyl stannane, tri(n-propyl)stannane, tri(isopropyl)stannane, tri(n-butyl)stannane, tri(isobutyl)stannane, triphenyl stannane, and any combination there. The identity of X in structure (1-g) is determined primarily, if not wholly, by the stannane compound. In some preferred embodiments, the stannane compound is tri(n-butyl)stannane.

In some embodiments, the radical initiator is any compound that can provide radicals for the initiation step of a radical chain reaction. In some embodiments, the radical initiator is any compound that converts the stannane compound (generally, X$_3$SnH, wherein X is a C$_1$-C$_6$ alkyl or phenyl) into X$_3$Sn radical. Suitable radical initiators include azo compounds, inorganic peroxides, or organic peroxides. In some embodiments, the radical initiator is Azobisisobutyronitrile (2,2'-azobis(2-methyipropionitrile), AIBN). In some embodiments, the radical initiator is 1,1'-Azobis(cyclohexanecarbonitrile) (ABCN). In some embodiments, the radical initiator is di-tert-butyl peroxide (TOOT, or DTBPB). In some embodiments, the radical initiator is benzoyl peroxide.

The contact may occur in a solvent, suitably an aprotic solvent. Solvents suitable for the reaction of the present invention include benzene, diethyl ether, toluene, tetrahydrofuran, hexane, and dichloromethane. In some preferred embodiments, the solvent is toluene or benzene, with toluene being particularly preferred.

In some embodiments, the compound having structure (III) has the following structure (IV):

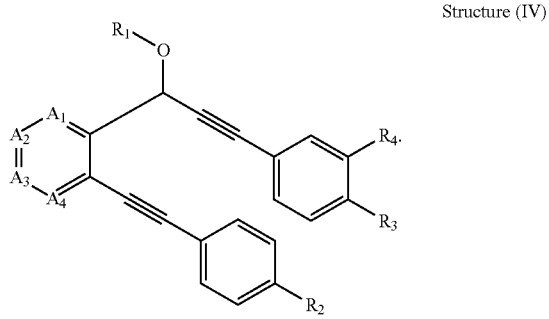

Structure (IV)

In the context of Structure (IV), A$_1$, A$_2$, A$_3$, and A$_4$ are either C—R or N, wherein at least two of A$_1$, A$_2$, A$_3$, and A$_4$ are C—R, and each R is independently selected from the group consisting of hydrogen, halogen, C$_1$-C$_6$ alkyl, and C$_1$-C$_6$ alkoxy. In some embodiments, A$_1$, A$_2$, A$_3$, and A$_4$ are each C—H. In some embodiments, A$_1$, A$_2$, A$_3$ are each C—H and D$_1$ is N.

In the context of Structure (IV), R$_1$ is selected from the group consisting of C$_1$-C$_6$ alkyl, —CH$_2$OCH$_3$, and —CH$_2$CH$_2$OCH$_3$. In some embodiments, R$_1$ is selected from the group consisting of C$_1$-C$_6$ alkyl, such as methyl, ethyl, isopropyl, n-propyl, and the like. In some embodiments, R$_1$ is methyl.

In the context of Structure (IV), R$_2$, R$_3$, and R$_4$ are each independently selected from the group consisting of hydrogen, halogen, cyano, nitro, C$_1$-C$_6$-alkyl, C$_1$-C$_6$ alkoxy, hydroxy-C$_1$-C$_6$-alkyl, halo-C$_1$-C$_6$-alkyl, cyano-C$_1$-C$_6$-alkyl, C$_1$-C$_6$-alkoxy-C$_1$-C$_6$-alkyl, C$_1$-C$_6$-alkylcarbonyl, C$_1$-C$_6$-alkoxycarbonyl, C$_1$-C$_6$-alkoxycarbonyl-C$_1$-C$_6$-alkyl, C$_3$-C$_6$-cycloalkyl, C$_3$-C$_6$-cycloalkyl-C$_1$-C$_6$-alkyl, C$_5$-C$_{10}$-cycloalkenyl, aryl, aryl-C$_1$-C$_6$-alkyl, 4- to 10-membered ring heterocyclyl, 4- to 10-membered ring heterocyclyl-C$_1$-C$_6$-alkyl, 5- to 10-membered ring heteroaryl, 5- to 10-membered ring heteroaryl-C$_1$-C$_6$-alkyl, —OR$^{104}$, —C(O)OR$^{105}$, —N(R$^{106}$)C(O)$^{107}$, —N(R$^{108}$)C(O)NR$^{109}$R$^{110}$, —S(O)$_2$R$^{111}$, —S(O)$_2$NR$^{112}$R$^{113}$, and —NS(O)$_2$NR$^{112}$R$^{113}$; wherein R$^{104}$, R$^{105}$, R$^{106}$, R$^{107}$, R$^{107}$, R$^{109}$, R$^{110}$, R$^{111}$, R$^{112}$, and R$^{113}$ are independently selected from the group consisting of hydrogen, C$_1$-C$_8$-alkyl, C$_1$-C$_8$-alkoxy, halo-C$_1$-C$_8$-alkyl, cyano-C$_1$-C$_8$-alkyl, C$_3$-C$_6$-cycloalkyl, halo-C$_3$-C$_6$-cycloalkyl, 4- to 10-membered ring heterocyclyl, 4- to 10-membered ring heterocyclyl-C$_1$-C$_8$-alkyl, aryl, haloaryl, and C$_1$-C$_8$-alkylaryl.

In some embodiments, R$_2$, R$_3$, and R$_4$ are each independently selected from the group consisting of hydrogen, methoxy, trifluoromethyl, cyano, fluoro, and n-butyl carbonyl. In some embodiments, R$_2$, R$_3$, and R$_4$ are each hydrogen. In some embodiments, R$_2$ is hydrogen, and R$_3$, and R$_4$ together with the phenyl ring to which they are bonded form a naphthalene ring.

In some embodiments, the polycyclic aromatic compound having structure (2-a) may be contacted with an acid to thereby prepare a polycyclic aromatic compound having structure (2-b):

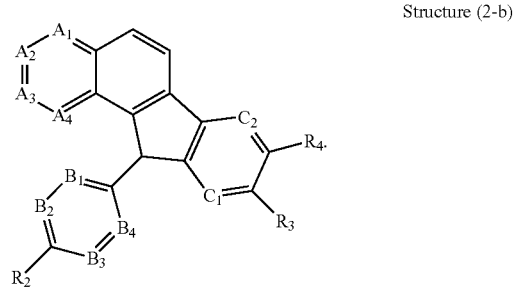

Structure (2-b)

In this embodiment, R$_1$, R$_2$, R$_3$, R$_4$, A$_1$, A$_2$, A$_3$, and A$_4$ are as defined in the context of structure (2-a). Any acid suitable for removing the stannyl functional group may be used, such as hydrochloric acid, hydrobromic acid, hydroiodic acid, nitric acid, sulfuric acid, and the like.

In some embodiments, the polycyclic aromatic compound having structure (2-a) has the following structure (2-c):

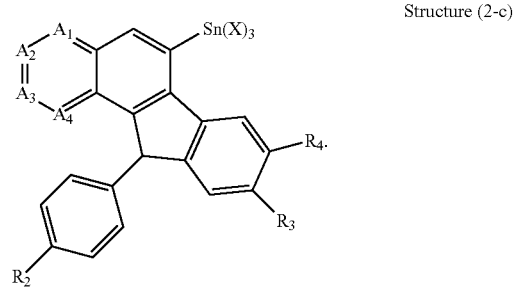

Structure (2-c)

In this embodiment, X, R$_1$, R$_2$, R$_3$, R$_4$, A$_1$, A$_2$, A$_3$, and A$_4$ are as defined in the context of structure (2-a).

In some embodiments, the polycyclic aromatic compound having structure (2-c) may be contacted with an acid to thereby prepare a polycyclic aromatic compound having structure (2-d):

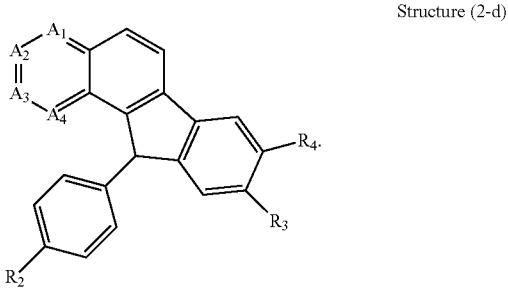

Structure (2-d)

In this embodiment, $R_1$, $R_2$, $R_3$, $R_4$, $A_1$, $A_2$, $A_3$, and $A_4$ are as defined in the context of structure (2-a). Any acid suitable for removing the stannyl functional group may be used, such as hydrochloric acid, hydrobromic acid, hydroiodic acid, nitric acid, sulfuric acid, and the like.

According to the method of the present invention, a variety of polycyclic aromatic compounds may be prepared. In some embodiments, a polycyclic aromatic compound having structure (2-a) may be selected from the group consisting of 11-H-phenyl-11H-benzo[a]fluorene, 11-H-phenyl-11H-indeno[1,2-h]quinoline, 11-H-phenyl-11H-indeno[1,2-h]isoquinoline, 11-H-phenyl-11H-indeno[2,1-f]isoquinoline, and 11-H-phenyl-11H-indeno[2,1-h]quinolone, each of which is substituted or unsubstituted.

In some embodiments of the present invention, the polycyclic aromatic compound having structure (2-a) may be contacted with iodine to thereby prepare a polycyclic aromatic compound having structure (2-e):

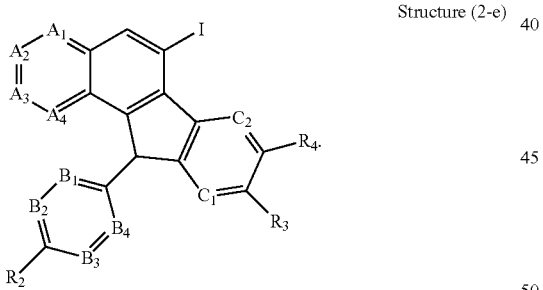

Structure (2-e)

In this embodiment, $R_1$, $R_2$, $R_3$, $R_4$, $A_1$, $A_2$, $A_3$, $A_4$, $B_1$, $B_2$, $B_3$, $B_4$, $C_1$, and $C_2$ are as defined in the context of structure (2-a). The compound of structure (2-e) may be further derivatized at the locus of the iodine atom in order to incorporate functional groups on the polycyclic aromatic compound.

In some embodiments, the present invention is directed to a method of preparing a 11-phenyl-11H-benzo[a]fluorene. In a first step, the method comprises contacting a 1-(2-ethynylphenyl)propargyl alkyl ether with a stannane compound in the presence of a radical initiator, wherein said contact of the 1-(2-ethynylphenyl)propargyl alkyl ether with the stannane compound initiates a cascade reaction that yields a stannyl-11-phenyl-11H-benzo[a]fluorene.

In a second step, the method comprises contacting the stannyl-11-phenyl-11H-benzo[a]fluorene with an acid to thereby prepare the 11-phenyl-11H-benzo[a]fluorene, wherein the 11-phenyl-11H-benzo[a]fluorene is substituted or unsubstituted.

In some embodiments, the stannane compound has a general formula $X_3SnH$, wherein X is a $C_1$-$C_6$ alkyl or phenyl. In some embodiments, the stannane compound is selected from the group consisting of trimethyl stannane, triethyl stannane, tri(n-propyl)stannane, tri(isopropyl)stannane, tri(n-butyl)stannane, tri(isobutyl)stannane, triphenyl stannane, and any combination there. The identity of X in structure (1-g) is determined primarily, if not wholly, by the stannane compound. In some preferred embodiments, the stannane compound is tri(n-butyl)stannane.

In some embodiments, the radical initiator is any compound that can provide radicals for the initiation step of a radical chain reaction. In some embodiments, the radical initiator is any compound that converts the stannane compound (generally, $X_3SnH$, wherein X is a $C_1$-$C_6$ alkyl or phenyl) into $X_3Sn$ radical. Suitable radical initiators include azo compounds, inorganic peroxides, or organic peroxides. In some embodiments, the radical initiator is Azobisisobutyronitrile (2,2'-azobis(2-methylpropionitrile), AIBN). In some embodiments, the radical initiator is 1,1'-Azobis(cyclohexanecarbonitrile) (ABCN). In some embodiments, the radical initiator is di-tert-butyl peroxide (TOOT, or DTBPB). In some embodiments, the radical initiator is benzoyl peroxide.

The contact may occur in a solvent, suitably an aprotic solvent. Solvents suitable for the reaction of the present invention include benzene, diethyl ether, toluene, tetrahydrofuran, hexane, and dichloromethane. In some preferred embodiments, the solvent is toluene or benzene, with toluene being particularly preferred.

Any acid suitable for removing the stannyl functional group may be used, such as hydrochloric acid, hydrobromic acid, hydroiodic acid, nitric acid, sulfuric acid, and the like.

In some embodiments, the 1-(2-ethynylphenyl)propargyl alkyl ether has the following general structure (V):

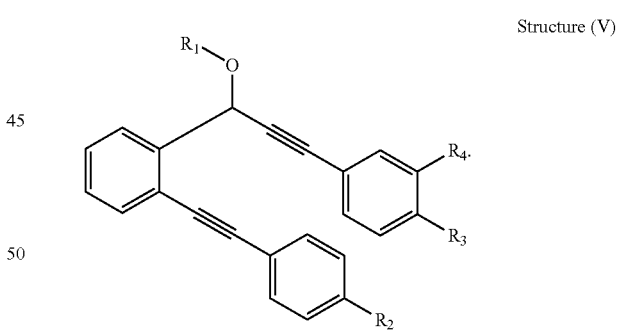

Structure (V)

In the context of Structure (V), $R_1$ is selected from the group consisting of $C_1$-$C_6$ alkyl, —$CH_2OCH_3$, and —$CH_2CH_2OCH_3$. In some embodiments, $R_1$ is selected from the group consisting of $C_1$-$C_6$ alkyl, such as methyl, ethyl, isopropyl, n-propyl, and the like. In some embodiments, $R_1$ is methyl.

In the context of Structure (V), $R_2$, $R_3$, and $R_4$ are each independently selected from the group consisting of hydrogen, halogen, cyano, nitro, $C_1$-$C_6$-alkyl, $C_1$-$C_6$ alkoxy, hydroxy-$C_1$-$C_6$-alkyl, halo-$C_1$-$C_6$-alkyl, cyano-$C_1$-$C_6$-alkyl, $C_1$-$C_6$-alkoxy-$C_1$-$C_6$-alkyl, $C_1$-$C_6$-alkylcarbonyl, $C_1$-$C_6$-alkoxycarbonyl, $C_1$-$C_6$-alkoxycarbonyl-$C_1$-$C_6$-alkyl, $C_3$-$C_6$-cycloalkyl, $C_3$-$C_6$-cycloalkyl-$C_1$-$C_6$-alkyl, $C_5$-$C_{10}$- cycloalkenyl, aryl, aryl-$C_1$-$C_6$-alkyl, 4- to 10-membered ring heterocyclyl, 4- to 10-membered ring heterocyclyl-$C_1$-$C_6$-alkyl, 5- to 10-membered ring heteroaryl, 5- to 10-membered ring heteroaryl-$C_1$-$C_6$-alkyl, —$OR^{104}$, —$C(O)OR^{105}$, —$N(R^{106})C(O)R^{107}$, —$N(R^{108})C(O)NR^{109}R^{110}$, —$S(O)_2R^{111}$, —$S(O)_2NR^{112}R^{113}$, and —$NS(O)_2NR^{112}R^{113}$; wherein $R^{104}$, $R^{105}$, $R^{106}$, $R^{107}$, $R^{107}$, $R^{109}$, $R^{110}$, $R^{111}$, $R^{112}$, and $R^{113}$ are independently selected from the group consisting of hydrogen, $C_1$-$C_8$-alkyl, $C_1$-$C_8$-alkoxy, halo-$C_1$-$C_8$-alkyl, cyano-$C_1$-$C_8$-alkyl, $C_3$-$C_6$-cycloalkyl, halo-$C_3$-$C_6$-cycloalkyl, 4- to 10-membered ring heterocyclyl, 4- to 10-membered ring heterocyclyl-$C_1$-$C_8$-alkyl, aryl, haloaryl, and $C_1$-$C_8$-alkylaryl.

In some embodiments, $R_2$, $R_3$, and $R_4$ are each independently selected from the group consisting of hydrogen, methoxy, trifluoromethyl, cyano, fluoro, and n-butyl carbonyl. In some embodiments, $R_2$, $R_3$, and $R_4$ are each hydrogen. In some embodiments, $R_2$ is hydrogen, and $R_3$, and $R_4$ together with the phenyl ring to which they are bonded form a naphthalene ring.

In some embodiments, the stannyl-11-phenyl-11H-benzo[a]fluorene has the following structure (3-a):

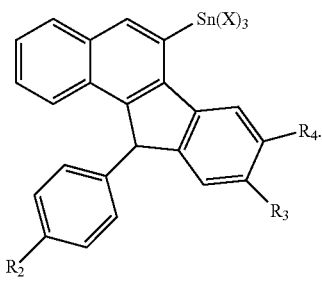

Structure (3-a)

In the context of Structure (3-a), X is a $C_1$-$C_6$ alkyl or phenyl, and $R_2$, $R_3$, and $R_4$ are as defined the context of structure (V).

In some embodiments, $R_2$, $R_3$, and $R_4$ are each independently selected from the group consisting of hydrogen, methoxy, trifluoromethyl, cyano, fluoro, and n-butyl carbonyl. In some embodiments, $R_2$, $R_3$, and $R_4$ are each hydrogen. In some embodiments, $R_2$ is hydrogen, and $R_3$, and $R_4$ together with the phenyl ring to which they are bonded form a naphthalene ring.

In some embodiments, the stannyl-11-phenyl-11H-benzo[a]fluorene having the structure (3-a) is contacted with the acid to thereby prepare a 11-phenyl-11H-benzo[a]fluorene having structure (3-b):

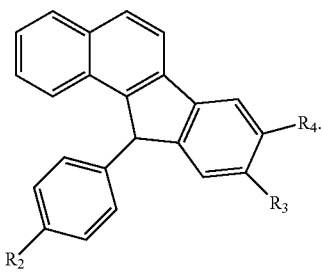

Structure (3-b)

In the context of Structure (3-a), X is a $C_1$-$C_6$ alkyl or phenyl, and $R_2$, $R_3$, and $R_4$ are as defined the context of structure (V).

In some embodiments, $R_2$, $R_3$, and $R_4$ are each independently selected from the group consisting of hydrogen, methoxy, trifluoromethyl, cyano, fluoro, and n-butyl carbonyl. In some embodiments, $R_2$, $R_3$, and $R_4$ are each hydrogen. In some embodiments, $R_2$ is hydrogen, and $R_3$, and $R_4$ together with the phenyl ring to which they are bonded form a naphthalene ring.

III. RESULTS

In an exemplary, non-limiting embodiment, several starting 1,(2-alkynylphenyl)propargyl methyl ethers 1 are readily prepared from commercially available 2-bromobenzaldehydes via a combination of Sonogashira cross-coupling and nucleophilic addition of acetylide anions to the aldehyde. See Table 1. The lithiated alkoxide formed at the latter step can be converted either into a propargylic alcohol via protonation or into propargyl methyl ethers via in situ addition of iodomethane. The 1,(2-alkynylphenyl)propargyl methyl ethers 1 were synthesized with a variety of substituents on rings A, B, and C and in good yields (55-90%).

TABLE 1

1-(2-alkynylphenyl)propargyl methyl ethers

[Reaction scheme: 2-bromobenzaldehyde + HC≡C—R with $Pd(PPh_3)_2Cl_2$, CuI, $Et_3N$, r.t., 12 h → 2-alkynylbenzaldehyde; then a) Li—C≡C—$R^1$, b) MeI, THF, −78° C., 12 h → product]

R = Ph

1a
R, $R^1$ = Ph

1b
[structure with MeO substituent]

1c
[structure with two MeO substituents]

TABLE 1-continued
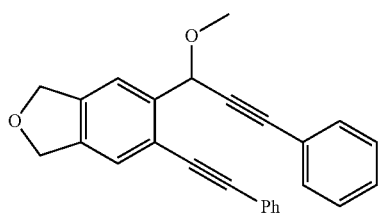 [SMILES: COC(C#Cc1ccccc1)c1cc2c(cc1C#Cc1ccccc1)COC2] 1d
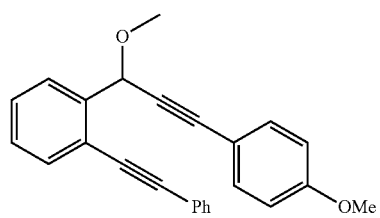 [SMILES: COc1ccc(C#CC(OC)c2ccccc2C#Cc2ccccc2)cc1] 1e
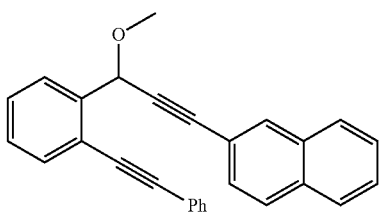 [SMILES: COC(C#Cc1ccc2ccccc2c1)c1ccccc1C#Cc1ccccc1] 1f
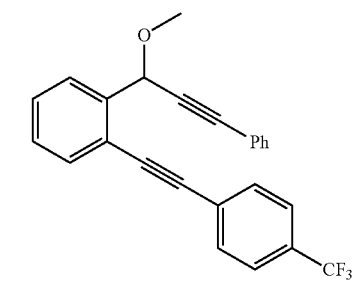 [SMILES: COC(C#Cc1ccccc1)c1ccccc1C#Cc1ccc(C(F)(F)F)cc1] 1g
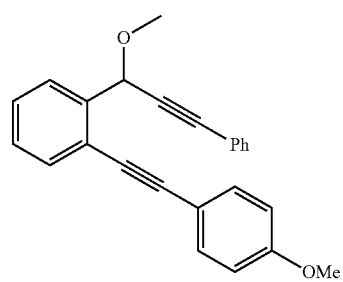 [SMILES: COc1ccc(C#Cc2ccccc2C(C#Cc2ccccc2)OC)cc1] 1h
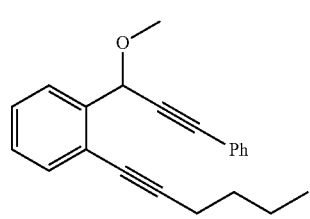 [SMILES: CCCCC#Cc1ccccc1C(C#Cc1ccccc1)OC] 1i
TABLE 1-continued
 1j
 1k
 1l
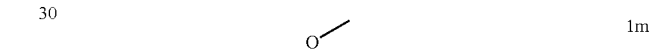 1m
 1n
 1o
 1p

TABLE 1-continued

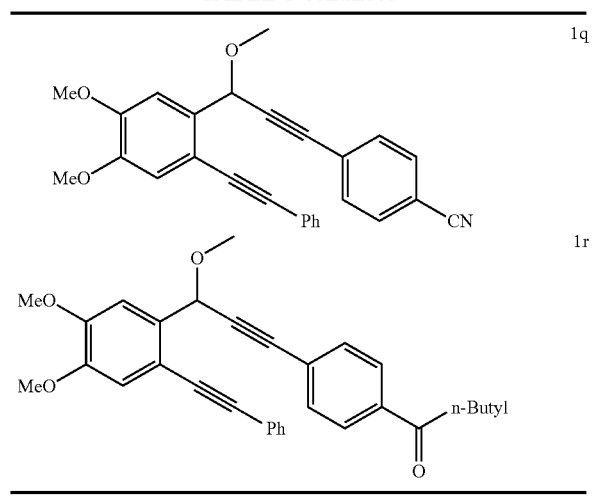

1q

1r

Table 2 shows screening of various radical reagents and initiators for the model transformation of 1a to 2a. The combination of Bu₃SnH and AIBN in refluxing toluene was the most efficient. The failure of silicon reagents indicates that a suitable organotin radical precursor was essential for the success of this cascade.

TABLE 2

Optimization of reaction conditions

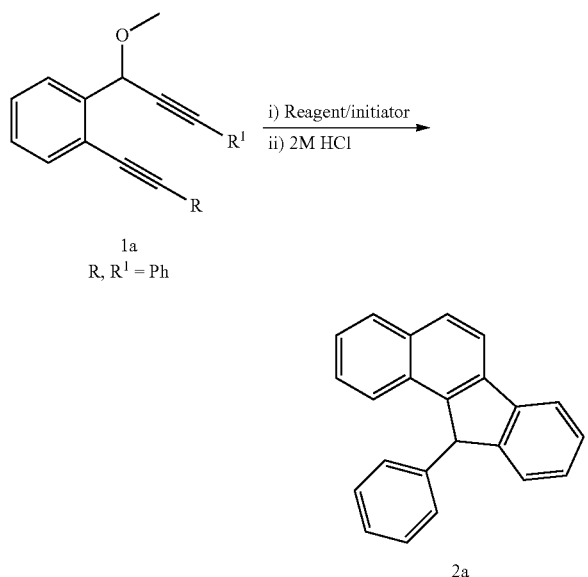

| Entry | Reagent/initiator[a] | Condition | Yield[b] |
|---|---|---|---|
| 1 | Bu₃SnH/AIBN | Benzene, 16 h, 80° C. | 65% |
| 2 | Et₃SiH/AIBN | Benzene, 16 h, 80° C. | —[c] |
| 3 | Et₃SiH/AIBN | Toluene, 14 h, 110° C. | —[d] |
| 4 | Bu₃SnH/AIBN | Toluene, 14 h, 110° C. | 86% |
| 5 | Ph₃SnH/AIBN | Toluene, 14 h, 110° C. | 40% |
| 6 | Bu₃SnH/ABCN | Toluene, 14 h, 100° C. | 60% |
| 7 | Bu₃SnH/DTBPB | Toluene, 14 h, 100° C. | 40% |
| 8 | Et₃B/Bu₃SnH | THF, 12 h, rt | —[e] |
| 9 | Et₃B/Bu₃SnH | Benzene, 14 h, 70° C. | —[f] |

[a]1.3 equiv of reagent and 0.4 equiv initiator,
[b]Isolated yields from silica chromatography,
[c-f]Unreacted starting material (60%, 30%, 65%, and 75% respectively) and complex mixture of products The reaction conditions were further optimized by changing molar ratios of Bu₃SnH/AIBN and varying flow rate using a syringe pump. See Table 3. We found that maintaining steady concentration of AIBN is preferred over the addition of initiator at once in the beginning of reaction. The addition of 0.04M Bu₃SnH/0.01M AIBN mixture at the flow rate of 1 mL/hr to the 0.03M solution of substrate in toluene (110° C., 14 h) provided 2a in excellent (86%) yield. Use of lower amounts of Bu₃SnH/AIBN led to incomplete conversions.

TABLE 3

Further Optimization of Bu₃Sn-Addition to Alkyne 1a

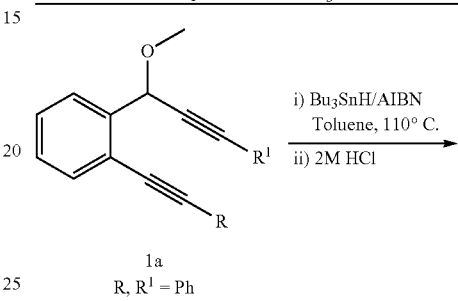

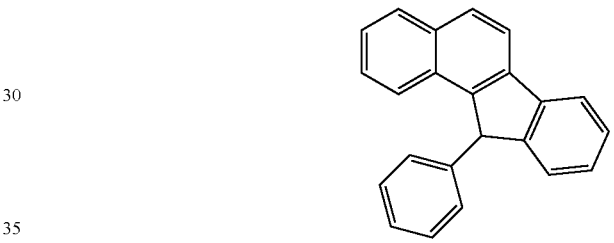

| Entry | AIBN[a] (eq) | Bu₃SnH (eq) | Rate | Conversion | Yield[b] |
|---|---|---|---|---|---|
| 1 | 1 | 1 | all at once[c] | 60% | 40% |
| 2 | 1 | 2 | all at once | 70% | 60% |
| 3 | 1 | 1.5 | AIBN at once, Bu₃SnH 2 mL/hr | 80% | 70% |
| 4 | 0.5 | 1.5 | Bu₃SnH + AIBN, 2 mL/hr[d] | 100% | 76% |
| 5 | 0.5 | 1.5 | Bu₃SnH + AIBN, 1 mL/hr | 100% | 86% |
| 6 | 0.4 | 1.3 | Bu₃SnH + AIBN, 1 mL/hr | 100% | 86% |
| 7 | 0.2 | 1.5 | Bu₃SnH + AIBN, 1 mL/hr | 60% | 50% |

[a]Equivalents are based on proportion to starting material,
[b]Isolated yields after column chromatography,
[c]Total concentration 0.03M,
[d]Condition A: AIBN and Bu3SnH were dissolved in 2 mL toluene together. Condition B: AIBN and Bu3SnH were dissolved separately and added simultaneously. Condition A and B showed no change in yield (all reactions performed under argon atmosphere)

The scope of this reaction was verified by the successful cascade cyclization of propargyl methyl ethers shown in Table 4. The range of substituents includes donor and acceptor groups in the core benzene ring as well as at the both alkyne termini. As the result, selective introduction of substituents of varying electronic nature at specific positions of rings A, B, and C (Table 4) of the polycyclic product is possible. Although reaction conditions were not optimized for each of the substrates 2b-2r, the isolated yields remained consistently high for both the donor and the acceptor substituents (70-88%), indicating generality and robustness of this cascade transformation.

TABLE 4
Radical Cascade of Propargyl Methyl Ethers
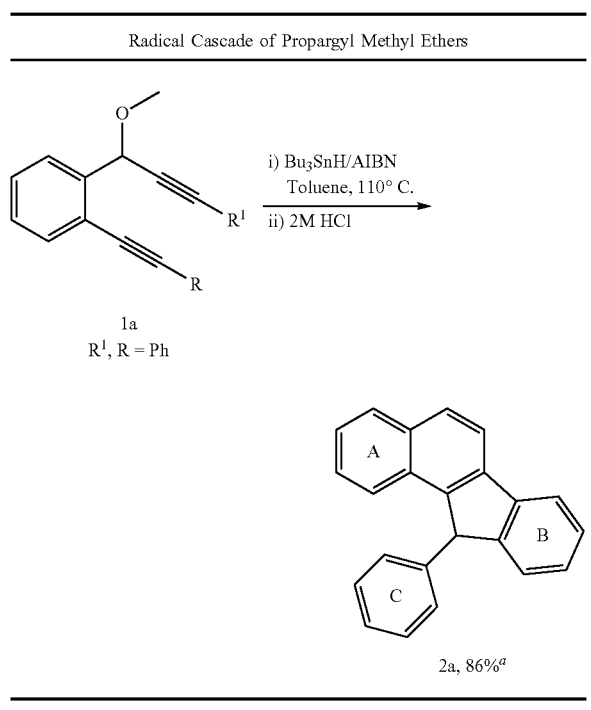
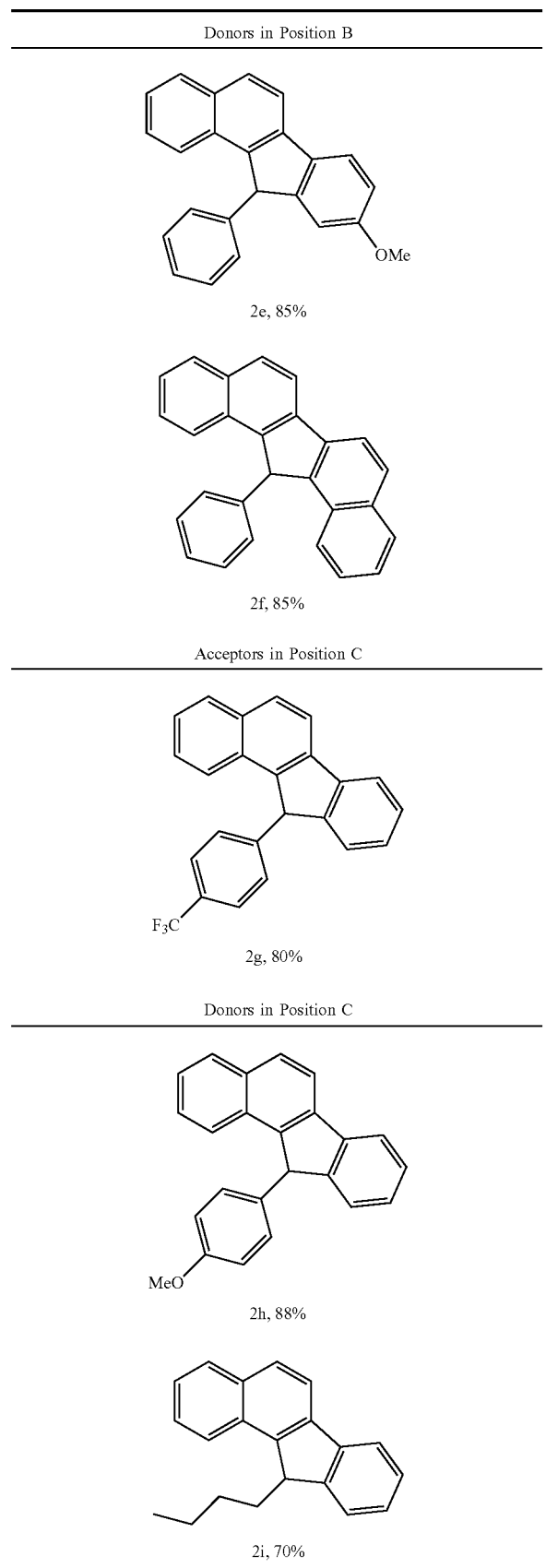

TABLE 4-continued

Acceptors in Position A 2j, 70%

2k, 71%

2l, 80%

2m, 78%

Acceptors in Position B 2n, 73%

2o, 72%

2p, 72%

Donor and Acceptor Combination 2q, 80%

2r, 76%

[a]Isolated yields after column chromatography

Figure 4:
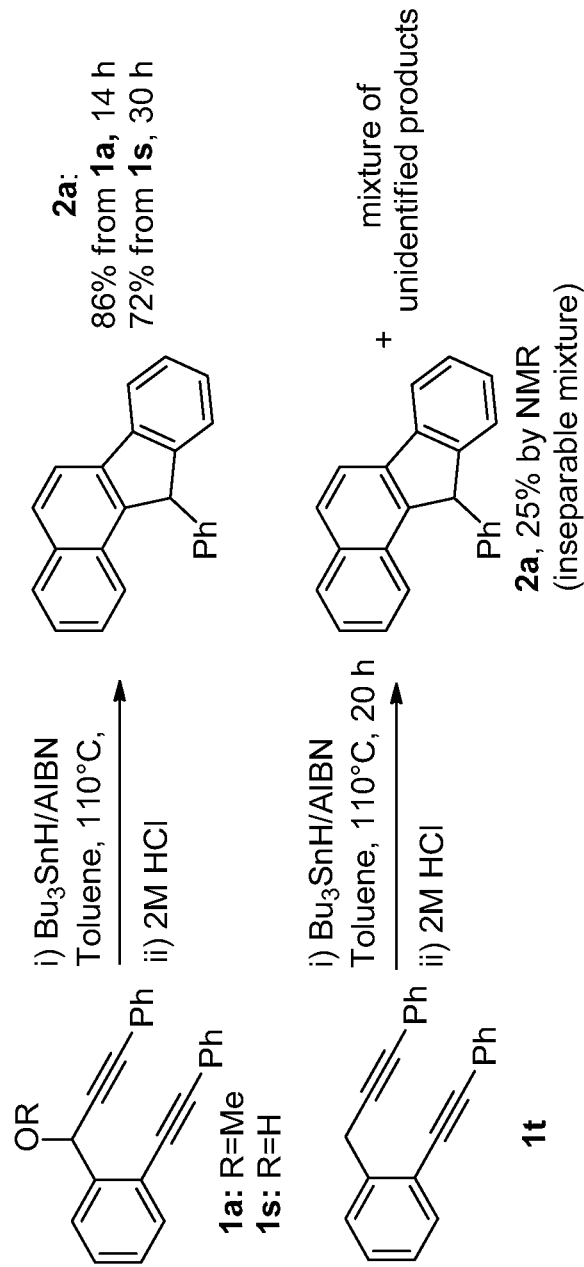
FIG. 4 illustrates control experiments, specifically, the effect of propargylic substitution on selectivity.

To examine the role of the methoxy substituent in the radical cascade, two alternate substrates were prepared: a free propargyl alcohol 1s and a "deoxygenated" analogue with an unsubstituted methylene bridge 1t (synthesis of these compounds is described in the Examples). Even though the reaction of the free alcohol was noticeably slower than the reaction of propargylic ether 1a, it still displayed comparable level of selectivity, providing an attractive synthetic alternative to the reactions of OMe-substituted substrates. On the other hand, the reaction of the "deoxygenated" substrate 1t is significantly less selective. See FIG. 4, which illustrates control experiments, specifically, the effect of propargylic substitution on selectivity. Yields and reaction times for these experiments suggest that the presence of the oxygen substituent plays an important role in the selectivity of this cascade reaction.

IV. STRUCTURE DETERMINATION

Structures of the products were determined by the combination of $^1$H and $^{13}$C NMR spectroscopy, which was complemented, in selected cases, by X-ray crystallography. (CCDC-1015545 (for 2a), CCDC-1013214 (for 2p) and CCDC-1013215 (for 2u). These data can be obtained free of charge from The Cambridge Crystallographic Data Center via www.ccdc.cam.ac.uk/data_request/cif.) The characteristic $^1$H NMR features include disappearance of the reactants' OCH$_3$ and the propargylic H peaks (at 3.5-3.7 and 5.3-5.9 ppm, respectively) to give rise to a 5.1-5.8 ppm singlet for the remaining sp$^3$ C—H in the products. In $^{13}$C NMR, disappearance of the OCH$_3$ (56-58 ppm), propargylic CH (71-73 ppm), and the four alkynyl carbons (84-92 ppm) along with the appearance of a signal at 52-55 ppm for the sp$^3$ carbon in the partially reduced five-membered ring indicated completion of the cascade.

Figure 5:
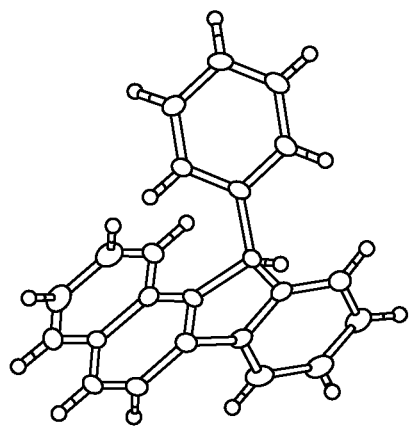

The naphthalene and phenylene moieties in the benzofluorene skeleton of 11-phenyl-11H-benzo[a]fluorene 2a are approximately coplanar suggesting that efficient conjugation and electronic communication should be possible between the different parts of the molecule. On the other hand, the exocyclic aryl group is projected away from the polycyclic plane and oriented in a way that minimizes steric repulsion with the aromatic hydrogens. See FIG. 5, which is the ORTEP diagram for 2a.

Figure 6:
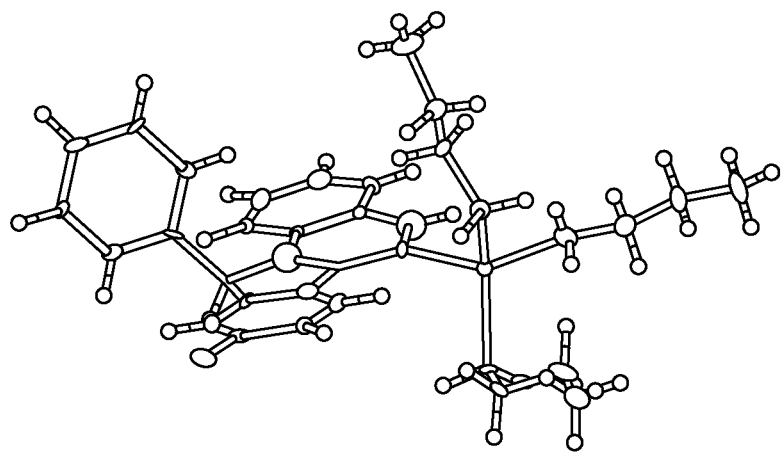
FIG. 6 is the ORTEP diagram for 2p-Sn.

Chemo- and regioselectivity of Sn addition was confirmed by X-ray analysis of Sn-precursor of 14-fluoro-11-phenyl-11H-benzo[a]fluorene 2p-Sn. See FIG. 6, which is the ORTEP diagram for 2p-Sn. As expected, the Sn atom has approximately tetrahedral geometry with connections to one sp$^2$ and three sp$^3$ carbon atoms. Surprisingly, the average of Sn—C$_{sp3}$ bond lengths (2.163 Å) is smaller than the Sn—C$_{sp2}$ distance (2.171 Å). For example, the average bond length of the Sn—C$_{sp2}$ bonds in triphenyltin 2-pyrimidylthioylacetate is 2.123 Å. Weng Ng, S.; Kumar Das, V. G.; Yip, W. H.; Mak, T. C. W. *J. Chem. Crystal.* 1993, 23, 441. The anomalously long bond length in the latter case can be attributed to the steric repulsion between the bulky Bu$_3$Sn group and ortho-hydrogens of the polycyclic moiety. Furthermore, the steric clash of the butyl groups and the polycyclic structure leads to the deviation of C—Sn—C angles (106.93° to 114.96°) from the ideal 109.5° tetrahedral valence angle and the slight (~6°) deviation of Sn atom from the benzo[a]fluorene plane.

V. COMPUTATIONAL DETAILS

The computational analysis of potential energy profiles involved in this multistep transformation was performed in Gaussian 09 with unrestricted M06-2X functional due to its relatively accurate description of reaction and activation energies for a variety of chemical processes including radical reactions. See Frisch, M. J. et. al. *Gaussian 09, Revision B*.01; Gaussian: Wallingford, C T, 2009; Zhao, Y.; Truhlar, D. G. *Theor. Chem. Acc.* 2008, 120, 215; Zhao, Y.; Truhlar, D. G. *Acc. Chem. Res.* 2008, 41, 157; and Zhao, Y.; Truhlar, D. G. *J. Phys. Chem. A* 2008, 112, 1095. The LanL2DZ basis set was used for Sn. Chemcraft 1.7 and CYLView were used to render the molecules and orbitals. See http://www.chemcraftprog.com and CYLview, 1.0b; Legault, C. Y., Université de Sherbrooke, 2009 (http://www.cylview.org). Frequency calculations were performed to confirm each stationary point as either a minimum or a first-order saddle point. NBO 3.0 program was used to analyze electronic properties of reactive intermediates. See Reed, A. E.; Weinhold, F. *J. Chem. Phys.* 1985, 83, 1736. Reed, A. E.; Weinhold, F. *Isr. J. Chem.* 1991, 31, 277. Reed, A. E.; Curtiss, L. A.; Weinhold, F. *Chem. Rev.* 1988, 88, 899. Weinhold F. in Schleyer P.v.R. Ed. Encyclopedia of Computational Chemistry: Wiley: New-York, 1998, 3, 1792.

VI. CHEMOSELECTIVITY IN RADICAL CASCADES

Figure 7:
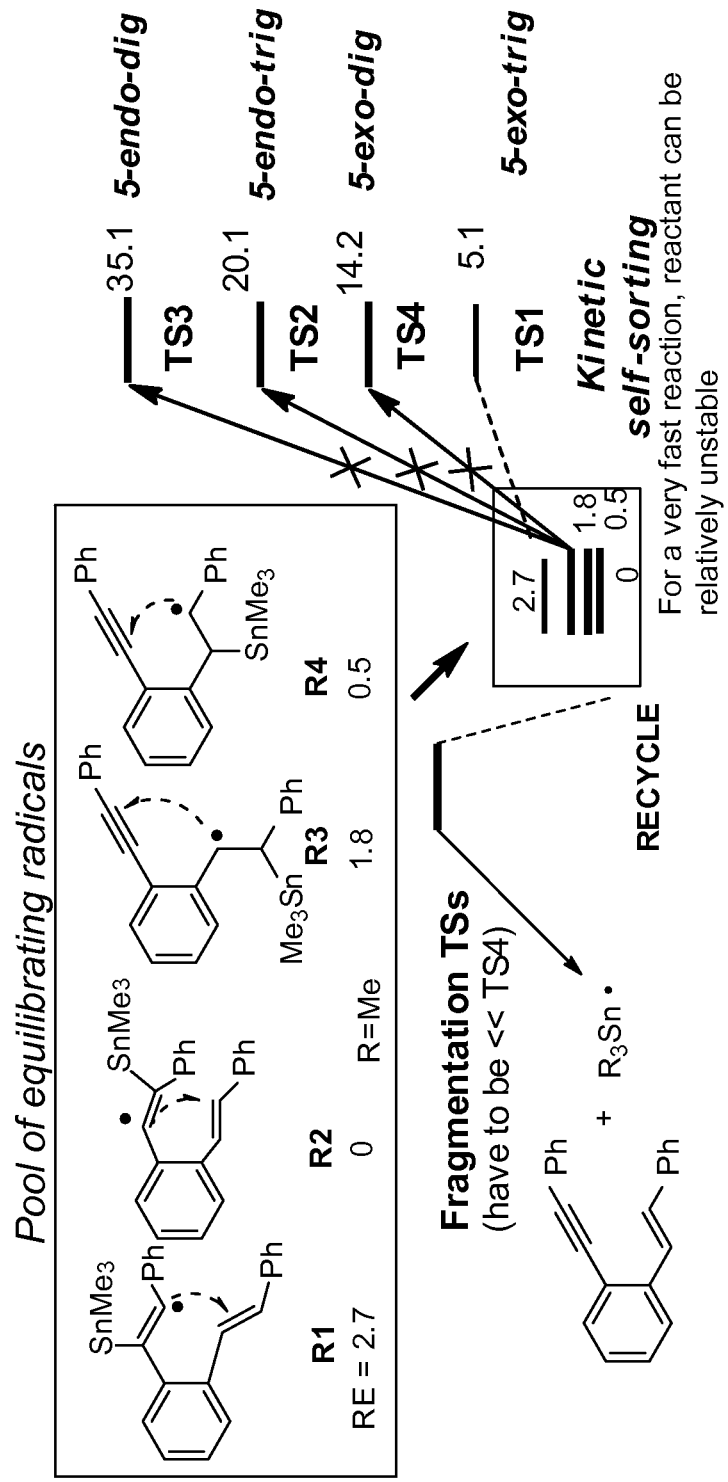
FIG. 7 is a drawing illustrating the proposed radical pool concept for the cyclization of conjugated enynes.

Chemoselectivity is a key challenge in the design of cascade transformations of multifunctional substrates. In a system, where functional groups are similar or almost identical (i.e., oligoalkynes), such challenge is especially formidable. We had shown earlier that a new application of dynamic covalent chemistry towards reversible radical reactions of Sn-radicals and π-systems can be used for the design of surprisingly selective transformation. See a) Mondal, S.; Mohamed, R. K.; Manoharan, M.; Phan, H.; Alabugin, I. V. *Org. Lett.*, 2013, 15, 5650. b) Mondal, S.; Gold, B.; Mohamed, R. K.; Alabugin, I. V. *Chem. Eur. J.*, 2014, 20, 8664. c) Mondal, S.; Gold, B.; Mohamed, R.; Phan, H.; Alabugin, I. V. *J. Org. Chem.*, 2014, 79, 7491. For example, in reactions of aromatic enynes (FIG. 7) where an intermolecular radical attack can lead to the formation of four different benzylic radicals (each capable of two cyclizations), we observed the formation of a single product out of the 8 possible cyclic structures. The preferred product is formed from the attack of the most reactive (vinyl) radical at the most reactive (alkene) i-bonds via the most stereoelectronically favorable (exo) path. Assuming that the radicals can equilibrate prior to the cyclization, this process can be characterized as a kinetic self-sorting of a pool of the four equilibrating radicals via reaction with the lowest activation barrier. In accord with the Curtin-Hammett principle, under the conditions where addition of Sn-radicals is reversible, it is not the relative stability of radicals but the absolute energies of the respective cyclization transition states that matter.

The equilibrium between vinyl radicals is supported by the literature reports confirming that addition of vinyl stannanes to double bonds is reversible. See (a) Neumann, W. P.; Albert, H. J.; Kaiser, W. *Tetrahedron Lett.* 1967, 2041. (b) Kuivila, H. G.; Sommer, R. *J. Am. Chem. Soc.* 1967, 89, 5616. (c) Leusink, A. J.; Budding, H. A.; Drenth, W. *J. Organomet. Chem.* 1968, 11, 541. (d) Chatgilialoglu, C.; Ballestri, M.; Ferreri, C.; Vecchi, D. *J. Org. Chem.*, 1995, 60, 3826. For example, Sn radicals are known to isomerize alkenes fast and much faster than Si-based radicals. However, at this point, the "radical pool" is a hypothetical model to fit the observed results.

Alternatively, a simpler source of selectivity can be found in a kinetic preference for the Sn-radical attack at the propargylic position. Such attack would directly provide the correct radical, positioned properly for initiating the cascade. In order to test for applicability of the two models to the present system, we evaluated the relative reactivity of the two types of substituted alkynes separately by carrying out an intermolecular competition experiment between propargyl ether 3 and the diaryl alkyne 4 to determine the relative reactivity of these functionalities towards Bu$_3$SnH/AIBN system.

Figure 8:
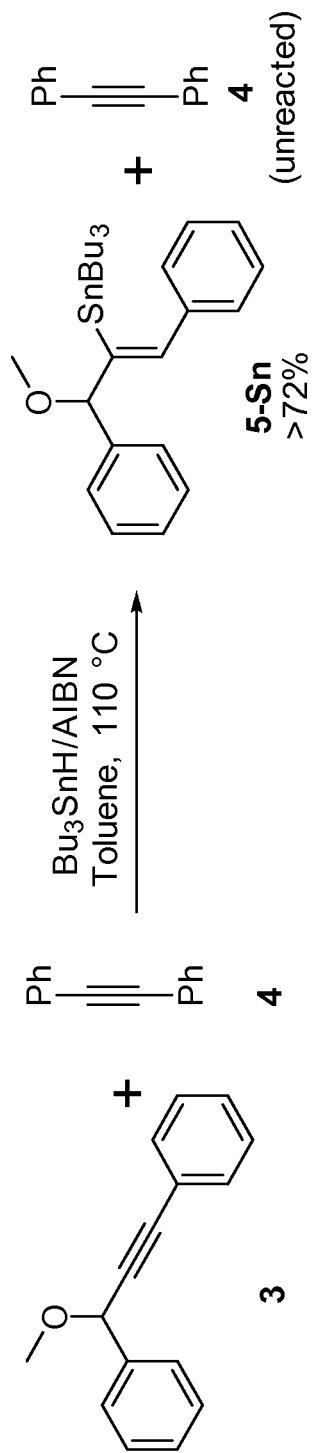
FIG. 8 illustrates intermolecular competition in radical hydrostannation of alkynes-propargylic ether 3 vs. diphenyl acetylene (tolane) 4.

FIG. 8 illustrates intermolecular competition in radical hydrostannation of alkynes-propargylic ether 3 vs. diphenyl acetylene (tolane) 4. FIG. 8 summarizes competition experiments for the 1:1 ratio mixture of propargylic ether 3 and diphenyl acetylene 4 at the previously optimized cyclization conditions. Whereas the propargylic ether was completely consumed, tolane 4 remained unreacted. The simplest rationale for these experimental result is that the presence of the propargylic methoxy substituent directs Sn addition by accelerating kinetic attack at the adjacent alkyne carbon. A priori, one can also suggest that the both alkynes undergo fast and reversible Sn-addition but vinyl radicals produced from the propargylic ether 3 are intercepted via H-abstraction faster.

Figure 9:
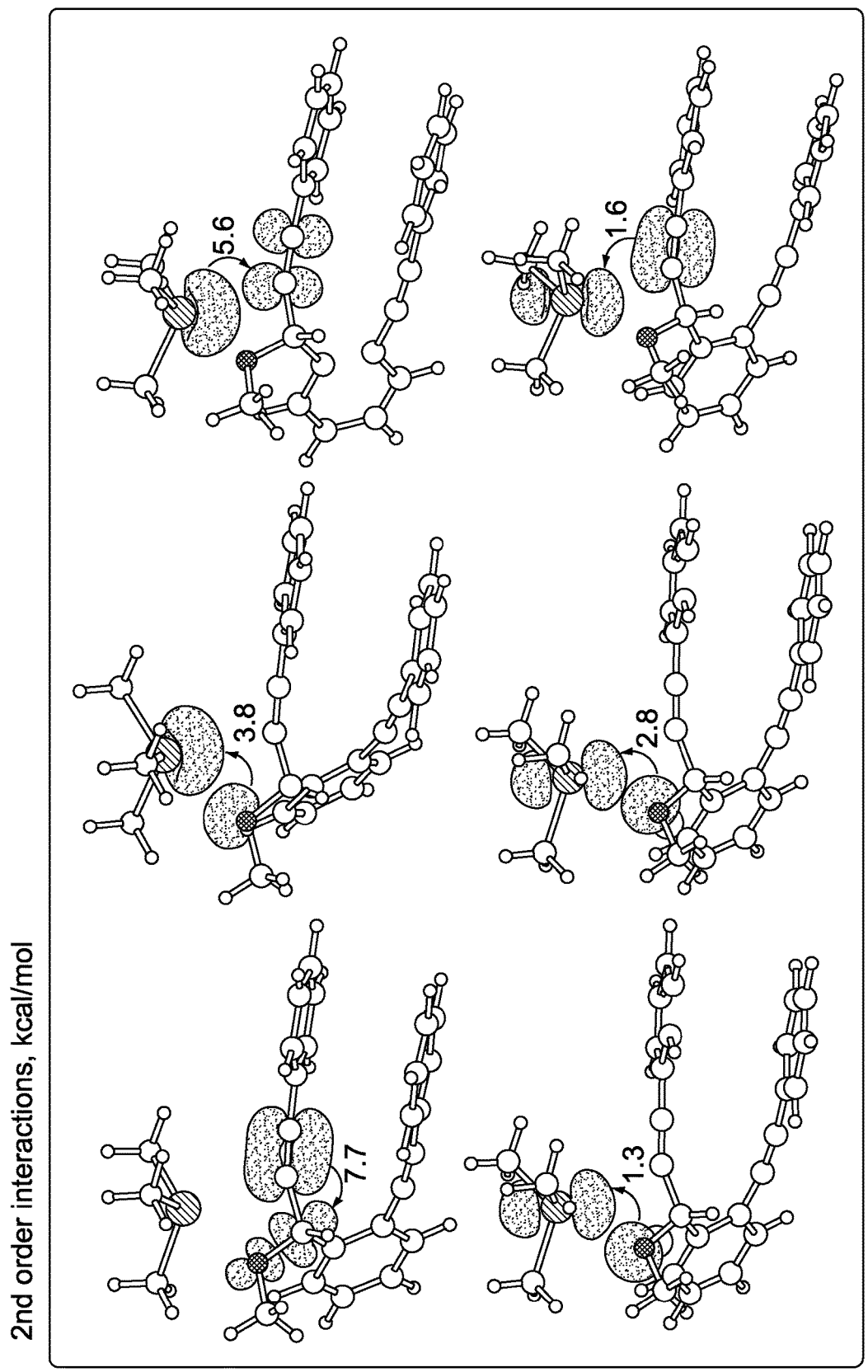
FIG. 9 is a drawing depicting selected electronic interactions (NBO analysis in kcal/mol) contributing to the structure and stability of the transition state of the Me$_3$Sn radical addition to the bis-alkyne 1a to form the most stable radical A. Note that the radical center ($n_{Sn}$) is half occupied and, unlike a lone pair, can serve as either a donor or an acceptor in $2^{nd}$ order delocalizing interactions Top left: ($\alpha$- and $\beta$-spins summed) $\pi_{C=C} \rightarrow \sigma^*_{C-O}$; Top center: ($\alpha$-spin) $sp^{1.12}$ $n_O \rightarrow n_{Sn}$; Top right: ($\alpha$-spin) $n^*_{Sn} \rightarrow \pi^*_{C=C}$. This interaction is responsible for the formation of Sn—C bond. Bottom left: ($\beta$-spin) $sp^{3.67}$ $n_O \rightarrow n_{Sn}$; Bottom center: ($\beta$-spin) $sp^{3.07}$ $n_O \rightarrow n_{Sn}$; Bottom right: ($\beta$-spin) $\pi_{C=C} \rightarrow n_{Sn}$.

Guided by these results, we found that the calculated barrier for $SnMe_3$ radical addition at the propagylic position is remarkably low: $\Delta G^*(110°\ C.) = 4.2$ kcal/mol. The relatively low energy of the TS can be rationalized by the several interactions between oxygen lone pairs, the π system and the Sn radical as illustrated by the NBO energies in FIG. 9, which is a drawing depicting selected electronic interactions (NBO analysis in kcal/mol) contributing to the structure and stability of the transition state of the $Me_3Sn$ radical addition to the bis-alkyne 1a to form the most stable radical A. Note that the radical center ($n_{Sn}$) is half occupied and, unlike a lone pair, can serve as either a donor or an acceptor in $2^{nd}$ order delocalizing interactions Top left: (α- and β-spins summed) $\pi_{C-C} \to \sigma^*_{C-O}$; Top center: (α-spin) $sp^{1.12}$ $n_O \to n_{Sn}$; Top right: (α-spin) $n^*_{Sn} \to \pi^*_{C-C}$. This interaction is responsible for the formation of Sn—C bond. Bottom left: (β-spin) $sp^{3.67}$ $n_O \to n_{Sn}$; Bottom center: (β-spin) $sp^{3.07}$ $n_O \to n_{Sn}$; Bottom right: (β-spin) $\pi_{C-C} \to n_{Sn}$. Such Transition State stabilization derives, at least partially, from unusual three-electron interactions between the lone-pair of oxygen and the radical orbital at Sn to guide radical attack at the required position.

To better understand the thermodynamic landscape, we also compared the relative stabilities of the four vinyl radicals that can be formed from the skipped diyne 1a and $R_3Sn$ radical. Furthermore, we had also considered the fifth possibility—formation of a 2c,3e bond between the radical and the oxygen's lone pair but these species did not correspond to the separate energy minimum and converged to the most stable vinyl radical A without barrier. Both ΔE and ΔG (taking the energy of the separated enediyne and the $SnR_3$ radical as the reference point) were calculated for the four intermediates A, B, C, and D (using a truncated, $Me_3Sn$ substituent). In this system, the radical intermediate leading to the experimentally observed pathway was found to be significantly more stable than the other vinyl radicals in FIG. 10, which is a drawing illustrating relative free energies of the four vinyl radicals formed by radical attack at the triple bonds of the skipped enediyne 1a at 110° C. This difference in stability originates from a combination of several factors. First, the two more stable radicals (A and D) enjoy benzylic stabilization. However, efficiency of benzylic resonance can be attenuated by steric effects. Furthermore, other electronic effects can also offer significant stabilization and complicate the overall situation. For example, the only non-benzylic radical (B) is, somewhat surprisingly, more stable than radical C. This inversion of stability may be at least partially derived from the captodative stabilization of the radical center by a vicinal acceptor (C—O) and a vicinal donor (C—Sn) bonds flanking radical B.

FIGS. 11A, 11B, 11C, and 11D depict the calculated geometries of the four vinyl radicals A (FIG. 11A), B (FIG. 11B), C (FIG. 11C), and D (FIG. 11D) at UM06-2X/ LanL2DZ level of theory. In all four radicals, the vicinal C—Sn bond is aligned with the radical orbital in order to maximize stabilizing hyperconjugative interaction with the radical. Despite a literature suggestion that this interaction is unimportant, NBO analysis find this interaction to the strongest among the interactions of $\sigma_{Sn-C}$ with the vicinal orbitals. See Dimopoulos, P.; George, J.; Tocher, D. A.; Manaviazar, S.; Hale, K. *J. Org. Lett.* 2005, 7, 5377. Although this interaction is common for all four species and can be neglected in the discussion of their relative stability, it is likely to impose significant effect on the subsequent reactivity for each of the radicals.

Figure 12:
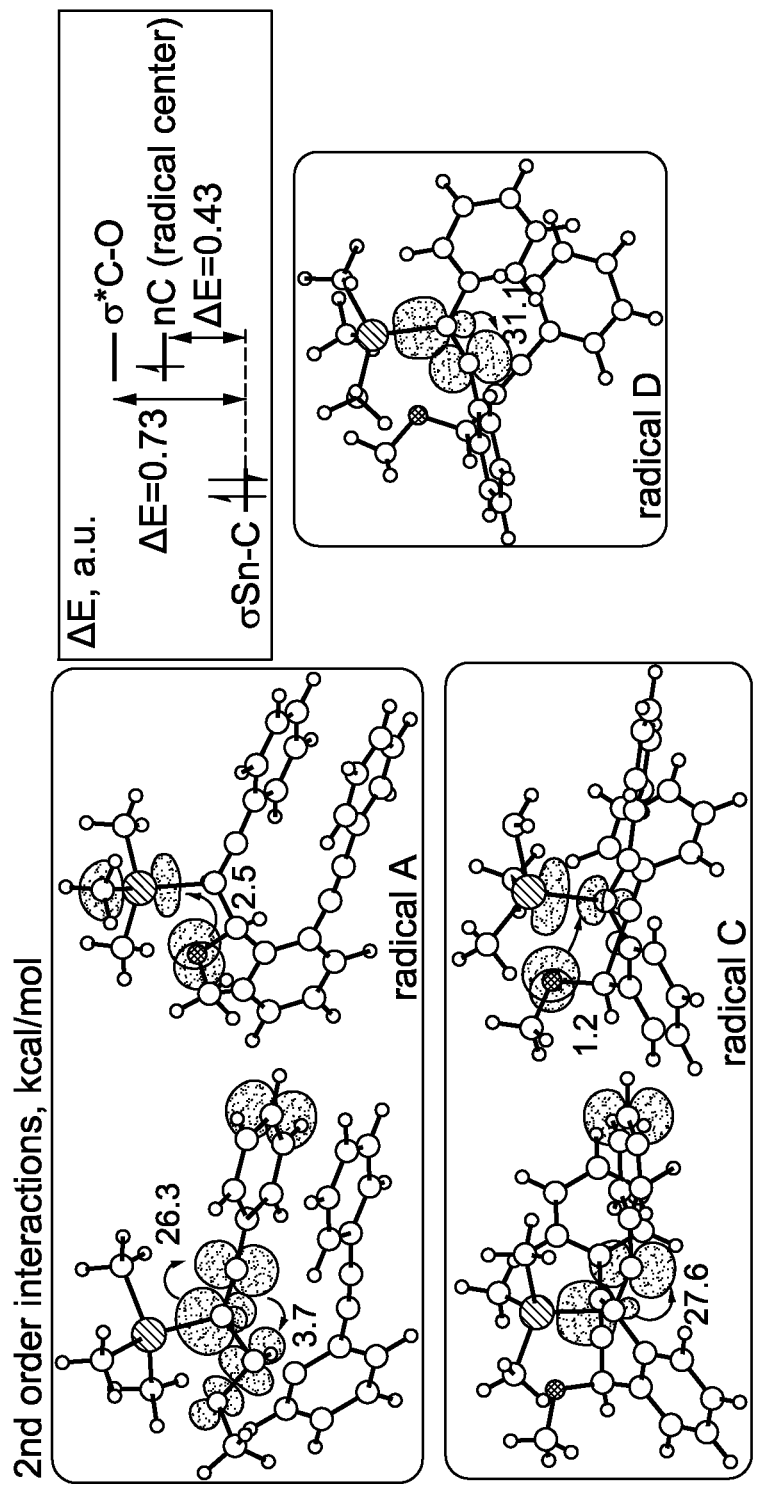
FIG. 12 is a drawing depicting selected electronic interactions (NBO Energies in kcal/mol) contributing to the structure and stability of three vinyl radicals A, C and D. Top left: $\sigma_{Sn-C} \rightarrow$ radical, $\sigma_{Sn-C} \rightarrow \sigma^*_{C-O}$ and $n_O \rightarrow \sigma^*_{Sn-C}$ interactions for radical A. Top right: Rationale for the greater acceptor ability of radical center in comparison to $\sigma^*$C—O orbital based on contrasting energy gaps between these two acceptor orbitals and the donor $\sigma_{Sn-C}$ orbital. Differences in the overlap (not shown) play an additional role. Bottom left: $\sigma_{Sn-C} \rightarrow$ radical and $n_O \rightarrow \sigma^*_{Sn-C}$ interactions for radical C. Bottom right: $\sigma_{Sn-C} \rightarrow$ radical and $n_O \rightarrow \sigma^*_{Sn-C}$ (not shown for clarity, 0.7 kcal/mol) interactions for radical D.

Although the most stable radical A is the only one where the strong hyperconjugative donor ($\sigma_{C-Sn}$) is positioned vicinally to a strong hyperconjugative acceptor ($\sigma^*_{C-O}$), the respective $\sigma_{C-Sn} \to \sigma^*_{C-O}$ interactions is relatively small (3.65 kcal)—considerably smaller than interaction of the C—Sn bond with the radical center (26 kcal). The high acceptor ability of radical center in comparison to that of the C—O bond can be explained by the combination of more favorable stereoelectronic arrangement with the lower energy of the acceptor radical orbital. In particular, while the gap between the C—Sn bond is 0.43 a.u., the gap between C—Sn and $\sigma^*_{C-O}$ is 0.73 a.u., as shown in FIG. 12. FIG. 12 is a drawing depicting selected electronic interactions (NBO Energies in kcal/mol) contributing to the structure and stability of three vinyl radicals A, C and D. Top left: $\sigma_{Sn-C} \to$ radical, $\sigma_{Sn-C} \to \sigma^*_{C-O}$ and $n_O \to \sigma^*_{Sn-C}$ interactions for radical A. Top right: Rationale for the greater acceptor ability of radical center in comparison to $\sigma^*_{C-O}$ orbital based on contrasting energy gaps between these two acceptor orbitals and the donor $\sigma_{Sn-C}$ orbital. Differences in the overlap (not shown) play an additional role. Bottom left: $\sigma_{Sn-C} \to$ radical and $n_O \to \sigma^*_{Sn-C}$ interactions for radical C. Bottom right: $\sigma_{Sn-C} \to$ radical and $n_O \to \sigma^*_{Sn-C}$ (not shown for clarity, 0.7 kcal/mol) interactions for radical D. The efficiency of overlap can be evaluated via the comparison of Fock matrix elements between the donor and acceptor orbitals. Interaction energies can be evaluated via second order perturbative approach as $\Delta E_{if}^{(Q)} \blacksquare 0_8 |F_{if}|^2 / (8_t^{(NL)} - 8_t^{(L)})$. In this case, the $F_{if}$ term for C—Sn bond and radical center is 0.143 a.u. whereas the same term for $\sigma_{C-Sn} \to \sigma^*_{C-O}$ is ~0.046 a.u. Interestingly, the NBO analysis also finds a remote through-space $n_O \to \sigma^*_{Sn-C}$ interaction (2.5 kcal) between propargylic oxygen and $Me_3Sn$-moiety. The other vinyl radicals showed slightly different combinations of similar interactions, suggesting that the overall energies result from a complex interplay between numerous electronic and steric effects. See FIG. 12.

VII. BARRIERS FOR THE CYCLIZATIONS OF VINYL RADICALS

We also calculated the barriers for potentially important cyclizations for the three stable radicals: the most stable radical that can do a 6-exo-dig ring closure and the less stable radicals that can do the potentially faster 5-exo-dig cyclizations. All values are for ΔG in kcal/mol at 110° C. (the experimental temperature).

Figure 10:
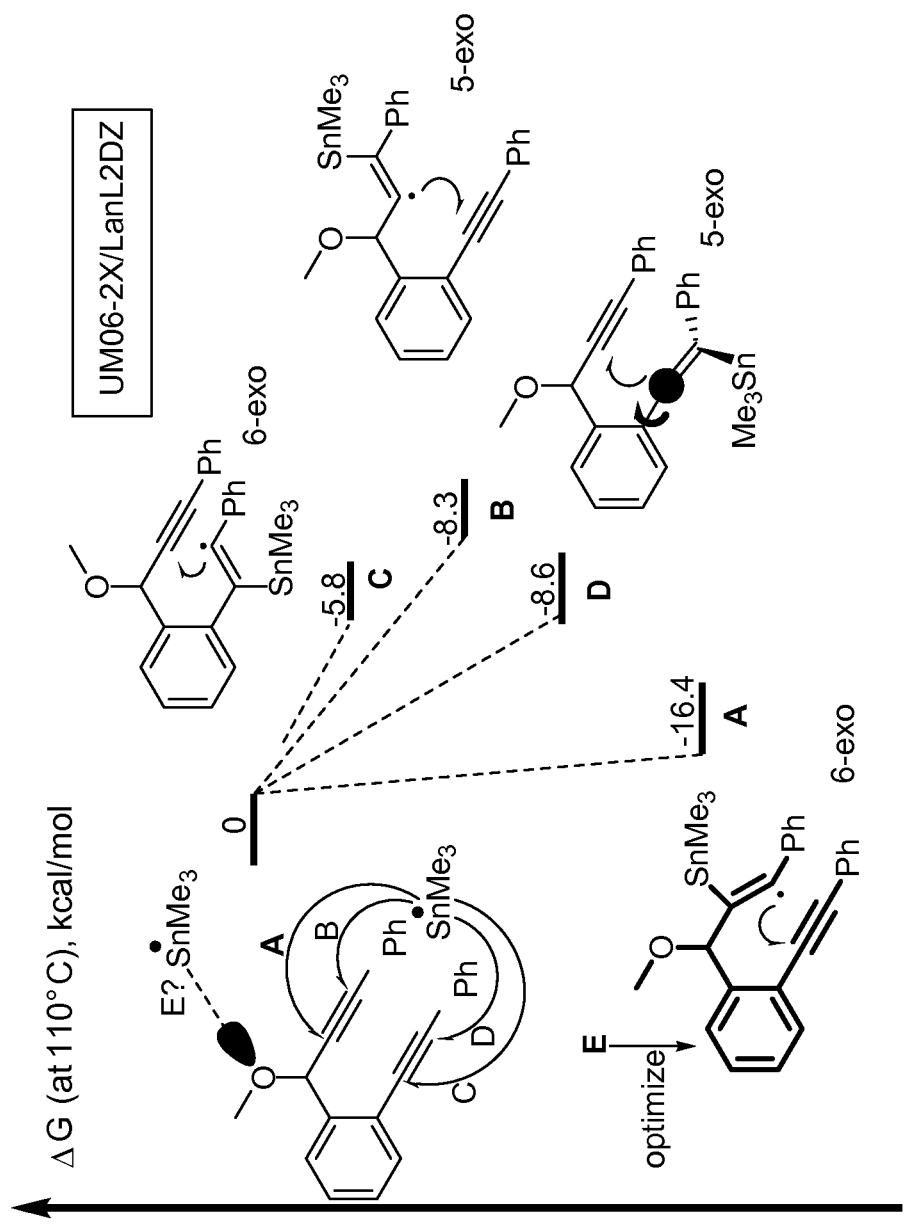
FIG. 10 is a drawing illustrating relative free energies of the four vinyl radicals formed by radical attack at the triple bonds of the skipped enediyne 1a at 110° C.
Figure 11A:
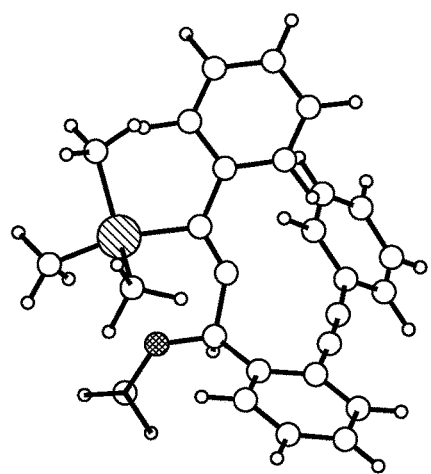
FIGS. 11A, 11B, 11C, and 11D depict the calculated geometries of the four vinyl radicals A (FIG. 11A), B (FIG. 11B), C (FIG. 11C), and D (FIG. 11D) at UM06-2X/LanL2DZ level of theory.
Figure 11B:
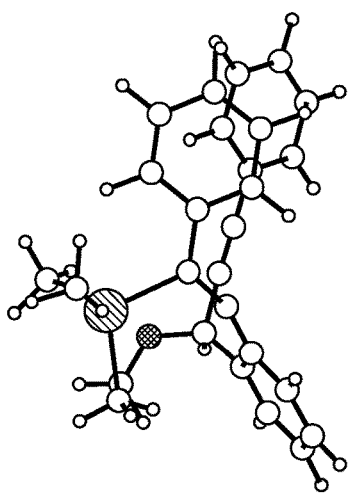
Figure 11C:
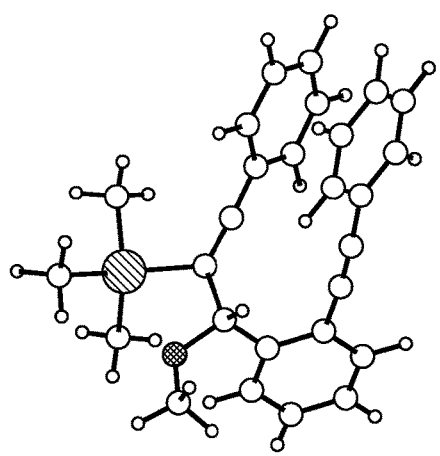
Figure 11D:
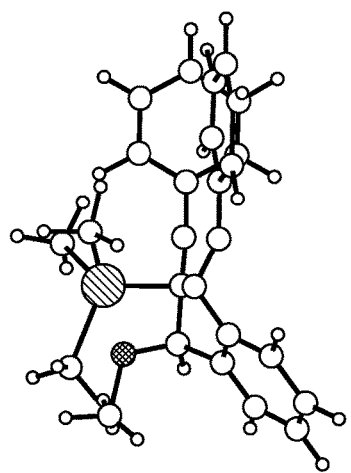

The 13.8 kcal/mol barrier for 6-exo-dig cyclization of the most stable radical A suggests that this reaction will provide the lowest energy path for the escape from the pool, when the next most stable radical D has the barrier for its fastest cyclization that substantially exceeds 6.0 kcal (=13.8-7.8, FIG. 10). The cyclization is highly exothermic, exergonic and effectively irreversible.

Figure 13:
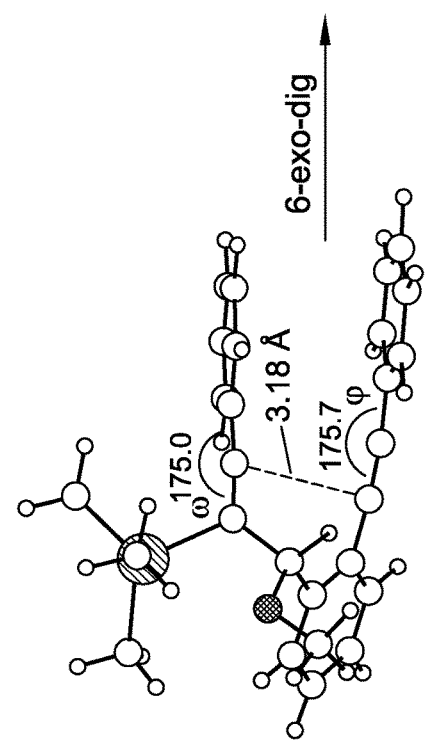
FIG. 13 depicts the geometries of radical A and its transition state for the 6-exo-dig cyclization.
Figure 13:
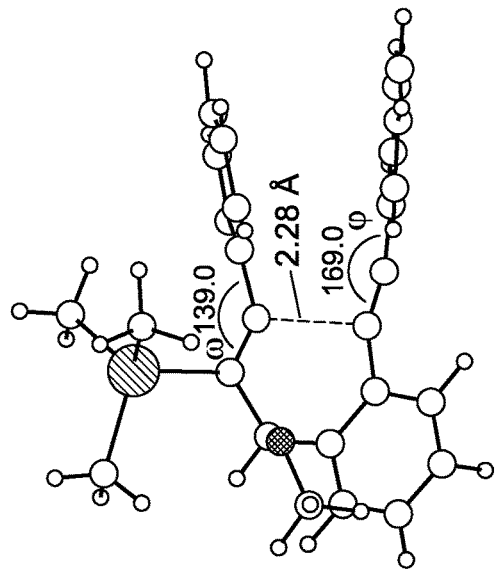
Figure 14:
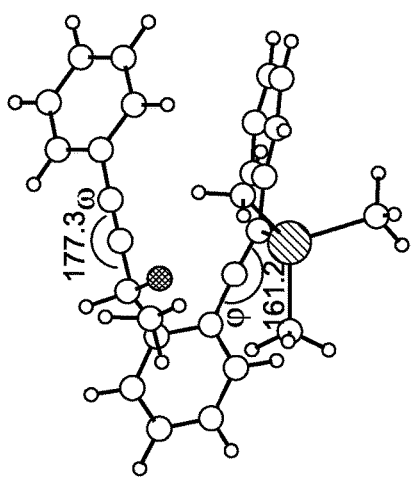
FIG. 14 depicts the geometries of the radical D and its transition state for the 5-exo-dig cyclization.
Figure 14:
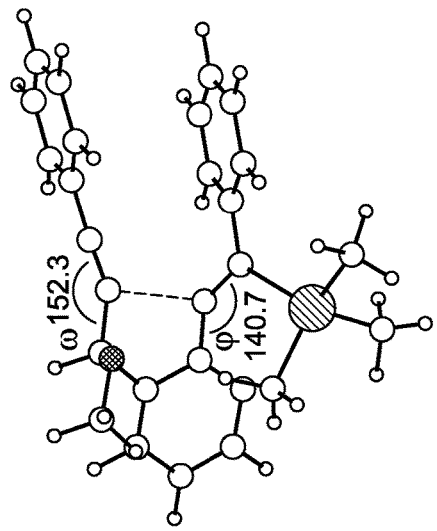

Indeed, although the 11.8 kcal energy barrier for the 5-exo-dig cyclization of radical D is lower than the 6-exo barrier for radical A if the respective radicals are taken as the reference points, the absolute energy of the 6-exo-dig barrier is lower. See FIG. 13, which depicts the geometries of radical A and its transition state for the 6-exo-dig cyclization. This 5-exo barrier is higher than a typical 5-exo-dig barrier due to a stereoelectronic penalty that the reacting radical has to pay for rotating out of conjugation with the central benzene ring in order to attack the triple bond in the transition state, as seen in FIG. 14, which depicts the geometries of the radical D and its transition state for the 5-exo-dig cyclization. See Kovalenko, S. V.; Peabody, S.; Manoharan, M.; Clark, R. J., Alabugin, I. V. *Org. Lett.* 2004, 6, 2457. Alabugin, I. V.; Manoharan, M. *J. Am. Chem. Soc.* 2005, 127, 12583. Note also the change from an edge-to-face to the face-to-face interaction between the two terminal Ph groups.

Such penalty is unique for this radical because, unlike radicals A and C, radical D is conjugated with an aromatic system that is annealed to the forming ring. Due to this structural constraint, the central aromatic system is incapable of the same facile rotation that terminal aryl groups in radical A and C can do without penalty. Since such rotation can result in a ~10 kcal penalty, this loss of conjugation of radical center with the vicinal phenyl group should account for this relatively high barrier.

Figure 15:
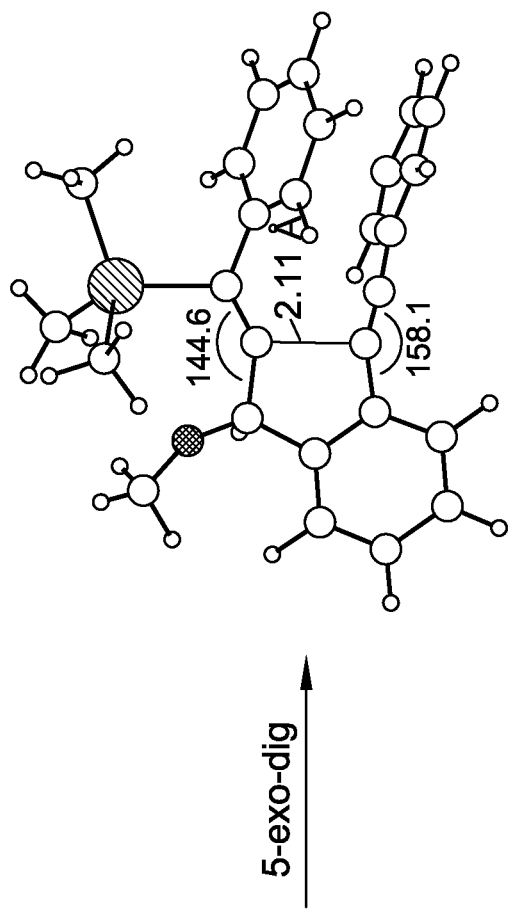
FIG. 15 depicts the geometries of the radical B and its transition state for the 5-exo-dig cyclization.
Figure 15:
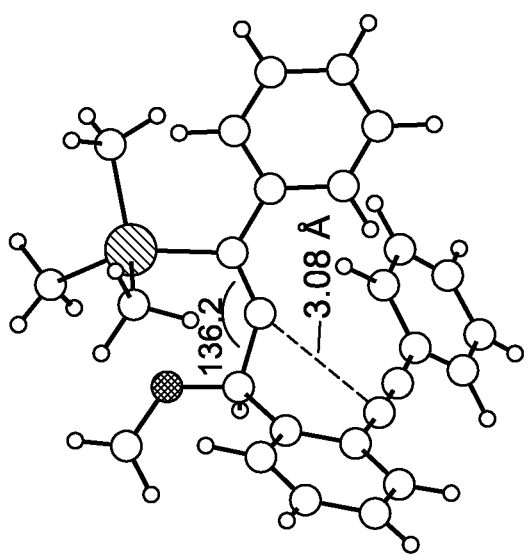

Because the above 5-exo-dig cyclization is unusually slow, we also analyzed 5-exo-dig cyclization of radical B which does not have to pay the same penalty in the cyclization TS. See FIG. 15, which depicts the geometries of the radical B and its transition state for the 5-exo-dig cyclization. However, the barrier is only slightly lower (11.3 kcal), presumably due to steric interaction in the TS.

Overall, the calculated energies for the competing radical reactions of the key components of the radical pool can also rationalize the observed selectivity of the radical cascade as long as the barriers for radical equilibration are sufficiently low. Note that the present situation is different from that in the radical pool presented in FIG. 7 because the desired 6-exo-dig cyclization will have to compete with two 5-exo cyclizations. As we discussed above, 5-exo-dig barriers are generally lower than the 6-exo-dig alternatives. See Frisch, M. J. et. al. *Gaussian 09, Revision B*.01; Gaussian: Wallingford, C T, 2009 and (a) Zhao, Y.; Truhlar, D. G. *Theor. Chem. Acc.* 2008, 120, 215. (b) Zhao, Y.; Truhlar, D. G. *Acc. Chem. Res.* 2008, 41, 157. Consequently, in order to achieve selective reaction in this scenario one has either to stabilize the reactant that has to undergo the usually slower 6-exo-path to the extent where its cyclization has the lowest absolute energy out of the all possible barriers or destabilize the 5-exo TS for the less stable radicals. The above discussed stereoelectronic penalty for the unusually slow 5-exo-dig cyclization of radical D leads to ~5.7 kcal/mol preference for the 6-exo-dig cyclization of radical A.

Figure 16:
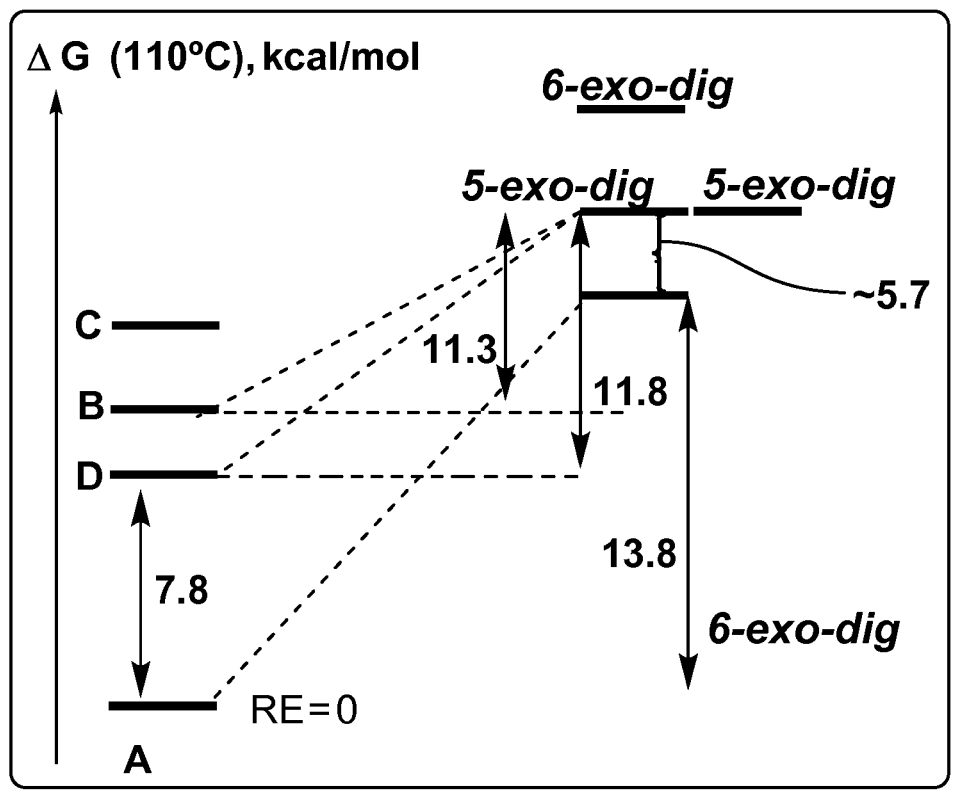
FIG. 16 illustrates the comparison of relative energies of the four vinyl radicals and barriers for their exo-dig cyclizations.

At the present time, we do not have the sufficiently accurate information about the barriers for C—Sn bond fragmentation in the vinyl radicals A-D and the barriers for the interconversion in these radicals via metallotropic shifts. In order for the radical pool concept to operate, such barriers have to be lower than the absolute barrier for the 6-exo-dig cyclization of radical A. Based on the kinetic preference for the formation of radical A (see FIGS. 10 and 16) and the Occam's razor, we rationalize the observed selectivities as a direct facilitating effect of the OR group on the Bu₃Sn attack at the propargylic position followed by trapping of the kinetically formed vinyl radical by a fast and irreversible 6-exo cyclization.

VIII. FULL RADICAL CASCADE AND RETURN OF THE RADICAL AT THE β-CARBON

Figure 17:
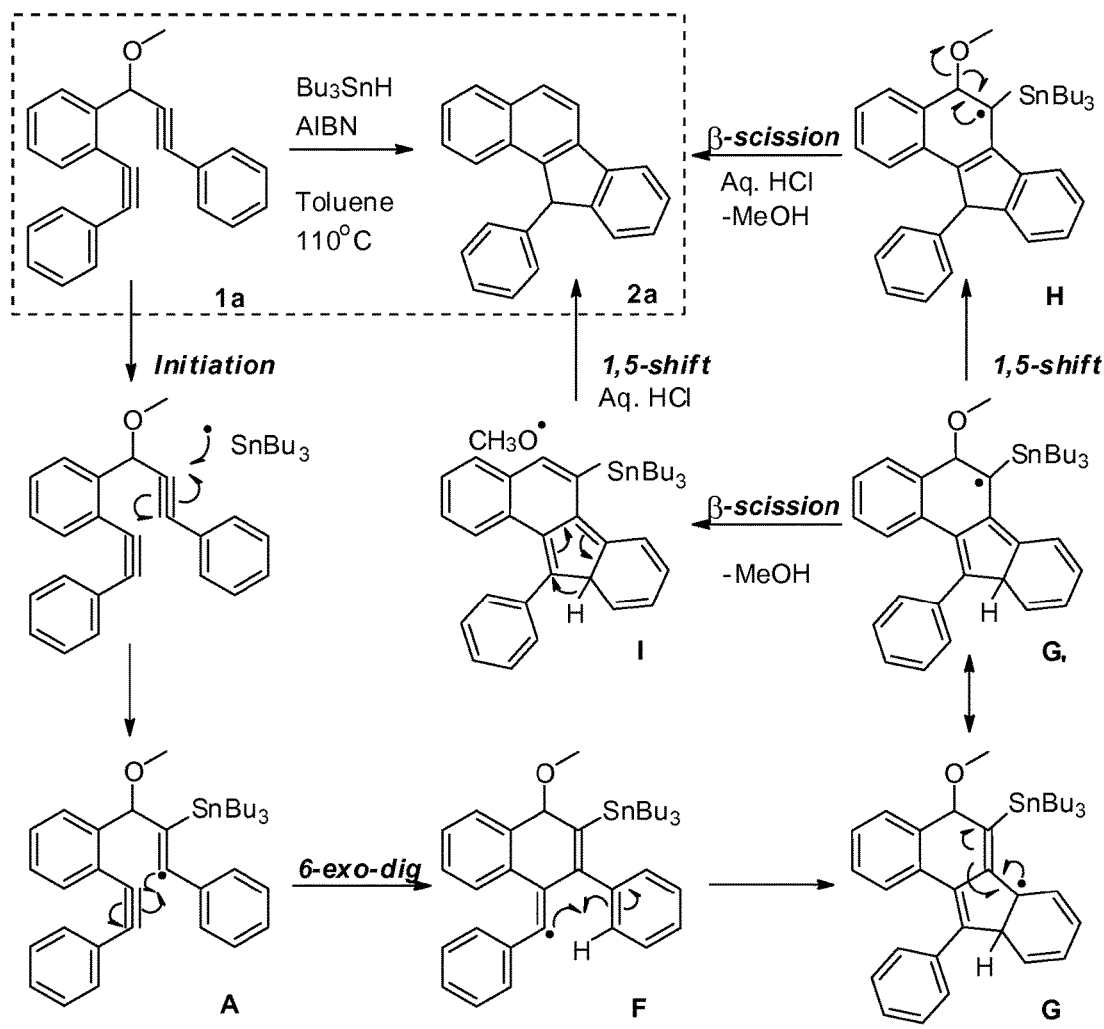
FIG. 17 depicts the proposed mechanism of cascade cyclization. Note the continuous translocation of the radical center through the molecule and conversion of 6-radicals (A and F) to delocalized π-radicals G and H where the radical is positioned next to the departing directing group.
Figure 18:
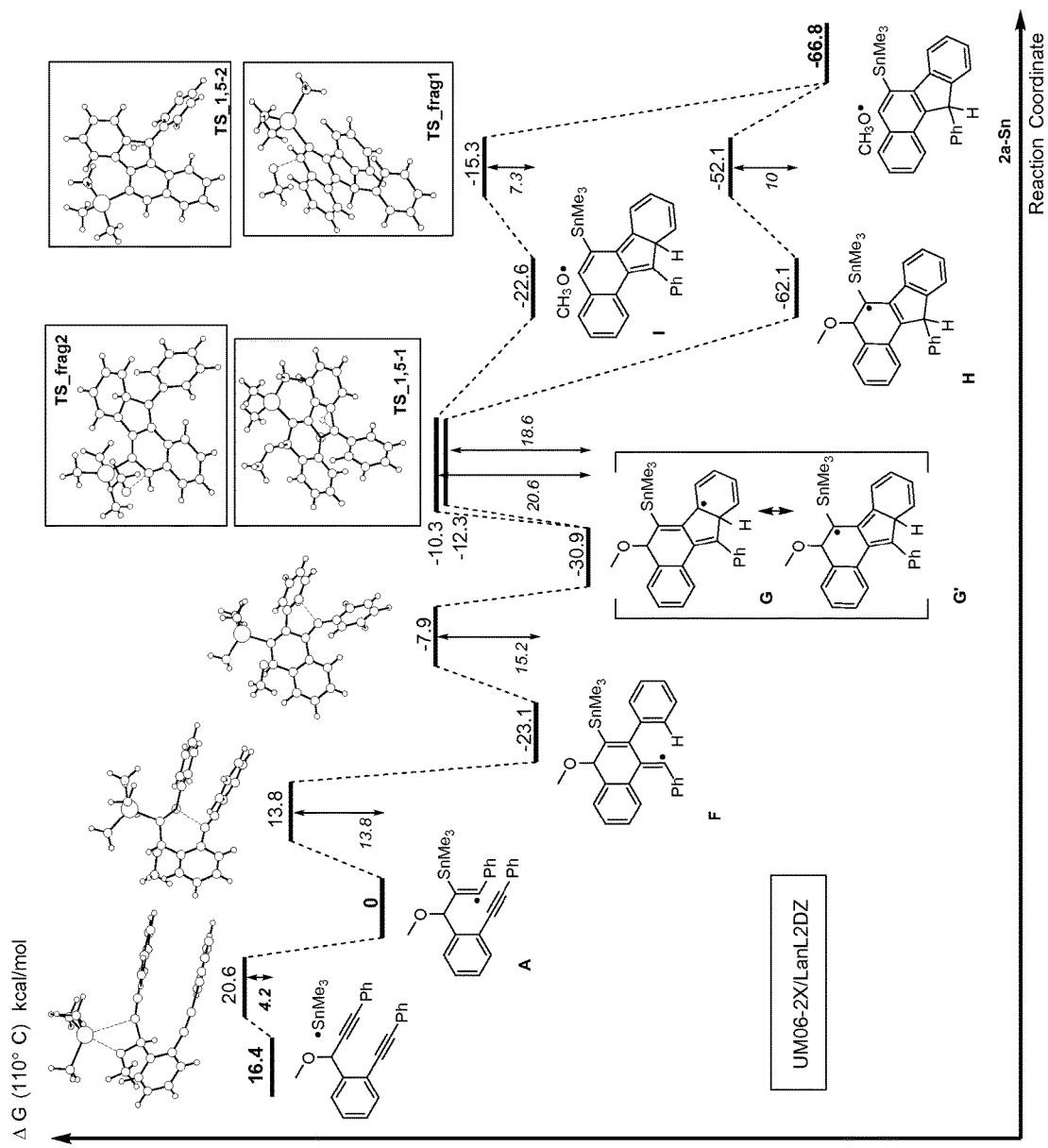
FIG. 18 provides the calculated energy profile for the cascade radical transformation of diyne 1a. All energies are given relative to radical A except for the smaller numbers in italics that correspond to the activation barrier heights relative to the preceding energy minima.

The selective 6-exo-dig cyclization discussed in the previous section initiates the experimentally observed cascade. FIG. 17 shows a proposed mechanism involving an initial formation of a radical intermediate A formed via the attack of the Bu₃Sn radical at the central alkyne. The subsequent 6-exo-dig cyclization forms the second vinyl radical intermediate F. Attack of the neighboring phenyl i-system results in a delocalized radical G, leading to rearomatization via a 1,5-hydrogen shift. See Alabugin, I. V.; Manoharan, M.; Breiner, B.; Lewis, F. *J. Am. Chem. Soc.* 2003, 125, 9329. Finally, fragmentation of intermediate H allows for the aromatization of the top ring into a naphthalene moiety. This explanation supports the journey of the radical in this system: it begins with the Bu₃Sn radical attacking the alkyne position vicinal to the directing group starting a boomerang-like radical journey. The vinyl radical is formed, leading to the 5-exo-dig cyclization: this is the furthest position of the radical from where it started. The formation of the 5-membered ring makes the radical closer to its origins but not enough: another resonance structure can be written. At this point the boomerang is back to its initial position, vicinally to the directing and now leaving group. This position is especially interesting because it will end forming a new π bond and making the directing OR group leave the system. Most importantly, the last step removes the directing group from the product, making this directing approach traceless. The other approach is that G' can undergo the β-scission of the OR first and then do the 1,5-shift to rearomatize the system. Both possibilities are presented in FIG. 17 and FIG. 18.

The proposed reaction mechanism is supported by the calculated free energy profile for the full cascade transformation. See FIG. 18, which provides the calculated energy profile for the cascade radical transformation of diyne 1a. All energies are given relative to radical A except for the smaller numbers in italics that correspond to the activation barrier heights relative to the preceding energy minima. As discussed above, the initial 6-exo-dig cyclization is moderately fast but highly exergonic and effectively irreversible. Subsequent attack at the aromatic ring proceeds via a slightly higher (15.2 kcal) barrier. This process is mildly exergonic and moves system even down the potential energy path. As a consequence, even the relatively high barrier for the subsequent 1,5-hydrogen shift (18.6 kcal) is still lower in the absolute energy than the two previous barriers, so the cascade can move forward. Because the 1,5-shift leads to aromatization, it is highly exergonic and takes the system ~62 kcal lower than the original vinyl radical A. The key final β-scission of the directing OR group has a barrier of only 10 kcal for R=Me (a slightly higher 15.4 kcal barrier was calculated for R=H, where reaction was found to proceed slower experimentally). This process is exergonic by ~5 kcal/mol. Furthermore, the released OR radicals can be quickly intercepted via other thermodynamically favorable processes (e.g., H-abstraction from Bu₃Sn—H, propagating the cascade).

We had also calculated the alternative pathway where fragmentation precedes 1,5-shift. Overall, the highest barrier on this path is only marginally higher. Considering the challenges in accurate computing of reaction barriers for large Sn-containing species, this path may serve as an alternative to the mechanism outlined above. Interestingly, the barriers for the same reactions are lower when they terminate the cascade in comparison to the analogous barriers when these reactions serve as penultimate step (18.6.0 vs. 7.3 kcal for the 1,5-shift, 10.0 vs. 20.6 kcal for the fragmentation). This is a direct evidence for thermodynamic contribution to reaction barrier as outlined by the Marcus theory. See Alabugin, I. V.; Manoharan, M.; Breiner, B.; Lewis, F. *J. Am. Chem. Soc.* 2003, 125, 9329. When the two reactions terminate the cascade, they are assisted by significant aromatic stabilization (formation of one aromatic ring for fragmentation and two aromatic rings for 1,5-shift).

An interesting stereoelectronic feature is observed in the computed fragmentation TS where steric repulsion between the bulky $Me_3Sn$ moiety and the OMe group helps in pushing the OMe group away from planarity and aligning breaking C—O bond with the aromatic $\pi$-system. This effect, which can be classified as steric assistance, should be increased further in the real system which has an even more bulky $Bu_3Sn$ moiety instead of the $Me_3Sn$ group used in the computational analysis. If these expectations are correct, the experimental fragmentation barrier should be lowered even further.

IX. FUNCTIONALIZATION OF STANNYL BENZOFLUORENES

Figure 19:
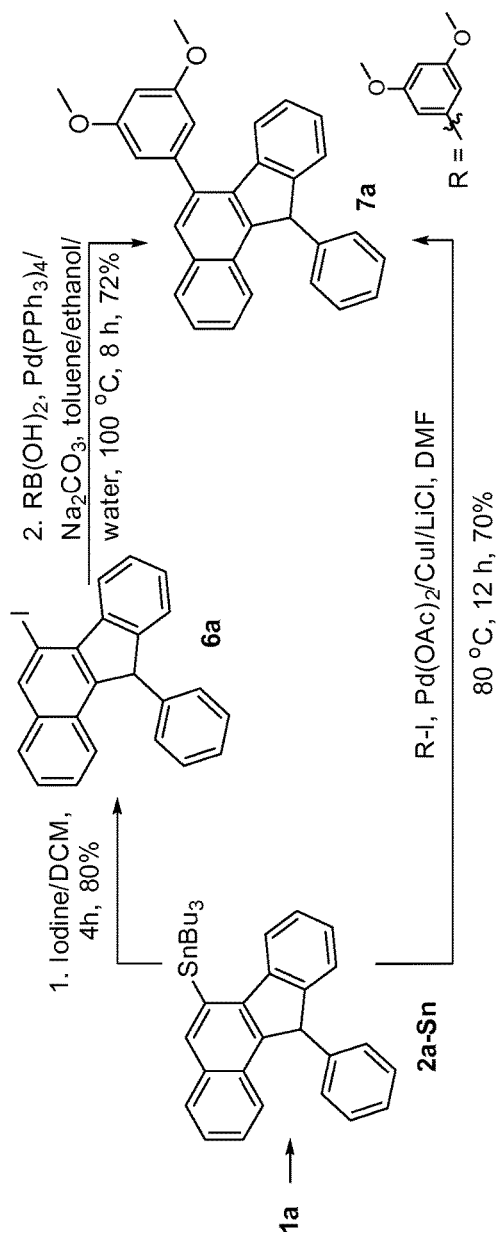
FIG. 19 depicts derivatization of benzofluorenes using Stille and Suzuki coupling reactions.

Two practical conclusions can be obtained from these results. First, this cascade provides a practical synthetic approach to substituted benzo[a]fluorenes, the class of compounds with known anticancer activity. See Jones, C. D.; Blaszczak, L. C.; Goettel, M. E.; Suarez, T.; Crowell, T. A.; Mabry, T. A.; Ruenitz, P. C.; Srivatsan, V. *J. Med. Chem.* 1992, 35, 931. Furthermore, the Sn-containing products can be introduced in reactions with a variety of electrophiles. For example, they can be readily protodestannylated to yield the respective hydrocarbon and introduced in Stille cross-coupling. Alternatively, they can be converted into an electrophilic benzofluorenone building blocks via reaction with iodine and/or reacted with carbon nucleophiles, i.e., boronic acids under Suzuki conditions. See FIG. 19, which depicts derivatization of benzofluorenes using Stille and Suzuki coupling reactions. Furthermore, a variety of other functionalization avenues are possible. For example: Ye, Y.; Sanford, M. S. *J. Am. Chem. Soc.* 2013, 135, 4648. Huang, C.; Liang, T.; Harada, S.; Lee, E.; Ritter, T. *J. Am. Chem. Soc.* 2011, 133, 13308.

Figure 20:
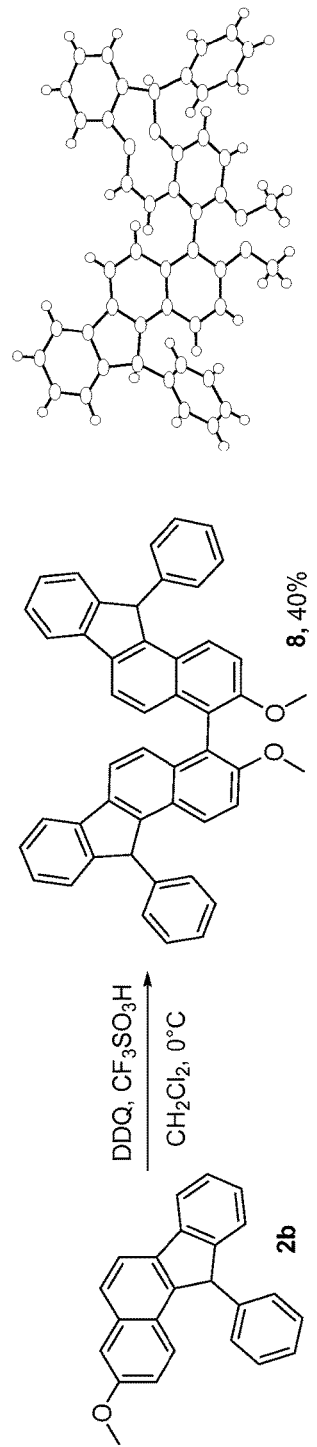
FIG. 20 depicts the oxidative dimerization of 2b.

Additionally, the presence of an activating β-OR group in 2b can be used to direct oxidative dimerization into an expanded polyaromatic system. See FIG. 20, which depicts the oxidative dimerization of 2b.

X. FORMATION OF LARGER POLYAROMATIC SYSTEMS

Figure 21:
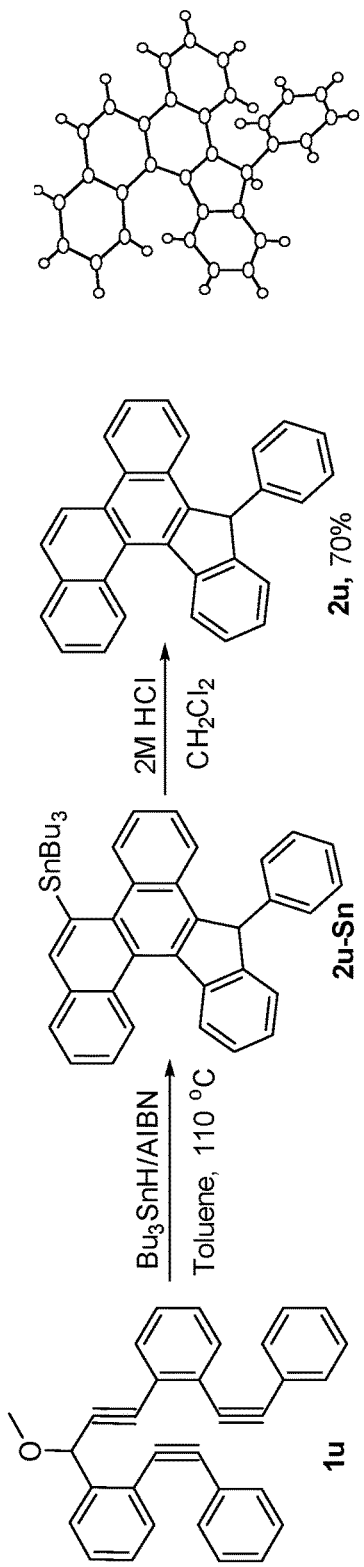
FIG. 21 depicts cascade transformation of skipped trisalkyne 1u and X-ray geometry of the product

To our satisfaction, the traceless directing group method works very well with the larger oligoalkyne systems. The analogous cascade with a triyne proceeded as planned and provided good yield of a new expanded polyaromatic system. The success of the expanded cascade is consistent with the higher rate of the 6-exo-dig attack at the last triple bond relative to attack of the same vinyl radical at the aromatics. See Alabugin, I. V.; Gilmore, K.; Patil, S.; Manoharan, M.; Kovalenko, S.; Clark, R. J.; Ghiviriga, I. *J. Am. Chem. Soc.* 2008, 130, 11535. Termination of the cascade with the elimination of the directing —OMe group proceeds in exactly the same way as it does for the formation of benzofluorenes in the previous section. See FIG. 21, which depicts cascade transformation of skipped tris-alkyne 1u and X-ray geometry of the product.

Addition of the forth alkyne moiety to the reactants introduced the new level of structural complexity in the cascade products. See FIG. 22, which depicts cascade transformation of skipped tetraynes 1v-x leads to the formation of diastereomeric helicenes. The combination of $^1H$ and $^{13}C$ NMR data confirmed that reaction still proceeded as above providing fully aromatized products with the loss of OMe-moiety and benzofluorene terminus. However, the product was formed as a mixture of two products. All NMR features of these products clearly correspond to the fully complete cascade. We attribute this observation to the presence of two diastereomers originating from the formation of chiral center and atropoisomerism of the two spatially close naphthalenes in the helicene moiety.

In order to facilitate separation of the two diastereomeric helicenes, we attached polarizing substituents to the polycyclic framework. The mixture of the two dimethoxy-substituted products can be separated by crystallization of diastereoisomers from $CD_3CN$ (90% purity).

Figure 23:
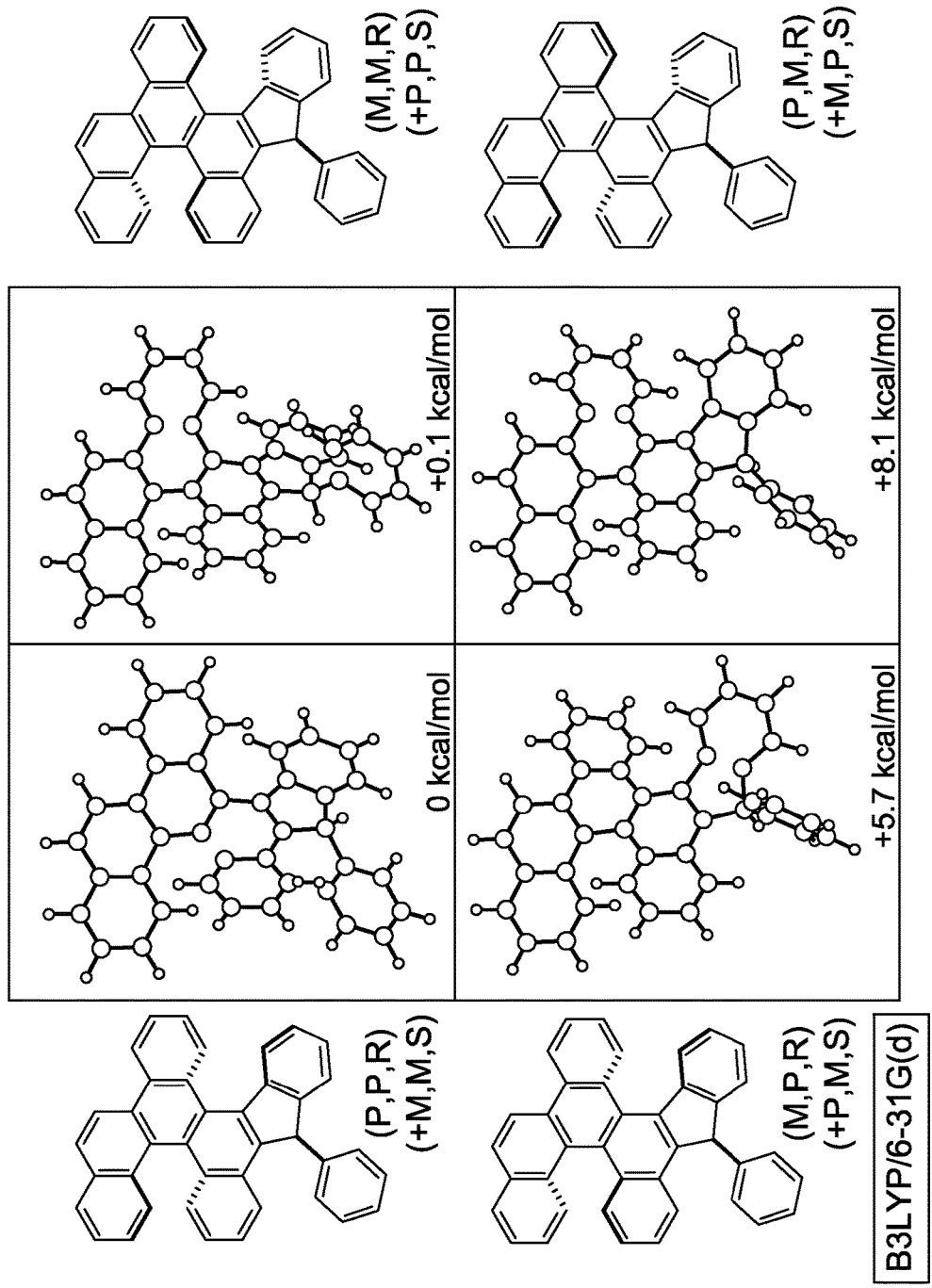
FIG. 23 is an illustration of the geometries and energies of the four diastereomeric fused helicenes 2v (only one of the two enantiomers is shown for each structure).

These structures correspond to the fusion of two different [5]helicenes: one made entirely of benzene rings and the other containing a pentagon. In order to understand the relative influence of the two helicene units at each other, we analyzed the relative energies of the four diastereomers of the parent fused helicene 2v by DFT. See FIG. 23, which is an illustration of the geometries and energies of the four diastereomeric fused helicenes 2v (only one of the two enantiomers is shown for each structure). The two stable conformations correspond to the same chirality of the two helicenes (either P, P or M, M), so the preferred geometries of the two fused chirality units are strongly coupled. The mismatched isomers are much higher in energy (~5 kcal and ~8 kcal higher). On the other hand, effect of chirality at the auxiliary $sp^3$ asymmetric carbon in the two stable stereoisomers is minor (~0.1 kcal). These computational results are consistent with the experimental observation of two isomeric products formed in the ~1:1 ratio. The pristine [5]helicene has the inversion barrier of ~23 kcal/mol, Janke, R. H.; Haufe, G.; Würthwein, E.-U.; Borkent, J. H. *J. Am. Chem. Soc.* 1996, 118, 6031.

XI. SELECTED PHOTOPHYSICAL PROPERTIES OF BENZO[A]FLUORENE CHROMOPHORES

Figure 24A:
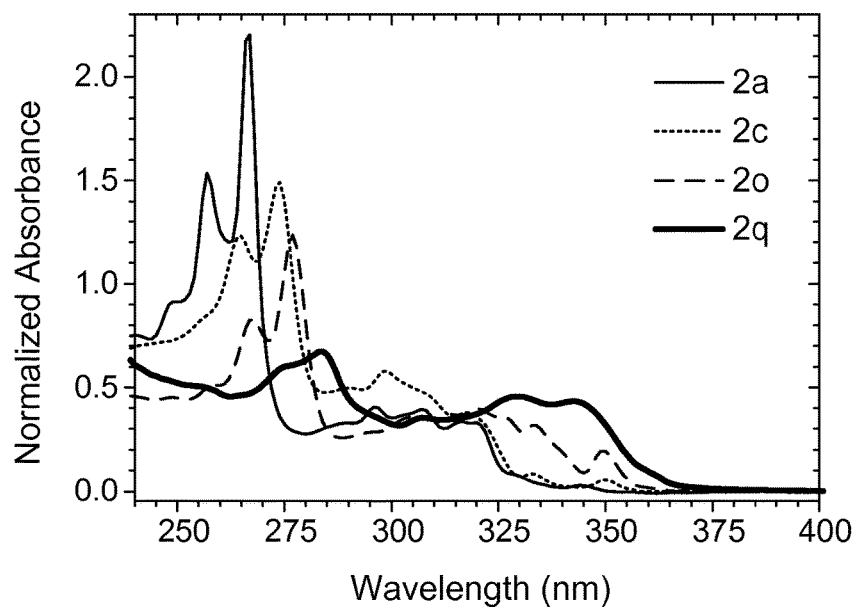
FIGS. 24A and 24B are graphs illustrating normalized (FIG. 24A) absorption and (FIG. 24B) emission spectra of 2a, 2c, 2o and 2q in CH$_2$Cl$_2$ at room temperature. The absorption spectra have been normalized with respect to absorption at 316 nm.
Figure 24B:
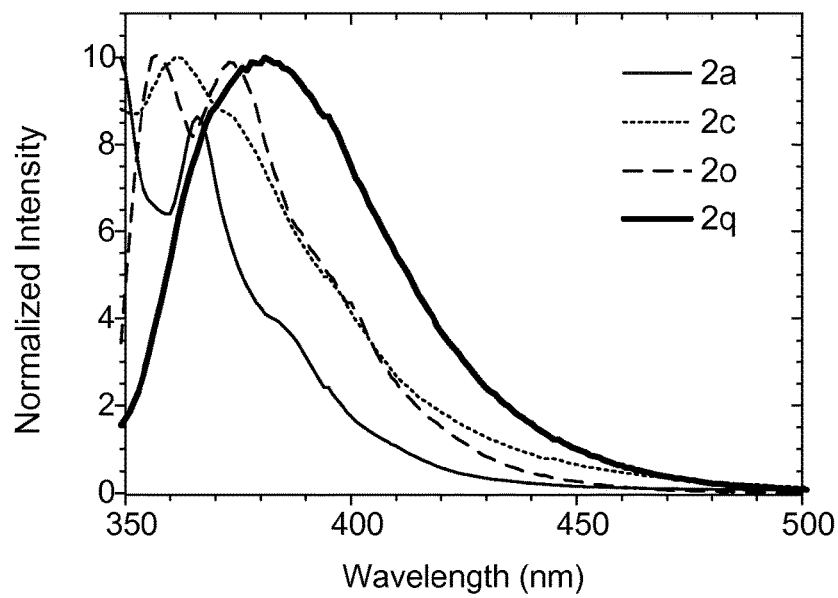

The photophysical properties for select compounds were recorded in aerated dichloromethane and the results are summarized in Table 5. Representative spectra are shown in FIGS. 24A and 24B. FIGS. 24A and 24B are graphs illustrating normalized (FIG. 24A) absorption and (FIG. 24B) emission spectra of 2a, 2c, 2o and 2q in $CH_2Cl_2$ at room temperature. The absorption spectra have been normalized with respect to absorption at 316 nm. The parent compound, 2a, exhibits structured absorption features below 350 nm and an emission maximum at 365 nm.

TABLE 1

Photophysical properties of select complexes in $CH_2Cl_2$.

| complex | absorbance $\lambda$(nm) | emission at rt $\lambda_{max}$ (nm) | $\tau$ (ns) | $\Phi_{PL}$ | $k_r$ ($\times 10^7 s^{-1}$)[a] | $k_{nr}$ ($\times 10^8 s^{-1}$)[b] |
|---|---|---|---|---|---|---|
| 2a | 257, 266, 316, 344 | 365, 384 | 1.5 | 0.091 | 6.07 | 6.06 |
| 2b | 258, 267, 343, 358 | 372 | 7.6 | 0.201 | 2.63 | 1.05 |

TABLE 1-continued

Photophysical properties of select complexes in $CH_2Cl_2$.

| complex | absorbance λ(nm) | emission at rt $\lambda_{max}$ (nm) | τ (ns) | $\Phi_{PL}$ | $k_r$ (×10$^7$s$^{-1}$)$^a$ | $k_{nr}$ (×10$^8$s$^{-1}$)$^b$ |
|---------|------------------|--------------------------------------|--------|-------------|------------------------------|--------------------------------|
| 2c | 258, 268, 319, 337 | 361, 379 | 4.3 | 0.072 | 1.69 | 2.18 |
| 2m | 264, 273, 333, 350 | 361, 373 | 6.3 | 0.165 | 2.62 | 1.33 |
| 2o | 268, 277, 320, 350 | 357, 373 | 5.8 | 0.589 | 10.23 | 0.71 |
| 2q | 276, 284, 329, 344 | 386 | 2.9 | 0.603 | 20.79 | 1.37 |
| 2u | 281, 294, 350, 391 | 393, 413 | 11.5 | 0.193 | 1.68 | 0.70 |
| 8 | 266, 276, 326, 370 | 375, 391 | 5.9 | 0.251 | 4.26 | 1.27 |

$^a k_r = \Phi/\tau$
$^b k_{nr} = (1 - \Phi)/\tau$

The modular nature of the synthetic method introduced here is ideal for generating multi-functionalized compounds. The energy of absorption and emission peaks are shifted upon substitution. A class of molecules that are of particular interest for their unique photophysical properties are push-pull/donor-acceptor systems, like compound 2q, which combine of electron withdrawing (—CN) and donating (—OMe) groups. The relatively unstructured absorption and emission features for 2q in dichloromethane are indicative of at least some charge transfer character associated with these transitions. Further support for this assignment is provided by solvent dependent absorption and emission spectroscopy. See FIGS. 24A and 24B. Compound 2q exhibits a shift in emission maximum in the order 371, 379, 383 and 399 nm in hexane, 1,4-dioxane, chloroform and dimethyl sulfoxide, respectively. This bathochromic shift and loss of vibrational features in increasingly polar solvents is attributed to an increase in the molecular dipole moment upon excitation. See Wilde, A. P.; King, K. A.; Watts, R. J. *J. Phys. Chem.*, 1991, 95, 629. A similar, albeit less pronounced, bathochromic shift from 326 nm in hexanes to 331 nm in dimethyl sulfoxide is observed in absorption. In contrast, for compound 2a, which lacks donor and acceptor groups, there is nominal change in both structure and energy (<5 nm) of absorption and emission.

Figure 25A:
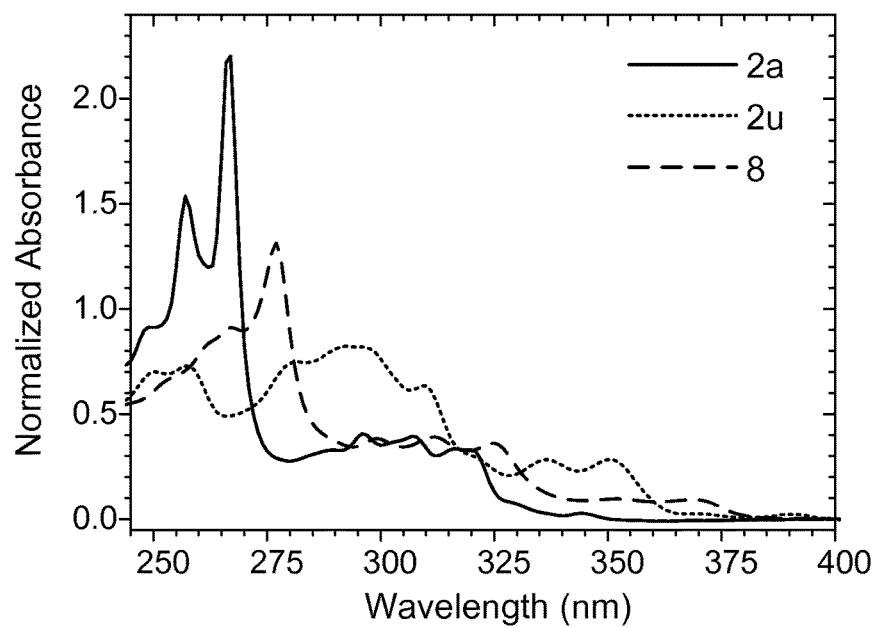
FIGS. 25A and 25B are graphs illustrating normalized (FIG. 25A) absorption and (FIG. 25B) emission spectra of 2a, 2u and 8 in CH$_2$Cl$_2$ at room temperature. The absorption spectra have been normalized with respect to absorption at 316 nm.
Figure 25B:
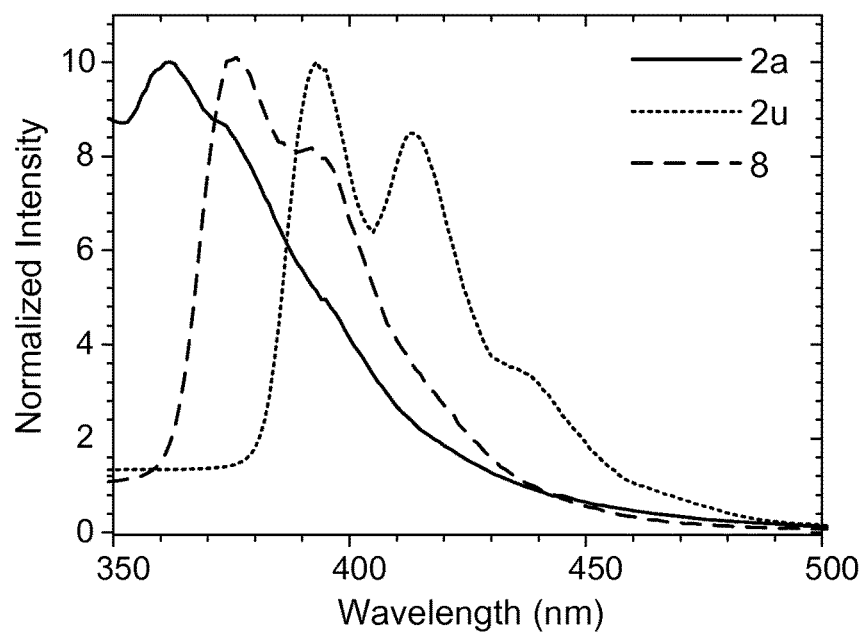

The absorption properties of the compounds are not the only photophysical parameter tunable via substitution. The luminescent quantum yields (D) measured at room temperature for the complexes vary between 0.072-0.603. The significantly higher quantum yield for 2o (0.589) and 2q (0.603), relative to the other complexes (<0.251), is attributed to the significantly higher radiative rate constant ($k_r$). See Table 5. The enhanced $k_r$ is presumably due to greater excited-ground state coupling. The role of the cyano groups in this increased coupling requires further investigation. The bathochromic shift observed with 2u and 8 is due to an increase in the degree of conjugation. See FIGS. 25A and 25B. FIGS. 25A and 25B are graphs illustrating normalized (FIG. 25A) absorption and (FIG. 25B) emission spectra of 2a, 2u and 8 in $CH_2Cl_2$ at room temperature. The absorption spectra have been normalized with respect to absorption at 316 nm.

XII. CONCLUSIONS

Polycyclic aromatics are important subunits in many natural products, pharmaceuticals, and materials. Alkynes are convenient carbon-rich precursors for the formation of carbon-rich polyaromatics. The advantage of radical cascades stems from their broad functional group tolerance, and the combination of high reactivity with controllable selectivity.

According to the present invention, a new approach is disclosed for the efficient transformation of skipped oligoalkynes into polycyclic ribbons of tunable dimensions. Incorporation of tin moiety allowed for further functionalization at the initial site of attack via regioselective reactions with electrophiles and Stille and Suzuki cross-coupling reactions. The regioselectivity of the initial attack is directed by propargyl alkoxy moiety which is eliminated at the end of cascade, serving as a traceless directing functionality.

Figure 22:
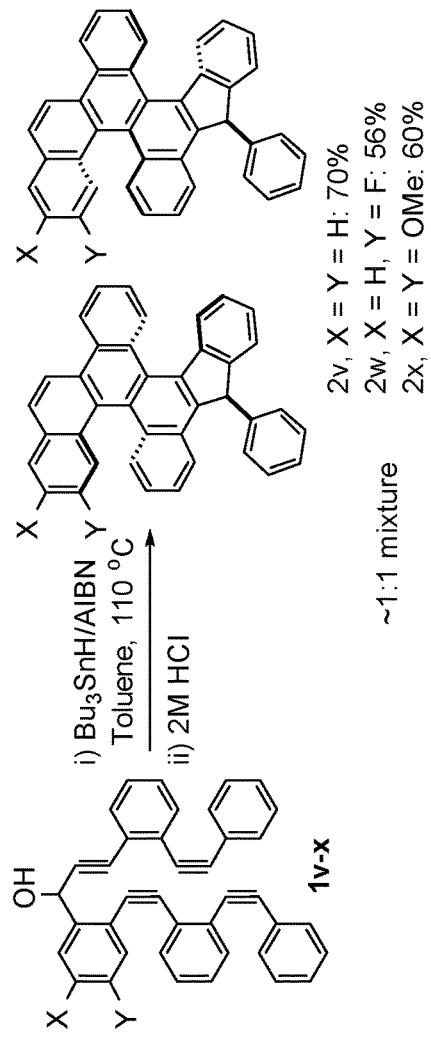
FIG. 22 depicts cascade transformation of skipped tetraynes 1v-x leads to the formation of diastereomeric helicenes.

In the representative examples shown in FIG. 22, the directing group is replaced (sometimes by H, sometimes by a different functionality). Design of radical cascades presented in this work is different because the directing group is not replaced but eliminated. Consequently, the present design does not require a separate reaction for the removal of directing group. This step is an integral part of reaction cascade that provides an efficient approach to Sn-functionalized polyaromatics. Furthermore, our work provides a first example of a traceless directing group in a radical cascade.

EXAMPLES

The following non-limiting examples are provided to further illustrate the present invention.

Unless otherwise noted, all reactions were carried out under nitrogen atmosphere in oven-dried glassware using standard syringe, cannula, and septa apparatus. Benzene, diethyl ether, toluene, tetrahydrofuran, and hexane were dried with a dry solvent system before use. Dichloromethane was dried over $CaH_2$ before use. Reagents were purchased from commercial sources and used without purification, unless otherwise stated. Reactions were magnetically stirred and monitored by thin layer chromatography carried out on 0.25 mm silica gel plates (60f-254) using UV light as visualizing agents and ethanolic solution of phosphomolybdic acid and heat as developing agents. Column chromatography was performed using Kieselgel 60 (70-230 mesh) or Kieselgel 60 (230-400 mesh). Preparative thin-layer chromatography (PTLC) separations were carried out on 0.25 or 0.55 mm silica gel plates (60F-254).

Synthetic Scheme (A1) for the Preparation of 1-(1-methoxy-3-phenylprop-2-yn-1-yl)-2-(phenylethynyl)benzene (1a)

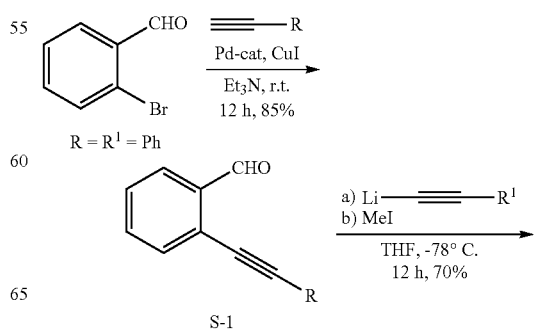

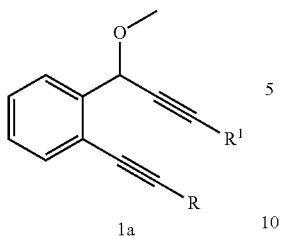

1a a) Synthesis of 2-(phenylethynyl)benzaldehyde (S-1)

2-bromobenzaldehyde (1.00 g, 5.43 mmol) was added in one portion to a solution of CuI (0.10 g, 10 mol %) in Et₃N (30 mL) and degassed with nitrogen for 15 min at 23° C. PdCl₂(PPh₃)₂ (0.32 g, 5 mol %) was added to the mixture and was stirred for 15 min before being treated with ethynylbenzene (0.63 g, 6.2 mmol) dropwise. The resulting solution was stirred at room temperature for 12 h and then filtered through a celite pad, concentrated, and eluted through a silica column to give the desired 2-(phenylethynyl)benzaldehyde (S-1) (0.93 g, 4.5 mmol, 84%).

b) Synthesis of 1-(1-methoxy-3-phenylprop-2-yn-1-yl)-2-(phenylethynyl)benzene (1a)

A THF solution of ethynylbenzene (0.63 g, 6.2 mmol) was cooled to −78° C. n-BuLi (2.5 M in hexane, 2.27 mL, 6.79 mmol) was slowly added to this solution and was stirred for 0.5 h at −78° C. 2-(phenylethynyl)benzaldehyde (S-1) (1.00 g, 4.86 mmol) was added to the resulting solution and was stirred for 1 h at −78° C. Iodomethane (1.00 g, 6.00 mmol) was added to the solution and was stirred for 12 h at room temperature. The reaction was quenched with water (15 mL) and extracted with ethyl acetate (100 mL). The extract was washed with brine solution, dried over MgSO₄, and concentrated under reduced pressure. The residue was eluted through a silica column to afford 1-(1-methoxy-3-phenylprop-2-yn-1-yl)-2-(phenylethynyl)benzene (1a) (1.39 g, 3.39 mmol, 70%) as pale yellow liquid.

Synthetic Scheme (A2) for the Preparation of (1q) and (1r)

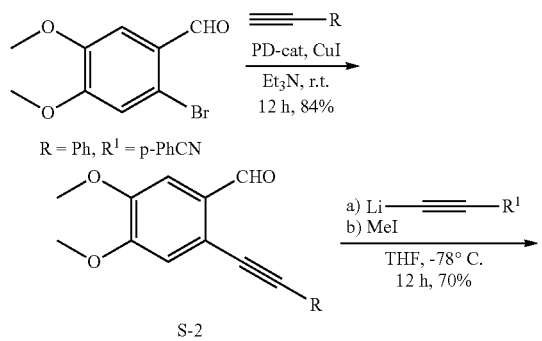

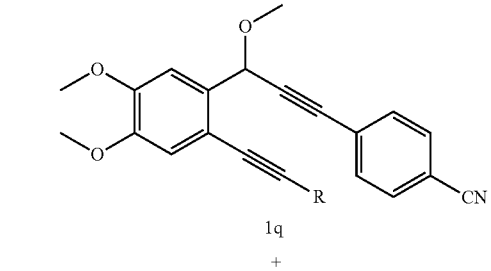

1q

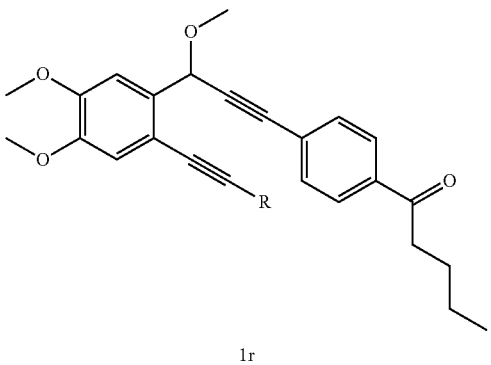

1r a) Synthesis of 4,5-dimethoxy-2-(phenylethynyl)benzaldehyde (S-2)

2-bromo-4,5-dimethoxybenzaldehyde (1.00 g, 4.08 mmol) was added in one portion to a solution of CuI (0.08 g, 10 mol %) in Et₃N (30 mL) and degassed with nitrogen for 15 min at 23° C. Pd(PPh₃)₄ (0.24 g, 5 mol %) was added to the mixture and was stirred for 15 min before being treated with ethynylbenzene (0.46 g, 4.5 mmol) dropwise. The resulting solution was stirred at room temperature for 12 h and then filtered through a celite pad, concentrated, and eluted through a silica column to give the desired 4,5-dimethoxy-2-(phenylethynyl)benzaldehyde (S-2) (0.87 g, 3.26 mmol, 80%).

b) Synthesis of 4-(3-(4,5-dimethoxy-2-(phenylethynyl)phenyl)-3-methoxyprop-1-yn-1-yl)benzonitrile (1q) and 1-(4-(3-(4,5-dimethoxy-2-(phenylethynyl)phenyl)-3-methoxyprop-1-yn-1-yl)phenyl)pentan-1-one (1r)

A THF solution of 4-ethynylbenzonitrile (0.32 g, 2.5 mmol) was cooled to −78° C. n-BuLi (2.5 M in hexane, 1.0 mL, 2.5 mmol) was slowly added to this solution and was stirred for 0.5 h at −78° C. 4,5-dimethoxy-2-(phenylethynyl)benzaldehyde (S-2) (0.60 g, 2.3 mmol) was added to the resulting solution and was stirred for 1 h at −78° C. Iodomethane (0.42 g, 2.9 mmol) was added to the solution and was stirred for 12 h at room temperature. The reaction was quenched with water (15 mL) and extracted with ethyl acetate (100 mL). The extract was washed with brine solution, dried over MgSO₄, and concentrated under reduced pressure. The residue was eluted through a silica column to afford two products, 4-(3-(4,5-dimethoxy-2-(phenylethynyl)phenyl)-3-methoxyprop-1-yn-1-yl)benzonitrile (1q; 40%) and 1-(4-(3-(4,5-dimethoxy-2-(phenylethynyl)phenyl)-3-methoxyprop-1-yn-1-yl)phenyl)pentan-1-one (1r; 17%).

Synthetic Scheme (A3) for the Preparation of (1t)

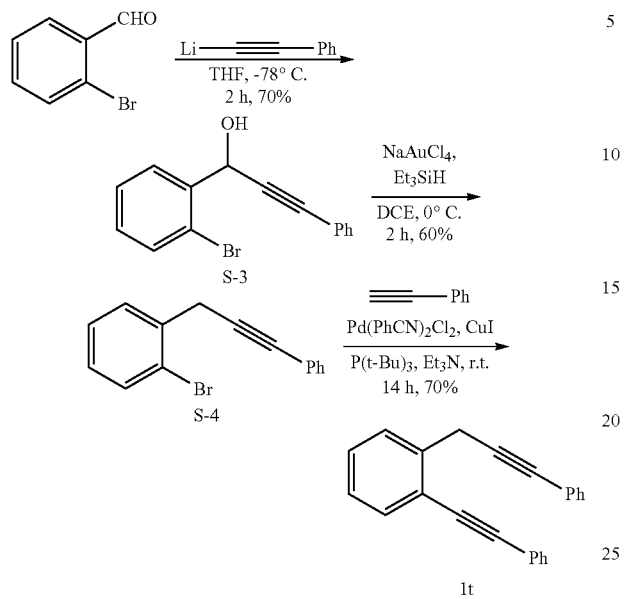

a) Synthesis of 1-(2-bromophenyl)-3-phenylprop-2-yn-1-ol (S-3)

A THF solution of ethynylbenzene (0.60 g, 5.9 mmol) was cooled to −78° C. n-BuLi (2.5 M in hexane, 2.37 mL, 5.90 mmol) was slowly added to this solution and was stirred for 0.5 h at −78° C. 2-bromobenzaldehyde (1.00 g, 5.40 mmol) was added to the resulting solution and was stirred for 2 h slowly allowed to warm to room temperature. The reaction was quenched with saturated NH$_4$Cl solution and extracted with ethyl acetate (2×50 mL). The extract was washed with brine solution, dried over MgSO$_4$, and concentrated under reduced pressure. The residue was eluted through a silica column to afford 1-(2-bromophenyl)-3-phenylprop-2-yn-1-ol (S-3) (1.08 g, 3.78 mmol, 70%) as pale yellow liquid.

b) Synthesis of 1-bromo-2-(3-phenylprop-2-yn-1-yl)benzene (S-4)

A DCE solution of 1-(2-bromophenyl)-3-phenylprop-2-yn-1-ol (0.30 g, 1.0 mmol) was cooled to 0° C. NaAuCl$_4$ (0.04 g, 10 mol %) was slowly added to this solution and was stirred for 2 h at room temperature. The reaction mixture filtered through a small bed of celite, and concentrated under reduced pressure. The residue was eluted through a silica column to afford 1-bromo-2-(3-phenylprop-2-yn-1-yl)benzene (S-4) (0.17 g, 0.60 mmol, 60%) as pale brown liquid.

c) Synthesis of 1-(phenylethynyl)-2-(3-phenylprop-2-yn-1-yl)benzene (1t)

1-bromo-2-(3-phenylprop-2-yn-1-yl)benzene (0.20 g, 0.73 mmol) was added in one portion to a solution of CuI (0.01 g, 10 mol %) in Et$_3$N (30 mL) and degassed with nitrogen for 15 min at 23° C. PdCl$_2$(PhCN)$_2$ (0.03 g, 10 mol %) was added to the mixture and was stirred for 15 min before being treated with ethynylbenzene (0.08 g, 0.7 mmol) dropwise. The resulting solution was stirred at room temperature for 14 h and then filtered through a celite pad, concentrated, and eluted through a silica column to give the desired 1-(phenylethynyl)-2-(3-phenylprop-2-yn-1-yl)benzene (1t) (0.15 g, 0.50 mmol, 70%).

Synthetic Scheme (A4) for the Preparation of Oligoalkynes to Vary Position B-Compounds (1o) and (1e)

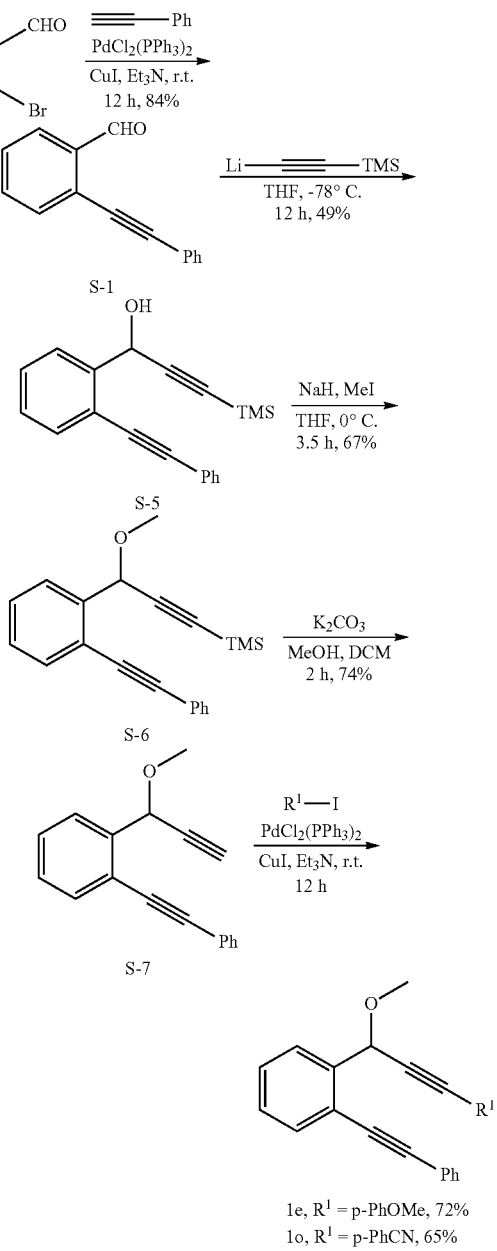

a) Synthesis of 1-(2-(phenylethynyl)phenyl)-3-(trimethylsilyl)prop-2-yn-1-ol (S-5)

A THF solution of ethynyltrimethylsilane (0.77 g, 7.8 mmol) was cooled to −78° C. n-BuLi (2.5 M in hexane, 3.1 mL, 7.8 mmol) was slowly added to this solution and was stirred for 0.5 h at −78° C. 2-(phenylethynyl)benzaldehyde (S-1) (1.32 g, 6.40 mmol) was added to the resulting solution and was stirred for 1 h at −78° C. The reaction was quenched with water (15 mL) and extracted with ethyl acetate (60 mL). The extract was washed with brine solution, dried over $Na_2SO_4$, and concentrated under reduced pressure. The residue was eluted through a silica column to afford 1-(2-(phenylethynyl)phenyl)-3-(trimethylsilyl)prop-2-yn-1-ol (S-5) (0.95 g, 3.1 mmol, 49%).

b) Synthesis of (3-methoxy-3-(2-(phenylethynyl)phenyl)prop-1-yn-1-yl)trimethylsilane (S-6)

A THF solution of 1-(2-(phenylethynyl)phenyl)-3-(trimethylsilyl)prop-2-yn-1-ol (S-5) (0.95 g, 3.1 mmol) was cooled to 0° C. NaH (60% wt/wt in oil, 0.15 g, 3.7 mmol) was added to this solution and was stirred for 0.25 h at 0° C. Iodomethane (0.48 g, 3.4 mmol) was added to the solution and was stirred at 0° C. for 0.5 h. The solution was allowed to warm to room temperature, and was stirred for an additional 3.5 h. The reaction was quenched with water (15 mL) and extracted with ethyl acetate (60 mL). The extract was washed with brine solution, dried over $Na_2SO_4$, and concentrated under reduced pressure. The residue was eluted through a silica column to afford (3-methoxy-3-(2-(phenylethynyl)phenyl)prop-1-yn-1-yl)trimethylsilane (S-6) (0.61 g, 1.9 mmol, 67%).

c) Synthesis of 1-(1-methoxyprop-2-yn-1-yl)-2-(phenylethynyl)benzene (S-7)

To a 3:1 solution of DCM and methanol was added (3-methoxy-3-(2-(phenylethynyl)phenyl)prop-1-yn-1-yl)trimethylsilane (S-6) (0.23 g, 0.73 mmol) at room temperature. $K_2CO_3$ (0.73 g, 5.2 mmol) was added to this solution and was stirred for 2 h at room temperature. The reaction was extracted with ethyl acetate (60 mL). The extract was washed with brine solution, dried over $Na_2SO_4$, and concentrated under reduced pressure. The residue was eluted through a silica column to afford compound 1-(1-methoxyprop-2-yn-1-yl)-2-(phenylethynyl)benzene (S-7) (0.13 g, 0.54 mmol, 74%).

d) Synthesis of 1-(1-methoxy-3-(4-methoxyphenyl)prop-2-yn-1-yl)-2-(phenylethynyl)benzene (1e)

1-iodo-4-methoxybenzene (0.19 g, 0.82 mmol) was added in one portion to a solution of CuI (0.02 g, 10 mol %) in $Et_3N$ (30 mL) and degassed with argon for 15 min at room temperature. $PdCl_2(PPh_3)_2$ (0.03 g, 5 mol %) was added to the mixture and was stirred for 15 min before being treated with 1-(1-methoxyprop-2-yn-1-yl)-2-(phenylethynyl)benzene (S-7) (0.17 g, 0.67 mmol) dropwise. The resulting solution was stirred at room temperature for 14 h and then filtered through a celite pad, concentrated and eluted through a silica column to give the desired 1-(1-methoxy-3-(4-methoxyphenyl)prop-2-yn-1-yl)-2-(phenylethynyl)benzene (1e) (0.17 g, 0.48 mmol, 72%) as pale yellow liquid.

e) Synthesis of 4-(3-methoxy-3-(2-(phenylethynyl)phenyl)prop-1-yn-1-yl)benzonitrile (1o)

Same as 1e using 4-iodobenzonitrile (0.19 g, 0.84 mmol), CuI (0.02 g, 10 mol %), $Et_3N$ (30 mL), $PdCl_2(PPh_3)_2$ (0.03 g, 5 mol %), and 1-(1-methoxyprop-2-yn-1-yl)-2-(phenylethynyl)benzene (S-7) (0.17 g, 0.70 mmol). Yielded 4-(3-methoxy-3-(2-(phenylethynyl)phenyl)prop-1-yn-1-yl)benzonitrile (1o) (0.16 g, 0.45 mmol, 65%).

Synthetic Scheme (A5) for the Preparation of Oligoalkynes to Vary Position C-Compound (1h)

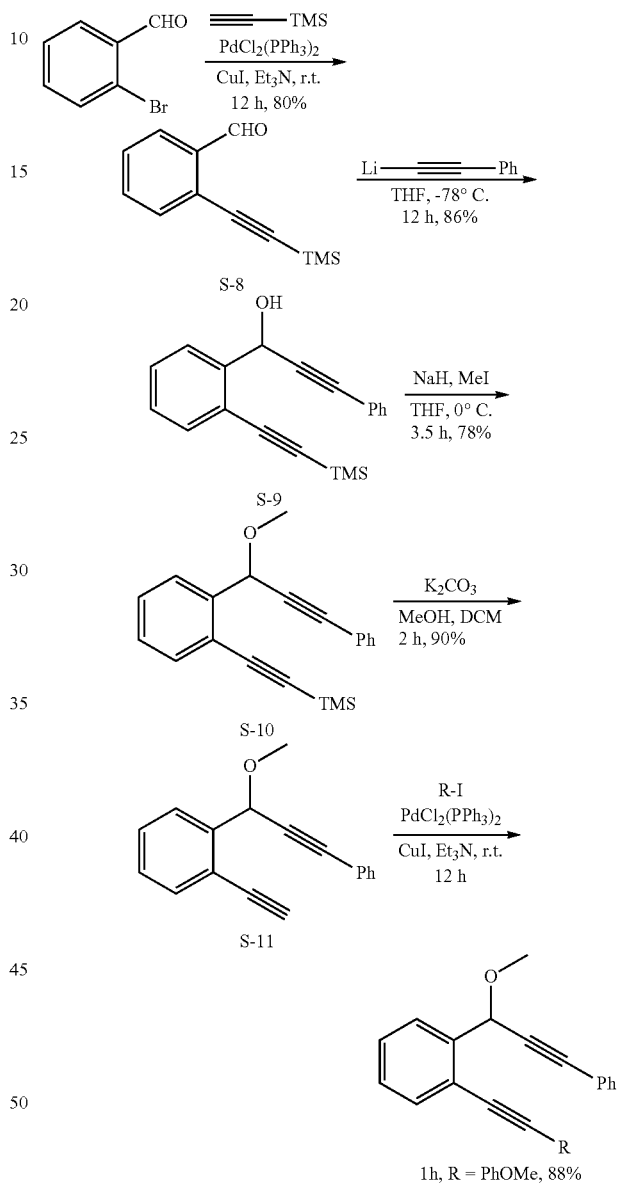

a) Synthesis of 2-((trimethylsilyl)ethynyl)benzaldehyde (S-8)

2-bromobenzaldehyde (1 g, 5.4 mmol) was added in one portion to a solution of CuI (0.103 g, 10 mol %) in $Et_3N$ (20 mL) and degassed with nitrogen for 20 min at 23° C. $Pd(PPh_3)_2Cl_2$ 0.189 g, 5 mol %) was added to the mixture and was stirred for 10 min before being treated with ethynyltrimethylsilane (0.637 g, 6.48 mmol) dropwise. The resulting solution was stirred at room temperature for 12 h and then filtered through a celite pad, concentrated, and eluted through a silica column to give the desired 2-((trimethylsilyl)ethynyl)benzaldehyde (S-8) (0.875 g, 4.32 mmol, 80%).

b) Synthesis of 3-phenyl-1-(2-((trimethylsilyl)ethynyl)phenyl)prop-2-yn-1-ol (S-9)

Same as S-5 using ethynylbenzene (0.13 mL, 1.18 mmol), n-BuLi (2.5 M in hexane, 0.44 mL g, 1.08 mmol), 2-((trimethylsilyl)ethynyl)benzaldehyde (S-8) (0.2 g, 0.988 mmol). Yielded 3-phenyl-1-(2-((trimethylsilyl)ethynyl)phenyl)prop-2-yn-1-ol (S-9) (0.259 g, 0.851 mmol, 86%).

c) Synthesis of ((2-(1-methoxy-3-phenylprop-2-yn-1-yl)phenyl)ethynyl)trimethylsilane (5-10)

Same as S-6 using 3-phenyl-1-(2-((trimethylsilyl)ethynyl)phenyl)prop-2-yn-1-ol (S-9) (0.259 g, 0.851 mmol), e) Synthesis of 1-(1-methoxy-3-phenylprop-2-yn-1-yl)-2-((4-ethoxyphenyl)ethynyl)benzene (1h)

Same as be using S-11 (0.133 g, 0.539 mmol), CuI (0.010 g, 10 mol %), Et$_3$N (5 mL), PdCl$_2$(PPh$_3$)$_2$ (0.019 g, 5 mol %), and 4-iodoanisole (0.139 g, 0.593 mmol). Yielded Synthesis of 1-(1-methoxy-3-phenylprop-2-yn-1-yl)-2-(4-ethoxyphenyl)ethynyl)benzene (1h) (0.168 g, 0.476 mmol, 88%).

Synthetic Scheme (A6) for the Preparation of 1-(4,5-dimethoxy-2-((2-(phenylethynyl)phenyl)ethynyl)phenyl)-3-(2-(phenylethynyl)phenyl)prop-2-yn-1-ol

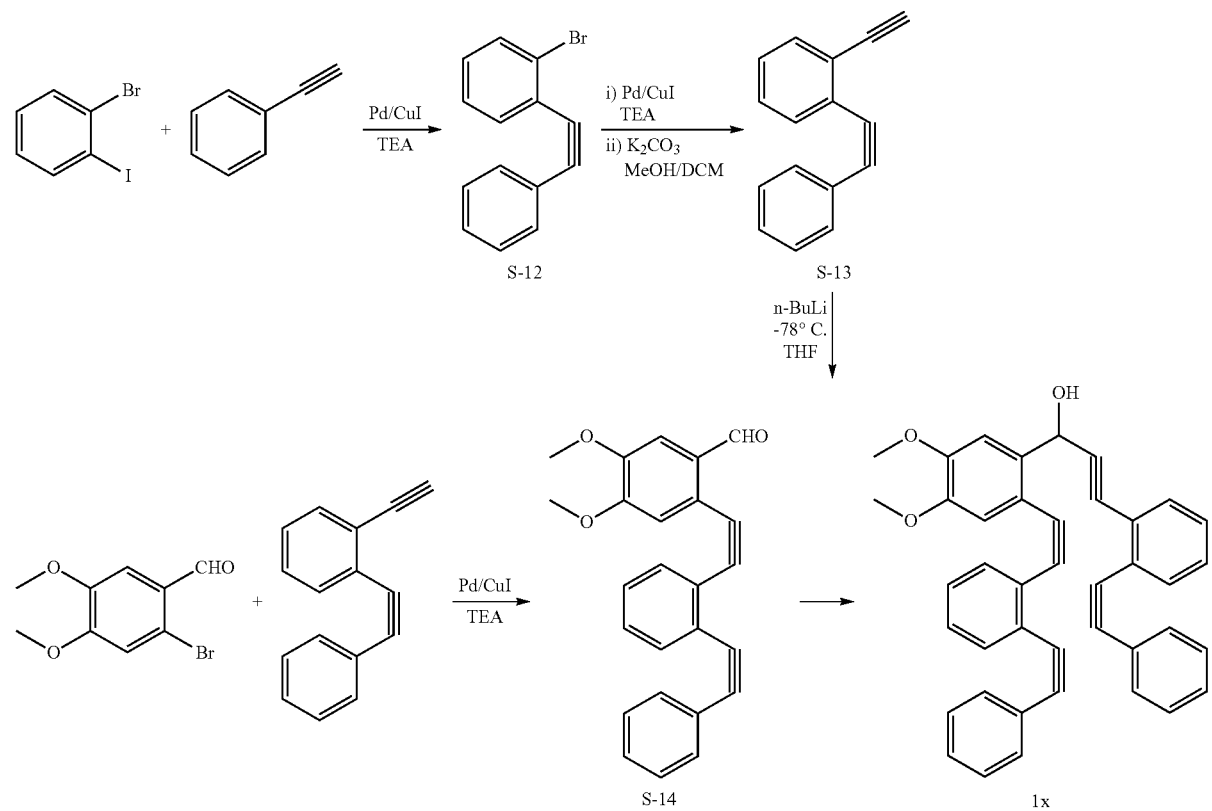

NaH (60% wt/wt in oil, 0.041 g, 1.02 mmol), and iodomethane (0.145 g, 1.02 mmol). Yielded ((2-(1-methoxy-3-phenylprop-2-yn-1-yl)phenyl)ethynyl)trimethylsilane (S-10) (0.246 g, 0.771 mmol, 78%).

d) Synthesis of 1-ethynyl-2-(1-methoxy-3-phenylprop-2-yn-1-yl)benzene (S-11)

Same as S-7 using ((2-(1-methoxy-3-phenylprop-2-yn-1-yl)phenyl)ethynyl)trimethylsilane (S-10) (0.246 g, 0.771 mmol) and K$_2$CO$_3$ (0.746 g, 5.4 mmol). Yielded 1-ethynyl-2-(1-methoxy-3-phenylprop-2-yn-1-yl)benzene (S-11) (0.188 g, 0.763 mmol, 90%).

Synthesis of 1-bromo-2-(phenylethynyl)benzene (S-12)

2-bromoiodobenzene (1.00 g, 3.53 mmol) was added in one portion to a solution of CuI (0.07 g, 10 mol %) in Et$_3$N (30 mL) and degassed with nitrogen for 15 min at 23° C. PdCl$_2$(PPh$_3$)$_2$ (0.12 g, 5 mol %) was added to the mixture and was stirred for 15 min before being treated with ethynylbenzene (0.40 g, 3.88 mmol) dropwise. The resulting solution was stirred at room temperature for 12 h and then filtered through a celite pad, concentrated, and eluted through a silica column to give the desired synthesis of 1-bromo-2-(phenylethynyl)benzene (S-12) (0.80 g, 3.14 mmol, 89%).

Synthesis of 1-ethynyl-2-(phenylethynyl)benzene (S-13)

Same as general procedure S-7, trimethyl((2-(phenylethynyl)phenyl)ethynyl)silane (0.500 g, 1.82 mmol) and K$_2$CO$_3$ (0.276 g, 2.0 mmol). Yielded 1-ethynyl-2-(phenylethynyl)benzene (S-13) (0.33 g, 1.64 mmol, 90%).

Synthesis of 4,5-dimethoxy-2-((2-(phenylethynyl)phenyl)ethynyl)benzaldehyde (S-14)

Same as general procedure S-1, using 2-bromo-4,5-dimethoxybenzaldehyde (0.250 g, 0.10 mmol) and 1-ethynyl-2-(phenylethynyl)benzene (0.23 g, 0.12 mmol) yielded 4,5-dimethoxy-2-((2-(phenylethynyl)phenyl)ethynyl)benzaldehyde S-14 (0.26 g, 0.71 mmol, 70%).

Synthesis of 3 1-(4,5-dimethoxy-2-((2-(phenylethynyl)phenyl)ethynyl)phenyl)-3-(2-(phenylethynyl)phenyl)prop-2-yn-1-ol (1v)

Same as general procedure S-1, 1-ethynyl-2-(phenylethynyl)benzene (0.182 g, 0.90 mmol) and 4,5-dimethoxy-2-((2-(phenylethynyl)phenyl)ethynyl)benzaldehyde (0.300 g, 0.81 mmol yielded 1-(4,5-dimethoxy-2-((2-(phenylethynyl)phenyl)ethynyl)phenyl)-3-(2-(phenylethynyl)phenyl)prop-2-yn-1-ol (1v) (0.42 g, 0.73 mmol, 90%) as pale yellow semisolid.

Oxidative Dimerization of (2b) to Prepare 3,3'-dimethoxy-11,11'-diphenyl-11H,11'H-4,4'-bibenzo[a]fluorene (7):

To a flame dried round-bottom flask that was flushed with nitrogen, (2b, 0.03 g, 0.093 mmol) was added using dry DCM and then cooled to 0° C. 2,3-Dichloro-5,6-dicyano-1,4-benzoquinone (0.025 g, 0.11 mmol) was then added, color changed from clear yellow to brown, and stirred for 5 min. 2 drops of trifluoromethanesulfonic acid was added, color changed from brown to dark green, and the reaction mixture stirred for 2 hours. The reaction mixture was quenched with water, washed with sodium bicarbonate solution, and extracted with DCM two times. The solvent was evaporated and concentrated. A preparatory silica plate was used for purification which afforded (5, 0.012 g, 40% yield) as beige crystals.

General Procedure for the Synthesis of 11-phenyl-11H-benzo[a]fluorene (2a)

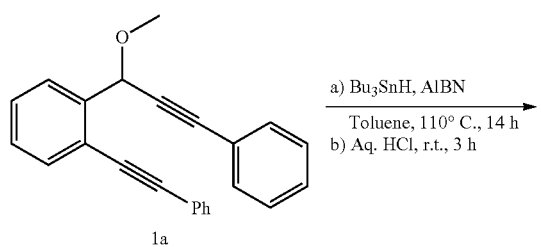

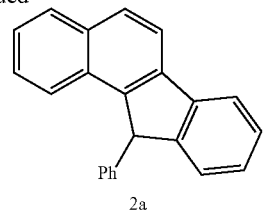

A toluene solution of 1-(1-methoxy-3-phenylprop-2-yn-1-yl)-2-(phenylethynyl)benzene (1a) (0.10 g, 0.22 mmol) was fitted with a condenser and degassed by purging with argon gas. AIBN (0.01 g, 0.06 mmol) and Bu$_3$SnH (0.09 g, 0.3 mmol) were dissolved separately in dry toluene and added slowly (flow rate 1 mL/hr) to the reaction mixture by using a syringe pump at 110° C., and the reaction was monitored by TLC. After consumption of the starting material, the reaction mixture was allowed to cool down to room temperature and filtered through a small celite bed. Solvent was removed under reduced pressure. The crude reaction mixture was dissolved in 20 mL DCM. Aq. HCl (2 M) (15 mL) was added to above mixture and stirred for 3 h. The reaction mixture was extracted with DCM (30 mL). The extract was washed with brine solution, dried over Na$_2$SO$_4$, and concentrated under reduced pressure. The residue was eluted through a silica column to afford compound purified by column chromatography over silica gel, which yielded 11-phenyl-11H-benzo[a]fluorene (2a) (0.06 g, 0.2 mmol, 86%).

Spectral Data:

NMR spectra were recorded on Bruker 400 and 600 MHz and Varian 500 MHz instruments and calibrated using residual undeuterated solvents as an internal reference. δ is in ppm, J is the coupling constant and is expressed in Hz. The following abbreviations were used to explain multiplicities: s=singlet, d=doublet, t=triplet, q=quartet, dd=doublet of doublet, m=multiplet, quin=quintuplet, sext=sextet, sep=septet, br=broad. All NMR spectra were run at 600/400 MHz ($^1$HNMR) or 150/100 MHz ($^{13}$CNMR) in CDCl$_3$ solution.

1-(1-methoxy-3-phenylprop-2-yn-1-yl)-2-(phenylethynyl)benzene (1a)

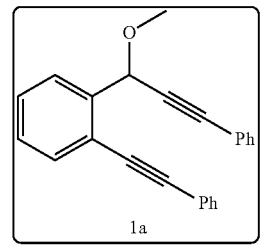 [SMILES: COC(C#Cc1ccccc1)c1ccccc1C#Cc1ccccc1]

Synthetic Scheme A1, 70% yield. Pale yellow thick syrup; IR (neat, cm-1): 3090, 3020, 2850, 2150, 1580, 1240, 1075, 700; $^1$H-NMR (400 MHz, CDCl$_3$): δ 7.84 (dd, J=1.2 Hz, 6.6 Hz, 1H), 7.60-7.58 (m, 3H), 7.51-7.49 (m, 2H), 7.44-7.31 (m, 8H), 5.84 (s, 1H), 3.61 (s, 3H); $^{13}$C-NMR (100 MHz, CDCl$_3$): δ 140.1, 132.2, 131.8 (2×CH), 131.5 (2×CH), 128.7, 128.5, 128.4, 128.39 (2×CH), 128.34, 128.2 (2×CH), 127.3, 123.0, 122.5, 122.4, 94.2, 87.2, 86.8, 86.6, 71.6, 56.9; HRMS calcd for C$_{24}$H$_{18}$O: 322.1357. found: 323.1363.

4-methoxy-2-(1-methoxy-3-phenylprop-2-yn-1-yl)-1-(phenylethynyl)benzene (1b)

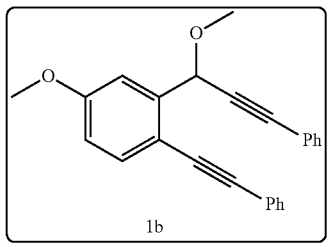 [SMILES: COc1ccc(C#Cc2ccccc2)c(C(C#Cc2ccccc2)OC)c1]

Synthetic Scheme A1, 70% yield. Light orange liquid; IR (neat, cm-1): 3059, 2933, 2820, 2213, 1497, 1290, 1222, 1077, 753; $^1$H-NMR (400 MHz, CDCl$_3$): δ 7.57-7.54 (m, 2H), 7.52-7.46 (m, 3H), 7.39-7.30 (m, 7H), 6.88 (d, J=8.6 Hz, 1H), 5.79 (s, 1H), 3.87 (s, 3H), 3.60 (s, 3H); $^{13}$C-NMR (150 MHz, CDCl$_3$): δ 159.9, 141.9, 133.5, 131.7 (2×CH), 131.3 (2×CH), 128.4, 128.3 (2×CH), 128.2 (2×CH), 128.1, 123.4, 122.5, 114.5, 114.4, 112.4, 92.8, 87.1, 86.8, 86.6, 71.5, 57.0, 55.3; HRMS calcd for C$_{25}$H$_{20}$O$_2$: 352.1458. found: [M+NH$_4$]$^+$=370.1794.

1,2-dimethoxy-4-(1-methoxy-3-phenylprop-2-yn-1-yl)-5-(phenylethynyl)benzene (1c)

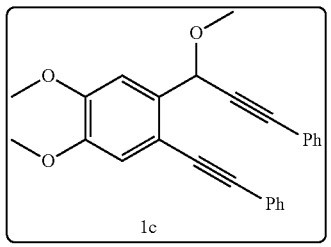 [SMILES: COc1cc(C#Cc2ccccc2)c(C(C#Cc2ccccc2)OC)cc1OC]

Synthetic Scheme A1, 81% yield. IR (neat, cm-1): 3065, 2933, 2852, 2208, 1513, 1248, 1210, 1090, 755; $^1$H-NMR (400 MHz, CDCl$_3$): δ 7.57-7.54 (m, 2H), 7.48-7.45 (m, 2H), 7.38-7.34 (m, 3H), 7.33-7.29 (m, 4H), 7.04 (s, 1H), 5.76 (s, 1H), 3.95 (s, 3H), 3.92 (s, 3H), 3.56 (s, 3H); $^{13}$C-NMR (150 MHz, CDCl$_3$): δ 149.7, 148.6, 133.7, 131.7 (2×CH), 131.3 (3×CH), 128.4, 128.3 (2×CH), 128.2 (2×CH), 123.2, 122.5, 114.5, 114.0, 110.0, 92.8, 87.0 (2×C), 86.8, 71.3, 56.8, 56.0, 55.9; HRMS calcd for C$_{26}$H$_{22}$O$_3$: 382.1563. found: [M-OCH$_3$]$^+$=351.1380.

5-(1-methoxy-3-phenylprop-2-yn-1-yl)-6-(phenylethynyl)benzo[d][1,3]dioxole (1d)

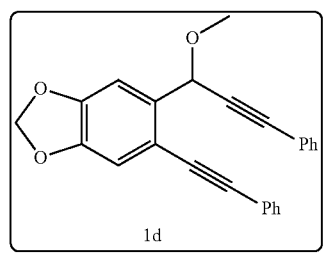 [SMILES: COC(C#Cc1ccccc1)c1cc2c(cc1C#Cc1ccccc1)OCO2]

Synthetic Scheme A1, 80% yield. Pale yellow syrup; IR (neat, cm-1): 3100, 3020, 2860, 2210, 1540, 1220, 940; $^1$H-NMR (400 MHz, CDCl$_3$): δ 7.62-7.60 (m, 2H), 7.55-7.53 (m, 2H), 7.41-7.33 (m, 7H), 7.06 (s, 1H), 6.00 (s, 2H), 5.86 (s, 1H), 3.62 (s, 3H); $^{13}$C-NMR (100 MHz, CDCl$_3$): δ 148.2, 147.3, 135.4, 131.6 (2×CH), 131.3 (2×CH), 128.4, 128.2 (2×CH), 128.2, 128.1 (2×CH), 123.0, 122.3, 115.6, 111.1, 107.8, 101.5, 92.7, 86.9, 86.8, 86.7, 71.2, 56.6; HRMS calcd for C$_{25}$H$_{18}$O$_3$: 366.1255. found: 366.1235.

1-(1-methoxy-3-(4-methoxyphenyl)prop-2-yn-1-yl)-2-(phenylethynyl)benzene (1e)

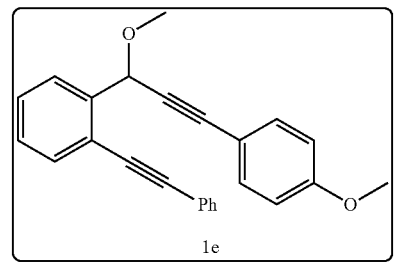 [SMILES: COc1ccc(C#CC(OC)c2ccccc2C#Cc2ccccc2)cc1]

Synthetic Scheme A4, 72% yield. Pale yellow thick syrup; IR (neat, cm-1): 3060, 2926, 2854, 2220, 1605, 1571, 1444, 1509, 1250, 1173; $^1$H-NMR (600 MHz, CDCl$_3$): δ 7.82 (d, J=7.8 Hz, 1H), 7.57 (d, J=7.6, 3H), 7.43-7.39 (m, 3H), 7.38-7.32 (m, 4H), 6.83 (d, J=8.7 Hz, 2H), 5.79 (s, 1H), 3.81 (s, 3H), 3.58 (s, 3H); $^{13}$C-NMR (150 MHz, CDCl$_3$): δ 159.7, 140.6, 133.4 (2×CH), 132.3, 131.7 (2×CH), 128.9, 128.6, 128.6 (2×CH), 128.4, 127.6, 123.3, 122.7, 114.9, 114.0 (2×CH), 94.4, 87.4, 87.1, 85.5, 71.9, 57.1, 55.4; HRMS calcd for C$_{25}$H$_{20}$O$_2$: 352.1463. found: [M+NH$_4$]$^+$= 370.1804.

1-(1-methoxy-3-phenylprop-2-yn-1-yl)-2-(phenylethynyl)naphthalene (1f)

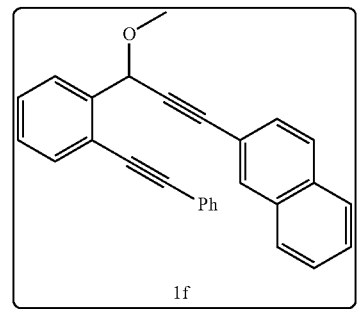 [SMILES: COC(C#Cc1ccc2ccccc2c1)c1ccccc1C#Cc1ccccc1]

Synthetic Scheme A1, 70% yield. Pale yellow liquid; IR (neat, cm-1): 3050, 2952, 2832, 1560, 1350, 840, 2150, 1580, 1415, 1230 1100; $^1$H-NMR (400 MHz, CDCl$_3$): δ 8.01 (s, 1H) 7.88 (d, J=7.2 z, 1H), 7.82-7.76 (m, 3H), 7.62-7.59 (m, 3H), 7.54-7.40 (m, 4H), 7.39-7.34 (m, 4H), 5.87 (s, 1H), 3.64 (s, 3H); $^{13}$C-NMR (100 MHz, CDCl$_3$): δ 140.2, 132.8, 132.2, 131.7, 131.6 (2×CH), 128.8, 128.5, 128.4 (3×CH), 128.3, 127.9, 127.7 (3×CH), 127.4, 126.7, 126.5, 123.1, 122.5, 119.8, 94.3, 87.6, 87.0, 86.9, 71.7, 57.0; HRMS calcd for C$_{28}$H$_{20}$O: 372.1514. found: 372.1534.

1-(1-methoxy-3-phenylprop-2-yn-1-yl)-2-((4-(trifluoromethyl)phenyl)ethynyl)benzene (1g)

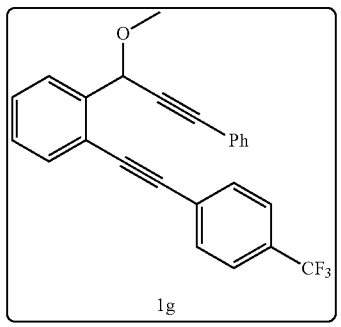 [SMILES: COC(C#Cc1ccccc1)c1ccccc1C#Cc1ccc(C(F)(F)F)cc1]

Synthetic Scheme A1, 72% yield. Pale brown syrup; IR (neat, cm-1): 3054, 3010, 2860, 2180, 2100, 1540, 1360, 1210, 1090; $^1$H-NMR (400 MHz, CDCl$_3$): δ 7.90 (d, J=7.7 Hz, 1H), 7.72-7.63 (m, 5H), 7.54-7.49 (m, 3H), 7.42-7.35 (m, 4H), 5.84 (s, 1H), 3.65 (s, 3H); $^{13}$C-NMR (100 MHz, CDCl$_3$): δ 140.4, 132.4, 131.7 (4×CH), 129.3, 128.5, 128.4, 128.3 (2×CH), 128.2, 126.9, 125.3 (q, J=7.7 Hz), 122.4, 121.7, 92.7, 89.2, 87.5, 86.4, 71.6, 56.8 (2 carbon peaks merge with other peaks); HRMS calcd for C$_{25}$H$_{17}$F$_3$O: 390.1231. found: 390.1213.

1-(1-methoxy-3-phenylprop-2-yn-1-yl)-2-((4-methoxyphenyl)ethynyl)benzene (1h)

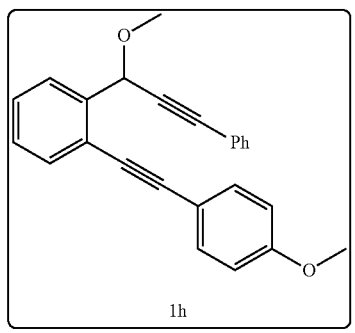 [SMILES: COc1ccc(C#Cc2ccccc2C(C#Cc2ccccc2)OC)cc1]

Synthetic Scheme A5, 88% yield. Light yellow liquid; IR (neat, cm-1): 3064, 2930, 2840, 2214, 1510, 1245, 1077, 753; $^1$H-NMR (400 MHz, CDCl$_3$): δ 7.82 (d, J=8.9 Hz, 1H), 7.56 (d, J=8.8 Hz, 1H), 7.52-7.47 (m, 4H), 7.39 (t, J=7.6 Hz, 1H), 7.35-7.29 (m, 4H), 6.9 (d, J=8.8 Hz, 2H), 5.81 (s, 1H), 3.84 (s, 3H), 3.59 (s, 3H); $^{13}$C-NMR (100 MHz, CDCl$_3$): δ 159.7, 139.9, 133.0 (3×CH), 132.0, 131.7 (2×CH), 128.4, 128.3, 128.2 (2×CH), 127.3, 122.8, 122.6, 115.2, 114.0 (2×CH), 94.3, 87.2, 86.7, 85.5, 71.6, 56.9, 55.3; HRMS calcd for C$_{25}$H$_{20}$O$_2$: 352.1451. found: [M+NH$_4$]$^+$= 370.1802.

1-(hex-1-yn-1-yl)-2-(1-methoxy-3-(4-methoxyphenyl)prop-2-yn-1-yl)benzene (1i)

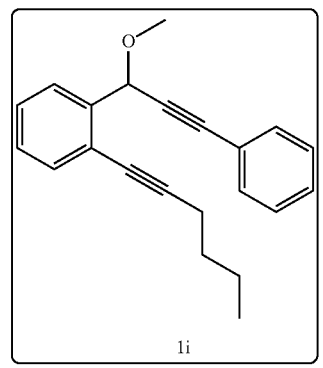 [SMILES: CCCCC#Cc1ccccc1C(C#Cc1ccccc1)OC]

Synthetic Scheme A1, 55% yield. Pale yellow thick syrup; IR (neat, cm-1): 3062, 2925, 2855, 2225, 1598, 1571, 1490, 1464, 1189; $^1$H-NMR (600 MHz, CDCl$_3$): δ 7.75 (d, J=7.6 Hz, 1H), 7.48-7.44 (m, 2H), 7.38 (d, J=7.6 Hz, 1H), 7.36-7.23 (m, 5H), 5.76 (s, 1H), 3.57 (s, 3H), 2.51 (t, J=7.0 Hz, 2H), 1.68-1.58 (m, 2H), 1.56-1.46 (m, 2H), 0.98 (t, J=7.3 Hz, 3H); $^{13}$C-NMR (150 MHz, CDCl$_3$): δ 139.9, 132.1, 131.7 (2×CH), 128.4, 128.17 (2×CH), 128.15, 127.9, 127.2, 123.3, 122.6, 95.5, 87.0, 86.9, 78.0, 71.4, 56.7, 30.8, 22.0, 19.2, 13.6; HRMS calcd for C$_{22}$H$_{22}$O: 302.1671. found: [M+NH4]$^+$=320.2012.

4-fluoro-2-(1-methoxy-3-phenylprop-2-yn-1-yl)-1-(phenylethynyl)benzene (1j)

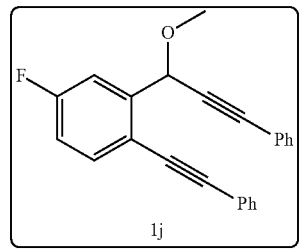 [SMILES: COC(C#Cc1ccccc1)c1cc(F)ccc1C#Cc1ccccc1]

Synthetic Scheme A1, 74% yield. Pale yellow liquid; IR (neat, cm-1): 3060, 3020, 2860, 2160, 1520, 1320, 1220, 1090; $^1$H-NMR (400 MHz, CDCl$_3$): δ 8.62-8.60 (m, 1H), 8.13-8.10 (m, 1H), 7.66-7.64 (m, 2H), 7.48-7.46 (m, 2H), 7.42-7.26 (m, 7H), 5.79 (d, J=1.6 Hz, 1H), 3.61 (t, J=1.8 Hz, 3H); $^{13}$C-NMR (100 MHz, CDCl$_3$): δ149.8 (2×C), 142.2, 136.7, 135.0, 132.0 (3×CH), 131.8 (2×CH), 129.2, 128.7, 128.5 (2×CH), 128.3 (2×CH), 123.2, 122.6 (d, J=1.6 Hz), 94.0, 87.8, 86.3, 85.7, 70.7, 57.1; HRMS calcd for C$_{24}$H$_{17}$FO: 340.1263. found: 340.1253.

4-fluoro-1-(1-methoxy-3-phenylprop-2-yn-1-yl)-2-(phenylethynyl)benzene (1k)

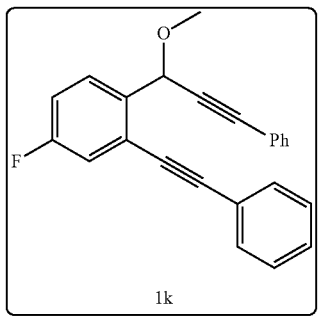 [SMILES: COC(C#Cc1ccccc1)c1ccc(F)cc1C#Cc1ccccc1]

Synthetic Scheme A1, 41% yield. Pale yellow thick syrup; IR (neat, cm-1): 3061, 2927, 2821, 2217, 1606, 1580, 1490, 1444, 1185, 1078; $^1$H-NMR (400 MHz, CDCl$_3$): δ 7.79 (dd, J=8.7, 5.8 Hz, 1H), 7.59-7.55 (m, 2H), 7.49-7.46 (m, 2H), 7.38 (t, J=3.2 Hz, 3 H), 7.34-7.29 (m, 3H), 7.26 (dd, J=9.1, 2.8 Hz, 1H), 7.10 (t, J=8.5 Hz, 1H), 5.75 (s, 1H), 3.58 (s, 3H); $^{13}$C-NMR (150 MHz, CDCl$_3$): δ 162.1 (d, $J_{CF}$=249.0 Hz), 136.3 (d, $J_{CF}$=2.7 Hz), 131.7 (2×CH), 131.6 (2×CH), 129.4, 129.3, 128.8, 128.5, 128.4 (2×CH), 128.2 (2×CH), 124.3 (d, $J_{CF}$=9.9 Hz), 122.5 (d, $J_{CF}$=19.8 Hz), 118.6 (d, $J_{CF}$=23.3 Hz), 116.0 (d, $J_{CF}$ 21.7 Hz), 95.1, 87.5, 86.4, 85.7 (d, $J_{CF}$=2.9 Hz), 71.0, 56.9; HRMS calcd for C$_{24}$H$_{17}$FO: 340.1263. found: [M+NH4]$^+$=358.1610.

3-(1-methoxy-3-phenylprop-2-yn-1-yl)-2-(phenylethynyl)pyridine (1l)

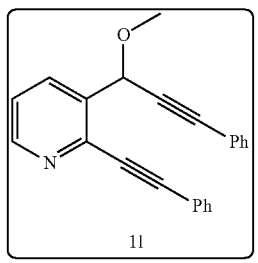 [SMILES: COC(C#Cc1ccccc1)c1cccnc1C#Cc1ccccc1]

Synthetic Scheme A1, 84% yield. Pale yellow semisolid; IR (neat, cm-1): 2990, 2303, 2110, 1737, 1220, 860, 743; $^1$H-NMR (400 MHz, CDCl$_3$): δ 7.58-7.29 (m, 12H), 7.08-7.03 (m, 1H), 5.77 (s, 1H), 3.61 (s, 3H); $^{13}$C-NMR (100 MHz, CDCl$_3$): δ 163.8, 161.4, 143.0, 134.0, 131.8, 131.5, 128.6, 128.4 (2×CH), 128.2 (2×CH), 122.9, 122.2, 118.3, 115.7, 114.7, 114.5, 94.0, 87.5, 85.9, 85.8, 71.2, 57.0; HRMS calcd for C$_{23}$H$_{17}$NO: 323.1310. found [M+H]$^+$: 324.1386.

4-chloro-2-(1-methoxy-3-phenylprop-2-yn-1-yl)-1-(phenylethynyl)benzene (1m)

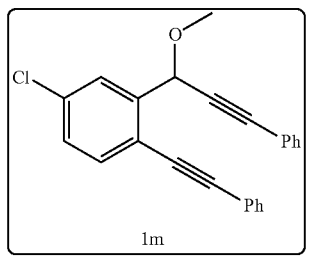 [SMILES: COC(C#Cc1ccccc1)c1cc(Cl)ccc1C#Cc1ccccc1]

Synthetic Scheme A1, 66% yield. Yellow liquid; IR (neat, cm-1): 3065, 2927, 2856, 2220, 1494, 1100, 1077, 753; $^1$H-NMR (400 MHz, CDCl$_3$): 7.79 (d, J=2 Hz, 1H), 7.57-7.55 (m, 2H), 7.51-7.46 (m, 3H), 7.38-7.36 (m, 3H), 7.33-7.30 (m, 4H), 5.74 (s, 1 H), 3.59 (s, 3H); $^{13}$C-NMR (150 MHz, CDCl$_3$): δ 142.0, 134.7, 133.3, 131.8 (2×CH), 131.5 (2×CH), 128.7, 128.6, 128.5, 128.4 (2×CH), 128.2 (2×CH), 127.6, 122.8, 122.3, 120.8, 95.2, 87.6, 85.9, 85.8, 71.1, 57.0, 29.7 (grease); HRMS calcd for C$_{24}$H$_{17}$ClO: 356.0967. found: [M+NH$_4$]$^+$=374.1313.

1-(1-methoxy-3-(4-(trifluoromethyl)phenyl)prop-2-yn-1-yl)-2-(phenylethynyl)benzene (1n)

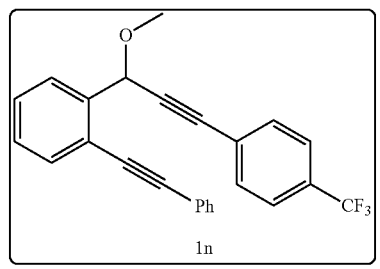 [SMILES: COC(C#Cc1ccc(C(F)(F)F)cc1)c1ccccc1C#Cc1ccccc1]

Synthetic Scheme A4, 73% Yield. Pale yellow thick syrup; IR (neat, cm-1): 3061, 2923, 2853, 2223, 1615, 1599, 1490, 1463, 1167, 1272, 1128, 1067; $^1$H-NMR (400 MHz, CDCl$_3$): δ 7.79 (d, J=8.1 Hz, 1H), 7.61-7.55 (m, 7H), 7.43-7.5 (t, J=7.5 Hz, 1H), 7.40-7.33 (m, 4H), 5.81 (s, 1H), 3.60 (s, 3H); $^{13}$C-NMR (150 MHz, CDCl$_3$): δ 139.8, 132.3, 132.0 (2×CH), 131.5 (3×CH), 128.9, 128.6, 128.5, 128.4 (3×CH), 128.4, 127.2, 126.4, 125.2 (q, $J_{CF}$=7.0 Hz, 3.7 Hz), 123.0, 122.5, 94.5, 89.4, 86.7, 85.8, 71.5, 57.1; HRMS calcd for C$_{25}$H$_{17}$F$_3$O: 390.1231. found: [M+NH$_4$]$^+$=408.1578.

4-(3-methoxy-3-(2-(phenylethynyl)phenyl)prop-1-yn-1-yl)benzonitrile (1o)

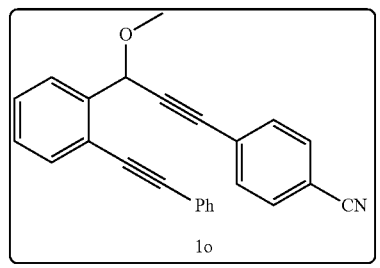 [SMILES: COC(C#Cc1ccc(C#N)cc1)c1ccccc1C#Cc1ccccc1]

Synthetic Scheme A4, 65% yield. Pale orange thick syrup; IR (neat, cm-1): 3060, 2930, 2822, 2250, 2229, 1603, 1571, 1495, 1446, 1179; $^1$H-NMR (400 MHz, CDCl$_3$): δ 7.77 (d, J=8.0 Hz, 1H), 7.61-7.56 (m, 5H), 7.55-7.52 (d, J=8.7 Hz, 2H), 7.43 (t, J=7.3 Hz, 1H), 7.40-7.34 (m, 4H), 5.82 (s, 1H), 3.59 (s, 3H); $^{13}$C-NMR (100 MHz, CDCl$_3$): δ 139.5, 132.3, 132.2 (2×CH), 131.9 (2×CH), 131.5 (2×CH), 128.8, 128.6, 128.5, 128.4 (2×CH), 127.4, 127.1, 122.9, 122.4, 118.3, 111.8, 94.6, 91.4, 86.6, 85.4, 71.5, 57.1; HRMS calcd for C$_{25}$H$_{17}$NO: 347.1310. found: [M+NH$_4$]$^+$=365.1658.

1-(3-(4-fluorophenyl)-1-methoxyprop-2-yn-1-yl)-2-(phenylethynyl)benzene (1p)

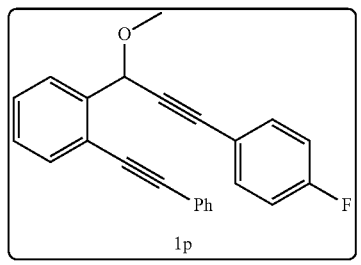 [SMILES: COC(C#Cc1ccc(F)cc1)c1ccccc1C#Cc1ccccc1]

Synthetic Scheme A1, 82% yield. Pale brown liquid; IR (neat, cm-1): 3090, 3010, 2860, 2140, 1520, 1310, 1120; ¹H-NMR (400 MHz, CDCl₃): δ 7.92 (dd, J=1.0, 6.7 Hz, 1H), 7.68-7.65 (m, 3H), 7.53-7.50 (m, 3H), 7.49-7.39 (m, 4H), 7.04 (t, J=8.7 Hz, 2H), 5.91 (s, 1H), 3.68 (s, 3H); ¹³C-NMR (100 MHz, CDCl₃): δ 163.6, 161.1, 140.0, 133.5 (d, J=8.2 Hz) 133.5, 132.0, 131.4 (2×CH), 131.2, 128.6, 128.4, 128.3 (2×CH), (d, J=5.1 Hz) 127.1, 122.9, 122.3, 118.5 (d, J=3.4 Hz), 115.3 (d, J=21.9 Hz), 94.2, 86.7, 86.4, 86.0, 71.4, 56.7; HRMS calcd for C₂₄H₁₇FO: 340.1263. found: 340.1077.

4-(3-(4,5-dimethoxy-2-(phenylethynyl)phenyl)-3-methoxyprop-1-yn-1-yl)benzonitrile (1q)

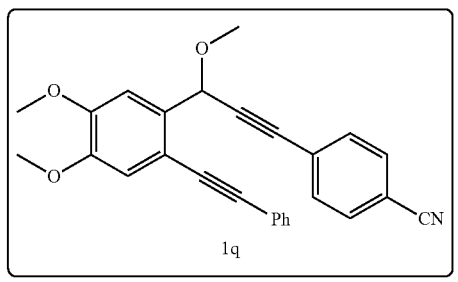 [SMILES: COc1cc(C#Cc2ccccc2)c(C(C#Cc2ccc(C#N)cc2)OC)cc1OC]

Pale brown liquid; IR (neat, cm-1): 3080, 3020, 2860, 2220, 2190, 1520, 1340, 1150, 1020; ¹H-NMR (400 MHz, CDCl₃): δ 7.54-7.47 (m, 6H), 7.33-7.31 (m, 3H), 7.22 (s, 1H), 7.03 (s, 1H), 5.75 (s, 1H), 3.91 (s, 3H), 3.87 (s, 3H), 3.54 (s, 3H); ¹³C-NMR (100 MHz, CDCl₃): δ 149.6, 148.6, 132.8, 131.9 (2×CH), 131.7 (2×CH), 131.1 (2×CH), 128.2 (2×CH), 128.1, 127.1, 122.8, 118.0, 114.1, 113.9, 111.5, 109.5, 92.9, 91.4, 86.5, 84.9, 71.0, 56.8, 55.8, 55.7; HRMS calcd for C₂₇H₂₁NO₃: 407.1521. found: 407.1512.

1-(4-(3-(4,5-dimethoxy-2-(phenylethynyl)phenyl)-3-methoxyprop-1-yn-1-yl)phenyl)pentan-1-one (1r)

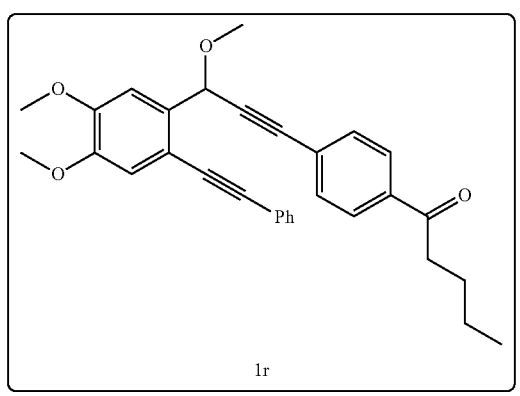 [SMILES: CCCCC(=O)c1ccc(C#CC(OC)c2cc(OC)c(OC)cc2C#Cc2ccccc2)cc1]

Pale yellow liquid; IR (neat, cm-1): 3065, 3010, 2840, 2190, 1560, 1380, 1140, 1020, 740; ¹H-NMR (400 MHz, CDCl₃): δ 7.88 (dd, J=1.6, 5.1 Hz, 2H), 7.56-7.51 (m, 4H), 7.36-7.34 (m, 3H), 7.26 (s, 1H), 7.04 (s, 1H), 5.76 (s, 1H), 3.94 (s, 3H), 3.91 (s, 3H), 3.56 (s, 3H), 2.92 (t, J=7.3 Hz, 2H), 1.73-1.65 (m, 2H), 1.43-1.34 (m, 2H), 0.93 (t, J=7.3 Hz, 3H); ¹³C-NMR (150 MHz, CDCl₃): δ 199.6, 149.8, 148.7, 136.3, 133.3, 131.8 (2×CH), 131.3 (2×CH), 128.4 (2×CH), 128.3, 127.8 (2×CH), 127.0, 123.1, 114.4, 114.0, 109.8, 93.0, 90.2, 86.7, 86.1, 71.3, 56.9, 56.0, 55.9, 38.2, 26.3, 22.3, 13.8; HRMS calcd for C₃₁H₃₀O₄: 466.2144. found: 466.2124.

3-phenyl-1-(2-(phenylethynyl)phenyl)prop-2-yn-1-ol (1s)

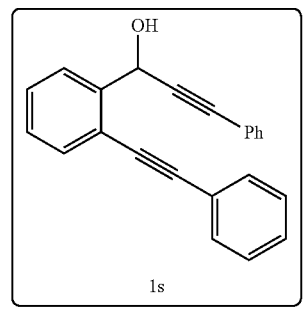 [SMILES: OC(C#Cc1ccccc1)c1ccccc1C#Cc1ccccc1]

Pale yellow thick syrup; IR (neat, cm-1): 3350, 3090, 3020, 2850, 2150, 1580, 1240, 1075, 700; ¹H-NMR (600 MHz, CDCl₃): δ 7.81 (d, J=7.7 Hz, 1H), 7.61-7.59 (m, 3H), 7.48-7.47 (m, 2H), 7.42 (t, J=7.5 Hz, 1H), 7.38-7.27 (m, 6H), 7.21-7.19 (m, 1H), 6.19 (s, 1H), 2.91 (s, 1H); ¹³C-NMR (100 MHz, CDCl₃): δ 142.2, 132.4, 131.7 (2×CH), 131.5 (2×CH), 128.9, 128.8, 128.6, 128.4, 128.39, 128.2, 128.1, 126.7, 125.2, 122.7, 122.4, 121.4, 95.0, 88.2, 86.6, 86.5, 63.7; HRMS calcd for C₂₃H₁₆O: 308.1201. found: 308.1203.

1-(phenylethynyl)-2-(3-phenylprop-2-yn-1-yl)benzene (1t)

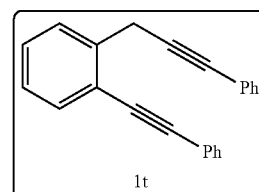

Pale brown liquid; IR (neat, cm-1): 3050, 2150, 1610, 1540, 1180, 750; ¹H-NMR (400 MHz, CDCl₃): δ 7.73-7.71 (m, 1H), 7.60-7.56 (m, 3H), 7.51-7.49 (m, 2H), 7.41-7.36 (m, 4H), 7.34-7.27 (m, 4H), 4.12 (s, 2H); ¹³C-NMR (100 MHz, CDCl₃): δ 138.5, 131.8, 131.6 (2×CH), 131.5 (2×CH), 128.6 (2×CH), 128.4 (2×CH), 128.2 (2×CH), 128.0, 127.8, 126.6, 123.6, 123.1, 122.3, 94.5, 87.2, 87.0, 83.1, 24.7; HRMS calcd for C₂₃H₁₆: 292.1252. found: 292.1246.

Synthetic Scheme for the Preparation of (3-methoxyprop-1-yne-1,3-diyl)dibenzene (3)

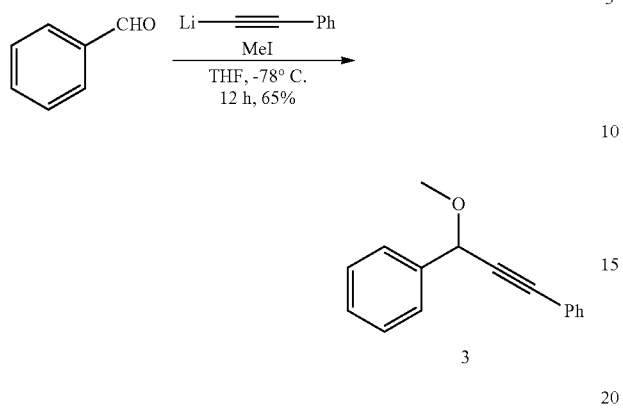

a) Synthesis of (3-methoxyprop-1-yne-1,3-diyl)dibenzene (3)

A THF solution of ethynylbenzene (1.0 g, 10.30 mmol) was cooled to −78° C. n-BuLi (2.5 M in hexane, 4.30 mL, 10.78 mmol) was slowly added to this solution and was stirred for 0.5 h at −78° C. Benzaldehyde (1.00 g, 9.42 mmol) was added to the resulting solution and was stirred for 1 h at −78° C. Iodomethane (1.60 g, 11.30 mmol) was added to the solution and was stirred for 12 h at room temperature. The reaction was quenched with water (15 mL) and extracted with ethyl acetate (100 mL). The extract was washed with brine solution, dried over $MgSO_4$, and concentrated under reduced pressure. The residue was eluted through a silica column to afford (3-methoxyprop-1-yne-1,3-diyl)dibenzene (3) (1.36 g, 6.11 mmol, 65%) as pale yellow liquid.

IR (neat, cm-1): 3090, 3010, 2850, 2150, 1580, 1240, 1075; $^1$H-NMR (400 MHz, $CDCl_3$): δ 7.50-7.49 (m, 2H), 7.42-7.40 (m, 2H), 7.37-7.36 (m, 2H), 7.34-7.32 (m, 4H), 5.33 (s, 1H), 3.51 (s, 3H); $^{13}$C-NMR (100 MHz, $CDCl_3$): δ 138.5, 131.8 (2×CH), 128.5 (2×CH), 128.4 (2×CH), 128.2 (2×CH), 127.5 (2×CH), 122.5, 87.7, 86.6, 73.5, 55.9.

1,2-diphenylethyne (4)

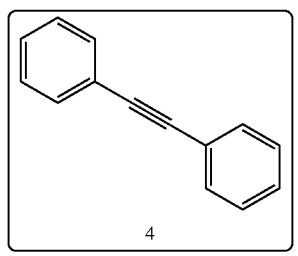 [SMILES: C(#Cc1ccccc1)c1ccccc1]

$^1$H-NMR (400 MHz, $CDCl_3$): δ 7.60-7.58 (m, 2H), 7.39-7.26 (m, 3H), $^{13}$C-NMR (100 MHz, $CDCl_3$): δ 131.6 (4×CH), 128.3 (4×CH), 128.2 (4×CH), 123.2 (2×CH), 89.4 (2×CH).

2,2'-(3-methoxyprop-1-yne-1,3-diyl)bis((phenylethynyl)benzene) (1u)

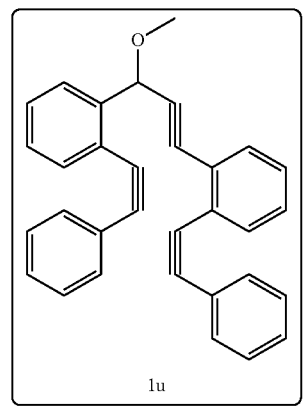 [SMILES: COC(C#Cc1ccccc1C#Cc1ccccc1)c1ccccc1C#Cc1ccccc1]

Synthetic Scheme A6, 70% yield. Brown syrup; IR (neat, cm-1): 3060, 3020, 2240, 2150, 1510, 1460, 1240, 1100, 750, 700; $^1$H-NMR (400 MHz, $CDCl_3$): δ 7.95 (d, J=7.7 Hz, 1H), 7.58-7.53 (m, 5H), 7.49-7.47 (m, 2H), 7.39-7.20 (m, 10H), 5.93 (s, 1H), 3.63 (s, 3H); $^{13}$C-NMR (100 MHz, $CDCl_3$): δ 139.9, 132.2, 132.1, 131.8, 131.7 (3×CH), 131.5 (3×CH), 128.8, 128.4, 128.3 (3×CH), 128.2 (3×CH), 127.8 (2×CH), 126.0, 125.0, 123.0, 122.5, 94.0, 93.4, 90.6, 88.0, 86.8, 86.1, 71.7, 56.9; HRMS calcd for $C_{32}H_{22}O$: 422.1671. found: 422.1693.

3-(2-(phenylethynyl)phenyl)-1-(2-((2-(phenylethynyl)phenyl)ethynyl)phenyl)prop-2-yn-1-ol (1v)

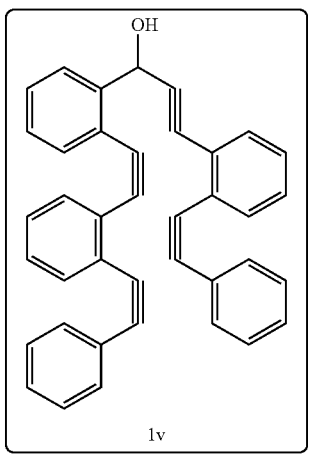 [SMILES: OC(C#Cc1ccccc1C#Cc1ccccc1)c1ccccc1C#Cc1ccccc1C#Cc1ccccc1]

Synthetic Scheme A6, 78% yield. Brown syrup; IR (neat, cm-1): 3350, 3020, 2240, 2150, 1510, 1460, 1248, 1210, 1100, 750, 700; $^1$H-NMR (400 MHz, $CDCl_3$): δ 7.95 (d, J=7.7 Hz, 1H), 7.58-7.53 (m, 5H), 7.49-7.47 (m, 1H), 7.46-7.44 (m, 3H), 7.39-7.20 (m, 11H), 7.19-7.16 (m, 1H), 6.42 (d, J=3.7 Hz, 1H), 2.72 (d, J=3.7 Hz, 1H); $^{13}$C-NMR (100 MHz, $CDCl_3$): δ 140, 132.2, 132.1 (2×CH), 131.7 (3×CH), 131.6 (3×CH), 128.9, 128.4 (2×CH), 128.3 (3×CH), 128.2 (2×CH), 128.1, 128.0, 127.9 (2×CH), 127.8, 125.9, 125.5, 125.4, 125.0, 123.0, 122.9, 122.6, 93.6, 93.4, 92.8, 90.9, 90.8, 88.2, 88.0, 86.1, 65.5; HRMS calcd for C$_{39}$H$_{24}$O: 508.1827. found: 508.1831.

1-(4-fluoro-2-((2-(phenylethynyl)phenyl)ethynyl)phenyl)-3-(2-(phenylethynyl)phenyl)prop-2-yn-1-ol (1w)

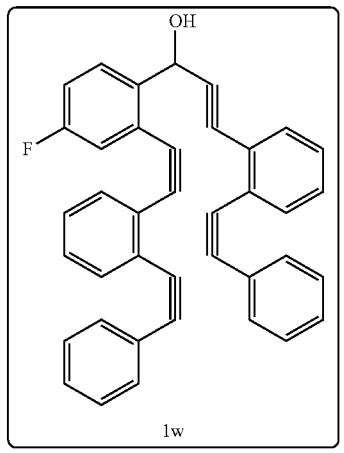 [SMILES: OC(C#Cc1ccccc1C#Cc1ccccc1)c1ccc(F)cc1C#Cc1ccccc1C#Cc1ccccc1]

Synthetic Scheme A6, 74% yield. Brown syrup; IR (neat, cm-1): 3340, 3061, 2927, 2821, 2217, 1606, 1580, 1490, 1444, 1185, 1078, 750, 700; $^1$H-NMR (400 MHz, CDCl$_3$): δ 7.97 (dd, J=5.72, 2.92 Hz, 1H), 7.69-7.66 (m, 2H), 7.62 (d, J=1.64 Hz, 2H), 7.61-7.60 (m, 1H), 7.57-7.54 (m, 3H), 7.48-7.25 (m, 11H), 6.83-6.78 (m, 1H), 6.42 (d, J=3.4 Hz, 1H), 2.3 (d, J=3.4 Hz, 1H); $^{13}$C-NMR (100 MHz, CDCl$_3$): δ 162 (J$_{cf}$=246 Hz,), 138.2, 132.1 (2×CH), 132.0, 131.7 (3×CH), 131.6 (3×CH), 129.4, 129.3, 128.6, 128.6, 128.4 (2×CH), 128.2 (3×CH), 128.0 (3×CH), 127.8 (2×CH), 125.8, 125.6, 124.6, 123.4, (J$_{cf}$=9.8 Hz), 122.7 (J$_{cf}$=20.6 Hz), 118.7 (J$_{cf}$=23 Hz), 116.2 (J$_{cf}$=21.2 Hz,), 94.1, 93.6, 93.4, 92.1, 79.9, 85.2, 62.8; HRMS calcd for C$_{39}$H$_{23}$FO: 526.1733. found: 526.1731.

1-(4,5-dimethoxy-2-((2-(phenylethynyl)phenyl)ethynyl)phenyl)-3-(2-(phenylethynyl)phenyl)prop-2-yn-1-ol (1x)

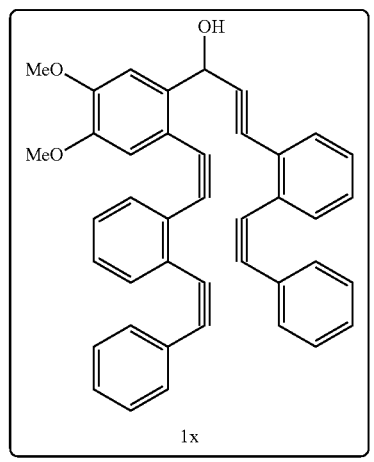 [SMILES: COc1cc(C#Cc2ccccc2C#Cc2ccccc2)c(C(O)C#Cc2ccccc2C#Cc2ccccc2)cc1OC]

Synthetic Scheme A6, 64% yield. Brown syrup; IR (neat, cm-1): 3350, 3065, 2933, 2852, 2208, 1513, 1248, 1210, 1100, 750, 700; $^1$H-NMR (400 MHz, CDCl$_3$): δ 7.68-7.64 (m, 2H), 7.59-7.56 (m, 2H), 7.53-7.51 (m, 1H), 7.45-7.43 (m, 1H), 7.40-7.38 (m, 3H), 7.29-7.21 (m, 10H), 7.02 (s, 1H), 6.4 (s, 1H), 3.76 (s, 3H), 3.76 (s, 3H), 2.81 (s, 1H); $^{13}$C-NMR (100 MHz, CDCl$_3$): δ 149.8, 148.5, 135.7, 131.9, 131.8 (2×CH), 131.6 (2×CH), 131.6 (2×CH), 128.9, 128.4 (2×CH), 128.3 (2×CH), 128.2, 128.1, 128.0, 127.9 (2×CH), 127.8, 125.8, 125.5, 125.3, 125.0, 122.9, 122.8, 114.2, 113.4, 110.0, 93.5, 93.3, 92.8, 91.9, 90.9, 88.2, 88.0, 84.9, 63.2, 55.7, 55.6; HRMS calcd for C$_{41}$H$_{28}$O$_3$: 568.2038. found: 568.2040.

11-phenyl-11H-benzo[a]fluorene (2a)

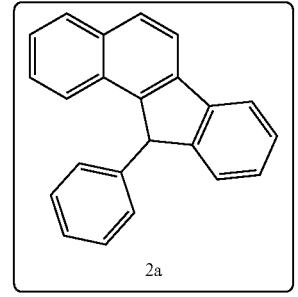 [SMILES: c1ccc(C2c3ccccc3-c3ccc4ccccc4c32)cc1]

White solid (m.p.: 198-201° C.); IR (neat, cm-1): 3064, 3010, 2870, 1540, 1060, 950; $^1$H-NMR (600 MHz, CDCl$_3$): δ 7.99-7.94 (m, 2H), 7.91 (d, J=8.1 Hz, 1H), 7.85 (d, J=7.5 Hz, 1H), 7.67 (d, J=8.2 Hz, 1H), 7.41-7.37 (m, 2H), 7.35-7.31 (m, 2H), 7.27-7.21 (m, 4H), 7.13-7.12 (m, 2H), 5.35 (s, 1H); $^{13}$C-NMR (150 MHz, CDCl$_3$): δ 149.1, 142.6, 141.6, 140.9, 139.3, 133.5, 130.4, 129.0, 128.9 (2×C), 128.8, 128.0 (2×CH), 127.1, 126.9, 126.7, 126.3, 125.1, 124.9, 124.6, 119.6, 118.5, 54.0; HRMS calcd for C$_{23}$H$_{16}$: 292.1252. found: 292.1247.

Tributyl(11-phenyl-11H-benzo[a]fluoren-6-yl)stannane (2a-Sn)

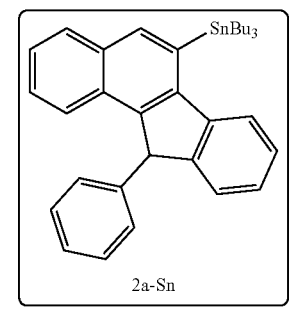

Compound 2a-Sn was eluted through a silica column using n-Hexanes as eluent (traces amount of Sn cleaved product 2a is observed). Pale yellow solid; IR (neat, cm-1): 3064, 3010, 2870, 1540, 1400, 1260, 1140, 780, 540; $^1$H-NMR (400 MHz, CDCl$_3$): δ 7.97 (s, 1H), 7.94-7.85 (m, 2H), 7.70 (d, J=8.24 Hz, 1H), 7.42-7.37 (m, 3H), 7.36-7.28 (m, 4H), 7.27-7.13 (m, 2H), 5.37 (s, 1H), 1.71-1.65 (m, 6H), 1.46-1.35 (m, 12H), 0.98-0.91 (m, 9H); $^{13}$C-NMR (100 MHz, CDCl$_3$): δ 149.5, 144.9, 142.9, 142.4, 142.2, 138.2, 132.5, 130.2, 129.0, 128.9, 128.8, 128.0, 127.1, 126.9, 126.7, 126.3, 125.1, 124.9, 124.6, 120.3, 119.6, 118.5, 53.7, 29.1 (3×CH2), 27.3 (3×CH2), 13.7 (3×CH2), 10.9 (3×CH3); HRMS calcd for C$_{35}$H$_{42}$Sn: 582.2308. found: 582.2309.

3-methoxy-11-phenyl-11H-benzo[a]fluorene (2b)

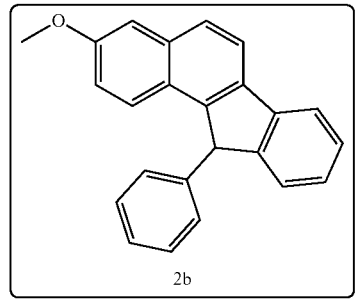 [SMILES: COc1ccc2c3c(ccc2c1)-c1ccccc1C3c1ccccc1]

White solid (m.p.: 163-166° C.); IR (neat, cm-1): 3055, 2926, 2836, 1594, 1235, 1026, 750; $^1$H-NMR (400 MHz, CDCl$_3$): δ 7.93 (d, J=8.4 Hz, 1H), 7.83 (d, J=8.4 Hz, 1H), 7.8 (d, J=7.6 Hz, 1H), 7.56 (d, J=9.1 Hz, 1H), 7.35 (t, J=7.4 Hz, 1H), 7.31 (d, J=7.2 Hz, 1H), 7.24-7.18 (m, 5H), 7.12-7.10 (m, 2H), 6.98 (d, 9.1 Hz, 1H), 5.31 (s, 1H), 3.90 (s, 3H); $^{13}$C-NMR (150 MHz, CDCl$_3$): δ 157.1, 148.7, 142.9, 141.8, 141.1, 137.3, 134.7, 128.8 (2×CH), 128.0 (2×CH), 127.6, 127.1, 126.7, 126.5, 126.0, 125.8, 124.8, 119.2, 119.0 (2×CH), 107.1, 55.2, 54.0; HRMS calcd for C$_{24}$H$_{18}$O: 322.1352. found: [M+H]$^+$=323.1430.

2,3-dimethoxy-11-phenyl-11H-benzo[a]fluorene (2c)

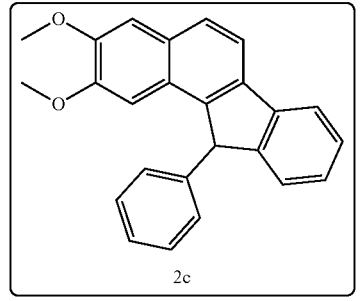 [SMILES: COc1cc2ccc3c(c2cc1OC)C(c1ccccc1)c1ccccc1-3]

White solid (m.p.: 148-151° C.); IR (neat, cm-1): 3026, 2930, 2840, 1491, 1251, 1222, 1032, 755; $^1$H-NMR (400 MHz, CDCl$_3$): δ 7.84-7.76 (m, 3H), 7.37 (t, J=7.5 Hz, 1H), 7.25-7.20 (m, 5H), 7.18 (s, 1H), 7.14-7.12 (m, 2H), 6.90 (s, 1H), 5.25 (s, 1H), 3.97 (s, 3H), 3.64 (s, 3H); $^{13}$C-NMR (100 MHz, CDCl$_3$): δ 149.4, 148.9, 148.7, 141.7, 141.4, 137.6, 129.2 (2×CH), 128.8 (2×CH), 128.2 (2×CH), 127.1, 126.9, 126.7, 126.5, 126.0, 124.8, 119.3, 116.7, 107.3, 103.3, 55.7, 55.4, 54.1; HRMS calcd for C$_{25}$H$_{20}$O$_2$: 352.1458. found: [M+H]$^+$=353.1539.

11-phenyl-11H-indeno[2',1':5,6]naphtho[2,3-d][1,3]dioxole (2d):

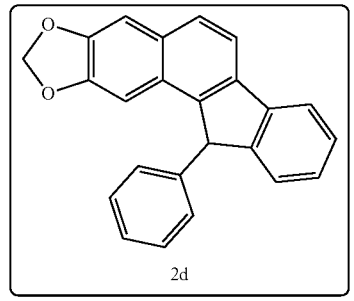 [SMILES: c1ccc(C2c3ccccc3-c3ccc4cc5c(cc4c32)OCO5)cc1]

Pale yellow solid (m.p.: 172-175° C.); IR (neat, cm-1): 3100, 3020, 2850, 1540, 1460, 1210, 1060, 800; $^1$H-NMR (600 MHz, CDCl$_3$): δ 7.81 (d, J=8.2 Hz, 1H), 7.79 (d, J=7.5 Hz, 1H), 7.55 (d, J=8.3 Hz, 1H), 7.35 (t, J=7.3 Hz, 1H), 7.29-7.18 (m, 6H), 7.10 (d, J=7.0 Hz, 2H), 6.94 (s, 1H), 5.95 (dd, J=1.3 Hz, 23.4 Hz, 2H), 5.23 (s, 1H); $^{13}$C-NMR (100 MHz, CDCl$_3$): δ 148.7, 147.7, 147.0, 142.0, 141.6, 141.0, 138.0, 130.5, 128.9 (2×C), 128.4 (2×CH), 127.9, 127.7, 127.4, 126.8, 126.7, 124.8, 119.4, 116.9, 105.0, 100.1, 100.9, 54.1; HRMS calcd for C$_{24}$H$_{16}$O$_2$: 336.1150. found: 336.1147.

9-methoxy-11-phenyl-11H-benzo[a]fluorene (2e)

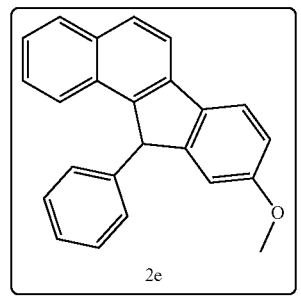 [SMILES: COc1ccc2c(c1)C(c1ccccc1)c1c-2ccc2ccccc12]

Pale orange solid (m.p.: 162-163° C.); IR (neat, cm-1): 3057, 2925, 2852, 1600, 1581, 1483, 1454, 1286; $^1$H-NMR (400 MHz, CDCl$_3$): δ 7.94-7.88 (m, 2H), 7.87 (d, J=7.1 Hz, 1H), 7.72 (d, J=8.2 Hz, 1H), 7.62 (d, J=8.2 Hz, 1H), 7.35 (t, J=7.4 Hz, 1H), 7.32-7.20 (m, 4H), 7.12 (d, J=7.2 Hz, 2H), 6.92 (d, J=8.4 Hz, 1H), 6.88 (s, 1H), 5.30 (s, 1H), 3.79 (s, 3H); $^{13}$C-NMR (150 MHz, CDCl$_3$): δ 159.5, 151.0, 141.8, 141.7, 139.3, 134.0, 132.9, 130.4, 128.93 (2×CH), 128.91, 128.8 (2×CH), 128.0, 126.8, 126.3, 124.7, 124.3, 120.3, 118.2, 112.9, 111.0, 55.5, 54.1; HRMS calcd for C$_{24}$H$_{18}$O: 322.1358. found: 322.1350.

11-phenyl-11H-naphtho[a]fluorene (2f)

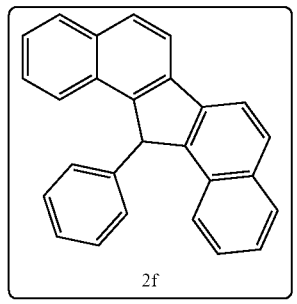 [SMILES: c1ccc(C2c3c(ccc4ccccc34)-c3ccc4ccccc4c32)cc1]

Pale brown solid (m.p.: 191-193° C.); IR (neat, cm-1): 3070, 2900, 2850, 1560, 1340, 1090, 920, 800; $^1$H-NMR (400 MHz, CDCl$_3$): δ 8.03 (d, J=8.4 Hz, 2H) 7.95-7.92 (m, 4H), 7.88-7.86 (m, 2H), 7.36-7.33 (m, 4H), 7.24-7.19 (m, 4H), 7.15-7.13 (m, 1H), 5.72 (s, 1H); $^{13}$C-NMR (100 MHz, CDCl$_3$): δ 144.7 (2×C), 139.2 (2×C), 133.3 (2×C), 130.2 (2×C), 129.05 (2×C), 128.93 (2×C), 128.91 (2×C), 128.8 (2×CH), 128.7 (2×C), 126.6, 126.4 (2×C), 125.0 (2×C), 123.8 (2×C), 118.4, 54.1; HRMS calcd for C$_{27}$H$_{18}$: 342.1409. found: 342.1397.

1-(4-(trifluoromethyl)phenyl)-11H-benzo[a]fluorene (2g)

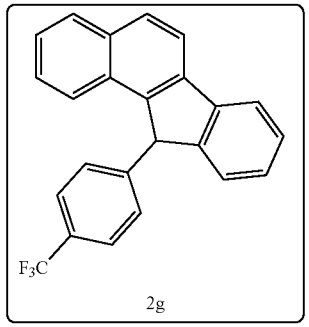 [SMILES: FC(F)(F)c1ccc(C2c3ccccc3-c3ccc4ccccc4c32)cc1]

White solid (m.p.: 193-195° C.); IR (neat, cm-1): 3075, 2850, 1600, 1340, 1140, 1100, 750; $^1$H-NMR (600 MHz, CDCl$_3$): δ 7.99-7.96 (m, 2H), 7.92 (d, J=8.1 Hz, 1H), 7.85 (d, J=7.6 Hz, 1H), 7.57 (d, J=8.3 Hz, 1H), 7.51 (d, J=8.1 Hz, 2H), 7.42-7.39 (m, 2H), 7.36-7.34 (m, 1H), 7.33-7.329 (m, 1H), 7.27-7.22 (m, 3H), 5.39 (s, 1H); $^{13}$C-NMR (150 MHz, CDCl$_3$): δ 148.2, 146.0, 141.8, 141.0, 139.5, 133.5, 130.1, 129.2, 129.1, 128.3 (2×CH), 127.5, 127.1, 126.6, 125.93 (t, J=3.9 Hz), 129.0, 125.9, 125.4, 124.8, 124.2, 119.9, 118.5, 53.6 (one carbon peak merge with other peaks); HRMS calcd for C$_{24}$H$_{15}$F$_3$: 360.1126. found: 360.1142.

11-(4-methoxyphenyl)-11H-benzo[a]fluorene (2h)

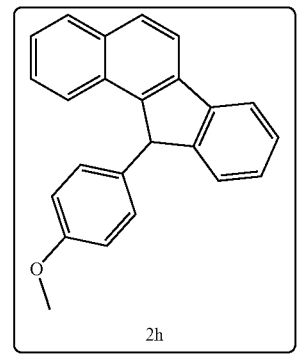 [SMILES: COc1ccc(C2c3ccccc3-c3ccc4ccccc4c32)cc1]

White solid (m.p.: 184-187° C.); IR (neat, cm-1): 3055, 2936, 2840, 1507, 1247, 1029, 753; $^1$H-NMR (400 MHz, CDCl$_3$): δ 7.98-7.92 (m, 2H), 7.89 (d, J=7.9 Hz, 1H), 7.82 (d, J=7.5 Hz, 1H), 7.69 (d, J=8.1 Hz, 1H), 7.40-7.30 (m, 4H), 7.23-7.21 (m, 1H), 7.03 (d, J=8.6 Hz, 2H), 6.78 (d, J=8.72 Hz, 2H), 5.31 (s, 1H), 3.75 (s, 3H); $^{13}$C-NMR (150 MHz, CDCl$_3$): δ 158.3, 149.4, 142.8, 140.8, 139.1, 133.5 (2×CH), 130.4, 128.9 (3×CH), 128.7, 127.0, 126.9, 126.3, 125.1, 124.8, 124.6, 119.5, 118.5, 114.2 (2×CH), 55.1, 53.2; HRMS calcd for C$_{24}$H$_{18}$O: 322.1352. found: [M+NH$_4$]$^+$=340.1696.

11-butyl-11H-benzo[a]fluorene (2i)

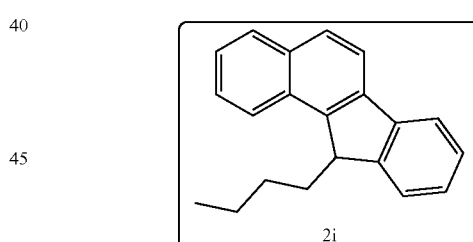

Pale yellow liquid; IR (neat, cm-1): 3052, 2923, 2854, 1607, 1583, 1523, 1467; $^1$H-NMR (400 MHz, CDCl$_3$): δ 8.11 (d, J=8.7 Hz, 1H), 7.94 (d, J=8.7 Hz, 1H), 7.91 (d, J=8.6 Hz, 1H), 7.87 (d, J=8.6 Hz, 1H), 7.81 (d, J=7.9 Hz, 1H), 7.61 (d, J=7.6 Hz, 1H), 7.56 (t, J=7.6 Hz, 1H), 7.47 (t, J=7.5 Hz, 1H), 7.41 (t, J=7.1 Hz, 1H), 7.33 (t, J=7.4 Hz, 1H), 4.45-4.41 (m, 1H), 2.43-2.33 (m, 1H), 2.24-2.12 (m, 1H), 1.25-1.06 (m, 2H), 0.94-0.83 (m, 2H), 0.71 (t, J=7.3 Hz, 3H); $^{13}$C-NMR (150 MHz, CDCl$_3$): δ 148.5, 143.0, 141.8, 138.5, 133.3, 130.4, 129.2, 128.0, 126.8, 126.3, 126.2, 125.0, 124.0 (2×CH), 119.5, 118.6, 47.1, 33.2, 26.8, 22.9, 13.8; HRMS calcd for C$_{21}$H$_{20}$: 272.1565. found: 272.1565.

3-fluoro-11-phenyl-11H-benzo[a]fluorene (2j)

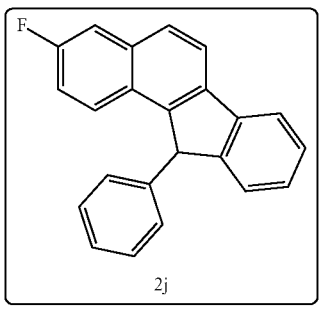 [SMILES: Fc1ccc2c3c(ccc2c1)-c1ccccc1C3c1ccccc1]

White solid (m.p.: 151-153° C.); IR (neat, cm-1): 3100, 3020, 2840, 1520, 1400, 1260, 1110, 780; ¹H-NMR (400 MHz, CDCl₃): δ 8.77 (dd, J=1.7, 2.5 Hz, 1H), 8.17 (dd, J=1.7, 6.4 Hz, 1H), 8.04 (d, J=8.3 Hz, 1H), 7.91 (d, J=8.2 Hz, 1H), 7.87 (d, J=7.5 Hz, 1H), 7.43-7.41 (m, 2H), 7.40-7.27 (m, 2H), 7.21-7.19 (m, 2H), 7.16-7.13 (m, 3H), 5.65 (s, 1H); ¹³C-NMR (150 MHz, CDCl₃): δ 150.5, 149.8, 145.4, 143.9, 142.8, 141.8, 140.5 136.4, 128.8, 128.4 (2×CH), 128.3, 128.2 (2×CH), 128.0, 127.7, 127.1, 126.2, 125.3, 120.3, 120.0, 119.2, 53.6; HRMS calcd for $C_{23}H_{15}F$: 310.1158. found: 310.1167.

2-fluoro-11-phenyl-11H-benzo[a]fluorene (2k)

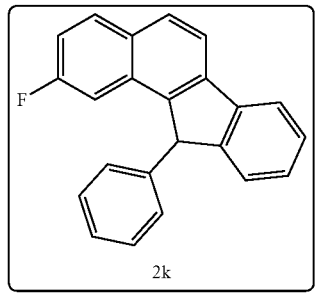 [SMILES: Fc1ccc2ccc3c(c2c1)C(c1ccccc1)c1ccccc1-3]

White solid (m.p.: 160-162° C.); IR (neat, cm-1): 3059, 2922, 2851, 1630, 1592, 1493, 1474, 1072; ¹H-NMR (400 MHz, CDCl₃): δ 7.92 (s, 2H), 7.88 (dd, J=9.0, 5.8 Hz, 1H), 7.84 (d, J=7.6, 1 H), 7.39 (t, J=7.1 Hz, 1H), 7.33 (d, J=7.5 Hz, 1H), 7.29-7.21 (m, 5H), 7.15 (t, 8.7 Hz, 1H), 7.12-7.08 (m, 2H), 5.29 (s, 1H); ¹³C-NMR (150 MHz, CDCl₃): δ 149.2, 141.0, 140.5 (d, $J_{CF}$=51.7 Hz), 131.4, 131.3, 131.3, 130.5 (3×CH), 129.0, 128.8 (2×CH), 128.0, 127.3, 127.3, 127.0, 125.0, 119.9, 117.8, 115.5, 115.4, 108.0 (d, $J_{CF}$=21.7 Hz), 54.1; HRMS calcd for $C_{23}H_{15}F$: 310.1158. found: $[M+NH_4]^+$=328.1496.

11-phenyl-11H-indeno[1,2-h]quinoline (2l)

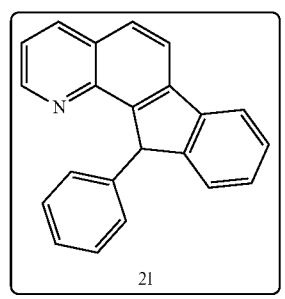 [SMILES: c1ccc(C2c3ccccc3-c3ccc4cccnc4c32)cc1]

Pale yellow solid (m.p.: 150-152° C.); IR (neat, cm-1): 3054, 2810, 1600, 1530, 1020, 850, 780; ¹H-NMR (600 MHz, CDCl₃): δ 7.99 (d, J=8.4 Hz, 1H), 7.88 (d, J=8.5 Hz, 1H), 7.82 (d, J=7.5 Hz, 1H), 7.65 (dd, J=5.6, 3.5 Hz, 1H), 7.51 (dd, J=2.4, 7.4 Hz, 1H), 7.38 (t, J=7.4 Hz, 1H), 7.32 (d, J=7.4 Hz, 1H), 7.27-7.22 (m, 4H), 7.10-7.08 (m, 3H), 5.32 (s, 1H); ¹³C-NMR (100 MHz, CDCl₃): δ 161.0, 159.4, 148.8, 142.9, 141.4, 140.7, 138.7, 134.3, 128.9 (2×C), 128.1, 128.0 (2×CH), 127.4, 127.2, 126.9, 126.8, 124.9, 119.6, 116.7, 112.1, 54.1; HRMS calcd for $C_{22}H_{15}N$: 293.1204. found $[M+H]^+$: 294.1290.

3-chloro-11-phenyl-11H-benzo[a]fluorene (2m)

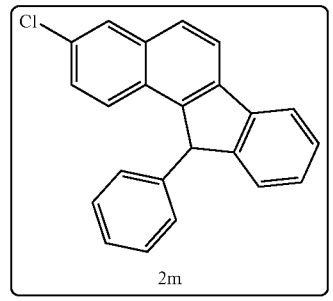 [SMILES: Clc1ccc2c3c(ccc2c1)-c1ccccc1C3c1ccccc1]

White solid (m.p.: 187-190° C.); IR (neat, cm-1): 3052, 3023, 2926, 1453, 1074, 745; ¹H-NMR (400 MHz, CDCl₃): δ 7.99 (d, J=8.4 Hz, 1H), 7.87-7.82 (m, 3H), 7.59 (d, J=8.9 Hz, 1H), 7.38 (t, J=7.5 Hz, 1H), 7.33 (d, J=7.5 Hz, 1H), 7.26-7.21 (m, 5H), 7.10-7.08 (m, 2H), 5.32 (s, 1H); ¹³C-NMR (150 MHz, CDCl₃): δ 149.0, 142.7, 141.3, 140.5, 139.6, 134.1, 130.9, 128.9 (2×CH), 128.6, 128.0, 127.9 (2×CH), 127.6, 127.3, 127.2 (2×CH), 126.9, 126.1, 124.9, 119.7, 119.6, 54.0; HRMS calcd for $C_{23}H_{15}Cl$: 326.0682. found: $[M]^+$=326.0854.

11-phenyl-9-(trifluoromethyl)-11H-benzo[a]fluorene (2n)

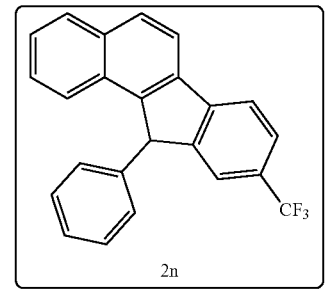 [SMILES: FC(F)(F)c1ccc2c(c1)C(c1ccccc1)c1c-2ccc2ccccc12]

Pale yellow solid (m.p.: 175-179° C.); IR (neat, cm-1): 3060, 2921, 2851, 1617, 1599, 1492, 1445, 1168, 1123, 1084; ¹H-NMR (400 MHz, CDCl₃): δ 8.00 (s, 2H), 7.92 (dd, J=8.1, 4.0 Hz, 2H), 7.66 (t, J=7.5 Hz, 2H), 7.55 (s, 1H), 7.43 (t, J=7.5 Hz, 1H), 7.35 (t, J=7.5 Hz, 1H), 7.30-7.24 (m, 3H), 7.11 (d, J=7.2 Hz, 2H), 5.39 (s, 1H); ¹³C-NMR (100 MHz, CDCl₃): δ149.3, 144.5, 143.9, 140.4, 137.8, 134.0, 130.2, 129.3 (2×CH), 129.1 (2×CH), 129.0, 128.0 (2×CH), 127.2, 126.7, 125.9, 124.8, 124.68, 124.66, 121.8 (2×C), 119.7, 118.6, 54.1; HRMS calcd for $C_{24}H_{15}F_3$: 360.1126. found: 360.1124.

11-phenyl-11H-benzo[a]fluorene-9-carbonitrile (2o)

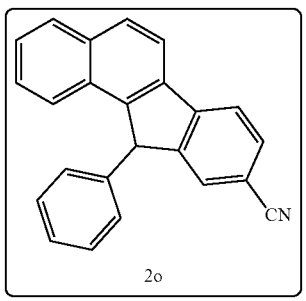 [SMILES: N#Cc1ccc2c(c1)C(c1ccccc1)c1c-2ccc2ccccc12]

White solid (m.p.: 183-185° C.); IR (neat, cm-1): 3059, 2925, 2853, 2225, 1607, 1492, 1472, 1451; $^1$H-NMR (400 MHz, CDCl$_3$): δ 7.98 (q, J=8.5, 8.0 Hz, 2H), 7.93 (d, J=8.1 Hz, 1H), 7.88 (d, J=7.8 Hz, 1H), 7.66 (t, J=8.6 Hz, 2H), 7.57 (s, 1H), 7.46 (t, J=7.1 Hz 1H), 7.36 (t, J=7.4 Hz 1H), 7.29-7.26 (m, 3H), 7.08 (d, J=6.4 Hz 2H), 5.36 (s, 1H); $^{13}$C-NMR (100 MHz, CDCl$_3$): δ 149.4, 145.5, 144.2, 139.8, 137.5, 134.2, 131.7, 130.0 (2×C), 129.5 (2×CH), 129.2, 129.0, 128.5 (2×CH), 127.8, 127.4, 126.9, 126.3, 124.8, 120.1, 118.5, 109.7, 53.9; HRMS calcd for C$_{24}$H$_{15}$N: 317.1204. found: 317.1196.

Tributyl(9-fluoro-11-phenyl-11H-benzo[a]fluoren-6-yl)stannane (2p-Sn)

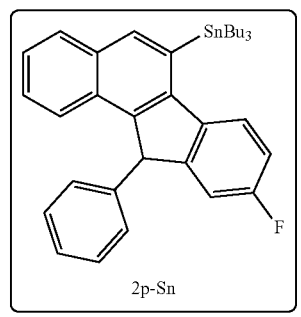

White solid (m.p.: 108-110° C.); IR (neat, cm-1): 3100, 3020, 2840, 1520, 1400, 1260, 1110, 780, 540; $^1$H-NMR (400 MHz, CDCl$_3$): δ 8.15 (s, 1H), 7.94 (d, J=8.1 Hz, 1H), 7.91-7.88 (m, 1H), 7.71 (d, J=8.3 Hz, 1H), 7.47-7.44 (m, 1H), 7.37-7.28 (m, 4H), 7.20-7.11 (m, 4H), 5.35 (s, 1H), 1.78-1.70 (m, 6H), 1.53-1.41 (m, 12H), 1.00 (t, J=7.3 Hz, 9H); $^{13}$C-NMR (100 MHz, CDCl$_3$): δ 163.4, 160.9, 151.7 (d, J=7.8 Hz), 144.1, 142.1 (d, J=2.6 Hz), 141.5, 138.8 (d, J=2.5 Hz), 138.4, 132.4, 132.2 (d, J=30.3 Hz), 129.0 (2×CH), 128.4, 127.9 (2×CH), 126.9, 126.4, 125.2, 124.4, 121.1 (d, J=8.3 Hz), 113.6 (d, J=22.5 Hz), 112.4 (d, J=22.7 Hz), 53.7, 29.1 (3×CH2), 27.3 (3×CH2), 13.7 (3×CH2), 10.8 (3×CH2); HRMS calcd for C$_{35}$H$_{41}$FSn: 600.2214. found: 600.2246.

9-fluoro-11-phenyl-11H-benzo[a]fluorene (2p)

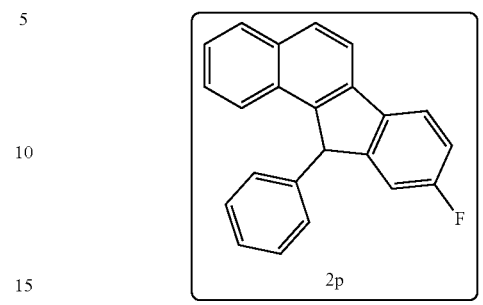

White solid (m.p.: 170-173° C.); IR (neat, cm-1): 3059, 2922, 2851, 1630, 1592, 1493, 1474, 1072; $^1$H-NMR (400 MHz, CDCl$_3$): δ 7.96-7.90 (m, 3H), 7.55 (dd, J=5.0, 3.3 Hz, 1H), 7.63 (d, J=8.3, 1 H), 7.42-7.38 (m, 1H), 7.34-7.23 (m, 4H), 7.12-7.02 (m, 4H), 5.29 (s, 1H); $^{13}$C-NMR (100 MHz, CDCl$_3$): δ 162.5 (d, J$_{CF}$=243.6 Hz), 151.2 (d, J$_{CF}$=8.1 Hz), 142.3, 141.0 138.5, 136.9, 133.2, 130.3, 129.0 (3×CH), 128.9 (2×CH), 127.9, 127.0, 126.5, 124.4, 120.4 (d, J$_{CF}$=8.8 Hz), 118.2, 114.2 (d, J$_{CF}$=22.9 Hz), 112.4 (d, J$_{CF}$=22.9 Hz), 54.0 (d, J$_{CF}$=2.2 Hz); HRMS calcd for C$_{23}$H$_{15}$F: 310.1158. found: [M+NH$_4$]$^+$=328.1492.

2,3-dimethoxy-11-phenyl-11H-benzo[a]fluorene-9-carbonitrile (2q)

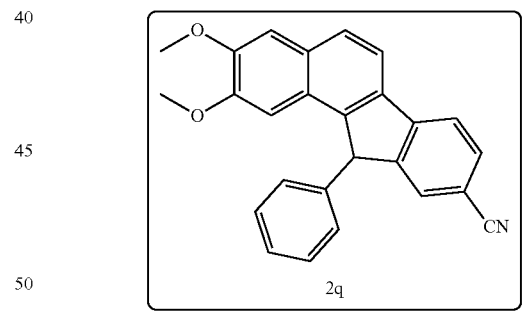

Pale yellow solid (m.p.: 178-182° C.); IR (neat, cm-1): 3100, 3010, 2850, 2215, 1520, 1260, 1200, 1140, 1020, 850; $^1$H-NMR (400 MHz, CDCl$_3$): δ 7.82-7.80 (m, 3H), 7.64 (dd, J=0.7, 7.08 Hz, 1H), 7.51 (s, 1H), 7.29-7.24 (m, 3H), 7.18 (s, 1H), 7.07-7.05 (m, 2H), 6.82 (s, 1H), 5.15 (s, 1H), 3.978 (s, 3H), 3.62 (s, 3H); $^{13}$C-NMR (100 MHz, CDCl3): δ 149.7, 149.6, 149.0, 145.9, 143.1, 139.9, 135.6, 131.6, 130.1, 129.1 (2×CH), 128.3, 128.0 (2×CH), 127.5, 127.3, 125.6, 119.7, 119.6, 116.8, 109.1, 107.3, 103.4, 54.7, 55.4, 53.8; HRMS calcd for C$_{26}$H$_{19}$NO$_2$: 377.1416. found: 377.1417.

1-(2,3-dimethoxy-11-phenyl-11H-benzo[a]fluoren-9-yl)pentan-1-one (2r)

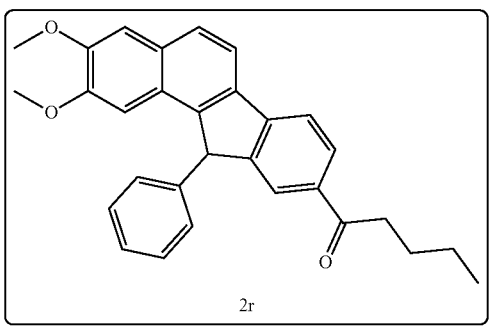 [SMILES: CCCCC(=O)c1ccc2c(c1)C(c1ccccc1)c1c-2ccc2cc(OC)c(OC)cc12]

Pale brown solid (m.p.: 166-169° C.); IR (neat, cm-1): 3040, 2850, 2215, 1690, 1530, 1240, 740; $^1$H-NMR (600 MHz, CDCl$_3$): δ 8.0 (d, J=7.9 Hz, 1H), 7.88 (s, 1H), 7.83 (t, J=8.1 Hz, 2H), 7.79 (d, J=8.3 Hz, 1H), 7.27-7.24 (m, 2H), 7.22-7.20 (m, 1H), 7.17 (s, 1H), 7.11 (d, J=7.1 Hz, 2H), 6.88 (s, 1H), 5.24 (d, J=3.5 Hz, 1H), 3.97 (s, 3H), 3.64 (s, 3H), 2.93 (t, J=7.4 Hz, 2H), 1.69 (q, J=7.4, 7.6 Hz, 2H), 1.42-1.36 (m, 2H), 0.94 (t, J=7.4 Hz, 3H); $^{13}$C-NMR (100 MHz, CDCl$_3$): δ 200.2, 149.6, 149.4, 148.8, 146.1, 143.6, 140.7, 136.3, 135.4, 129.8, 128.9 (2×CH), 128.2 (2×CH), 128.1, 127.3, 127.0, 125.8, 124.4, 119.0, 117.0, 107.3, 103.5, 55.8, 55.5, 54.1, 38.3, 26.6, 22.5, 13.9; HRMS calcd for C$_{30}$H$_{28}$O$_3$: 436.2038. found: [M+NH$_4$]$^+$=454.2377.

Tributyl(11-phenyl-11H-indeno[1,2-g]chrysen-6-yl)stannane

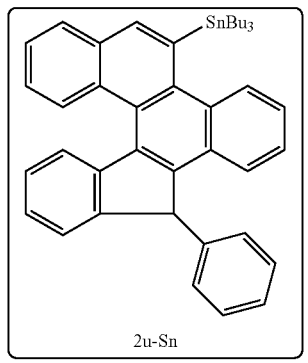

Pale White solid (m.p.: 195-200° C.); IR (neat, cm-1): 3064, 3025, 2850, 1600, 1520, 1400, 1260, 1110, 780; $^1$H-NMR (400 MHz, CDCl$_3$): δ 9.10 (d, J=8.24 Hz, 1H), 8.71 (d, J=3.76 Hz, 2H), 8.69 (d, J=3.0 Hz, 2H), 8.21 (d, J=7.72 Hz, 1H), 8.04 (d, J=8.7 Hz, 2H), 7.86 (d, J=7.16 Hz, 1H), 7.67 (t, J=7.16 Hz, 1H), 7.60 (t, J=7.44 Hz, 2H), 7.56-7.39 (m, 2H), 7.27-7.19 (m, 6H), 5.42 (s, 1H), 1.70-1.62 (m, 6H), 1.42-1.27 (m, 12H), 0.96-0.92 (m, 9H); $^{13}$C-NMR (100 MHz, CDCl$_3$): δ 149.6, 142.2, 135.6, 132.7, 130.5, 130.0, 129.6, 129.0, 128.9, 128.0, 127.6, 127.1, 126.9, 126.7, 126.6, 126.4, 126.3, 126.0, 125.9, 125.4, 124.5, 124.1, 123.9, 123.6, 121.3, 54.7, 27.8, 26.8, 17.4, 13.6 (Chemically equivalent carbons merge with other carbons); HRMS calcd for C$_{43}$H$_{46}$Sn: 682.2621. found: 682.2619.

11-phenyl-11H-indeno[1,2-g]chrysene (2u)

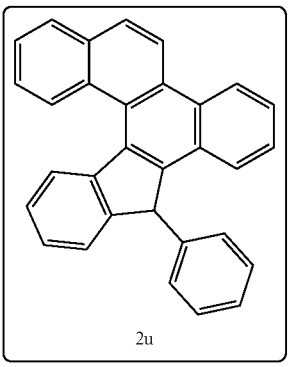 [SMILES: c1ccc(C2c3ccccc3-c3c2c2ccccc2c2ccc4ccccc4c32)cc1]

White solid (m.p.: 202-205° C.); IR (neat, cm-1): 3064, 3025, 2850, 1600, 1552, 1020, 750; $^1$H-NMR (400 MHz, CDCl$_3$): δ 9.10 (d, J=8.2 Hz, 1H), 8.70 (t, J=8.4 Hz, 2H), 8.20 (d, J=7.7 Hz, 1H), 8.04 (d, J=8.4 Hz, 2H), 7.86 (d, J=7.8 Hz, 1H), 7.66 (t, J=7.1 Hz, 1H), 7.58 (t, J=7.8 Hz, 2H), 7.56-7.39 (m, 2H), 7.30-7.20 (m, 7H), 5.41 (s, 1H); $^{13}$C-NMR (100 MHz, CDCl$_3$): δ 149.6, 142.3, 135.6, 132.7, 130.5, 130.0, 129.6, 129.3, 129.0 (3×C), 128.9, 128.0 (2×CH), 127.6, 127.1 (2×CH), 126.9, 126.7, 126.6, 126.4, 126.3, 126.0, 125.9, 125.4, 124.5, 124.1, 123.9, 123.6, 121.3, 54.7; HRMS calcd for C$_{31}$H$_{20}$: 392.1565. found: 392.1583.

11-phenyl-11H-indeno[1,2-g]naphtho[1,2-p]chrysene (2v)

Mixture of 2 Compounds

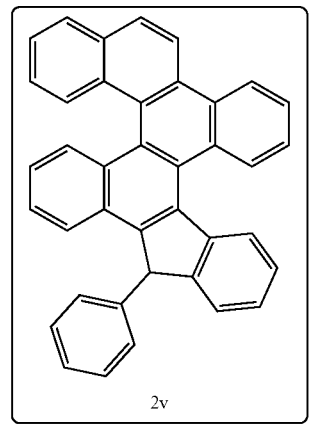 [SMILES: c1ccc(C2c3ccccc3-c3c2c2ccccc2c2c3c3ccccc3c3ccc4ccccc4c32)cc1]

Brown semisolid; IR (neat, cm-1): 3064, 3025, 2850, 1600, 1552, 1020, 750; $^1$H-NMR (400 MHz, CDCl$_3$): δ 9.10 (d, J=8.2 Hz, 1H), 8.70 (t, J=8.4 Hz, 2H), 8.20 (d, J=7.7 Hz, 1H), 8.04 (d, J=8.4 Hz, 2H), 7.86 (d, J=7.8 Hz, 1H), 7.66 (t, J=7.1 Hz, 1H), 7.58 (t, J=7.8 Hz, 2H), 7.56-7.39 (m, 2H), 7.30-7.20 (m, 7H), 5.41 (s, 1H); $^{13}$C-NMR (100 MHz, CDCl$_3$): δ 149.6, 142.3, 135.6, 132.7, 130.5, 130.0, 129.6, 129.3, 129.0 (3×C), 128.9, 128.0 (2×CH), 127.6, 127.1 (2×CH), 126.9, 126.7, 126.6, 126.4, 126.3, 126.0, 125.9, 125.4, 124.5, 124.1, 123.9, 123.6, 121.3, 54.7; MALDI calcd for C$_{39}$H$_{24}$: 492.1878. found: 492.1878.

5-fluoro-11-phenyl-11H-indeno[1,2-g]naphtho[1,2-p]chrysene (2w)

Mixture of 2 Compounds

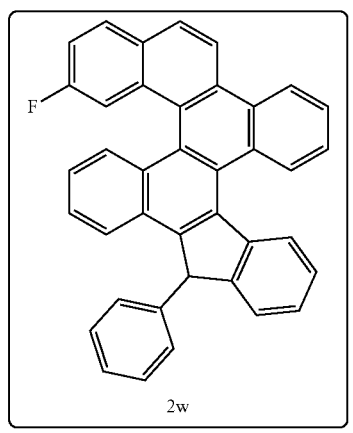 [SMILES: Fc1ccc2ccc3c4ccccc4c4c5c(c6ccccc6c4c3c2c1)C(c1ccccc1)c1ccccc1-5]

$^1$H-NMR (400 MHz, CDCl$_3$): δ 9.10 (s, 0.4H), 9.08-9.06 (m, 1H), 8.99-8.97 (m, 0.3H), 8.88 (d, J=8.4 Hz, 0.4H), 8.77-8.72 (m, 3H), 8.11-7.79 (m, 6H), 7.77-7.70 (m, 5H), 7.63-7.59 (m, 5H), 7.57-7.56 (m, 3H), 7.53-7.48 (m, 5H), 7.40-7.21 (m, 4H), 5.72 (s, 0.4H), 5.44 (s, 1H);

4,5-dimethoxy-11-phenyl-11H-indeno[1,2-g]naphtho[1,2-p]chrysene (2w)

Mixture of 2 Compounds

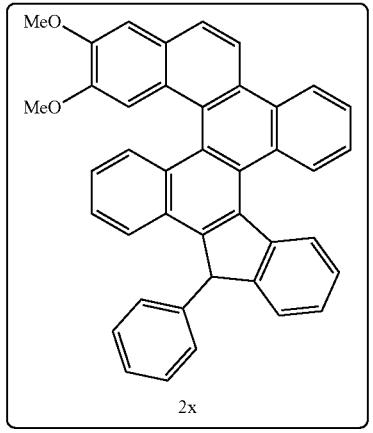 [SMILES: COc1cc2ccc3c4ccccc4c4c5c(c6ccccc6c4c3c2cc1OC)C(c1ccccc1)c1ccccc1-5]

Pale brown sticky solid; IR (neat, cm-1): 3064, 3025, 2850, 1600, 1552, 1020, 750; $^1$H-NMR (400 MHz, CDCl$_3$): (95% pure single compound) δ 9.05 (dd, J=7.3, 1 Hz, 1H), 8.76 (d, J=7.9 Hz, 1H), 8.19 (d, J=7.7 Hz, 1H), 8.02 (d, J=8.4 Hz, 1H), 7.99-7.76 (m, 2H), 7.72-7.70 (m, 1H), 7.68-7.55 (m, 1H), 7.48-7.45 (m, 1H), 7.36-7.30 (m, 4H), 7.27-7.25 (m, 2H), 7.24-7.21 (m, 4H), 7.18-7.14 (m, 1H), 5.44 (s, 1H), 4.07 (s, 3H), 3.40 (s, 3H).

MIXTURE OF (1:0.3); $^{13}$C-NMR (100 MHz, CDCl$_3$): δ 150.0, 149.7, 149.1, 149.0, 144.0, 142.3, 142.1, 142.0, 141.6, 135.2, 131.0, 130.27, 130.2, 130.1, 129.6, 129.2, 128.9, 128.7, 128.6, 128.5, 128.2, 128.1, 128.0, 128.0, 127.8, 127.3, 127.2, 127.0, 126.8, 126.7, 126.5, 126.5, 126.3, 126.1, 126.0, 125.9, 125.6, 125.4, 125.2, 125.1, 124.5, 124.3, 124.2, 124.1, 123.7, 123.6, 123.4, 119.4, 119.3, 109.9, 109.8, 106.7, 106.6, 55.8, 55.0, 54.9, 54.7, 53.9; MALDI calcd for C$_{41}$H$_{28}$O$_2$: 552.2089. found: 551.81.

Tributyl(3-methoxy-1,3-diphenylprop-1-en-2-yl)stannane

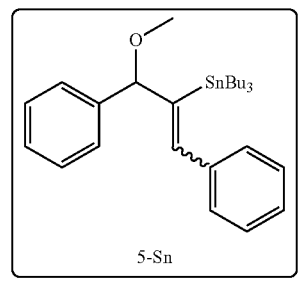

Compound 3-Sn was purified from crude mixture by using Prep-TLC. Pale yellow liquid, $^1$H-NMR (400 MHz, CDCl$_3$): 7.38-7.21 (m, 11H), 4.88 (s, 1H), 3.37 (s, 3H), 1.56-1.11 (m, 12H), 0.79 (t, J=7.0, 9 H) 0.61-0.56 (m, 6H); $^{13}$C-NMR (100 MHz, CDCl$_3$):151.1, 141.6, 141.3, 140.6, 128.1, 128.0, 127.4, 127.2, 127.0, 89.8, 56.4, 28.9, 13.6, 11.4.

2-iodo-3-(methoxyprop-1-ene-1,3-diyl)dibenzene

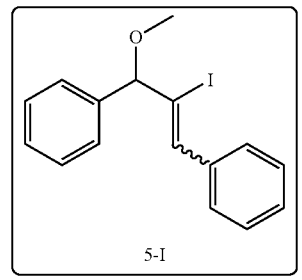 [SMILES: COC(C(I)=Cc1ccccc1)c1ccccc1]

Compound 3-I was prepared from 3-Sn using same procedure as mentioned for 6a.

Pale yellow liquid, $^1$H-NMR (400 MHz, CDCl$_3$): 7.62 (d, J=1.48, 2 H), 7.59-7.32 (m, 9H), 4.74 (s, 1H), 3.48 (s, 3H); $^{13}$C-NMR (100 MHz, CDCl$_3$): 139.4, 137.0, 135.7, 128.8, 128.2, 128.0, 127.9, 127.0, 110.3, 89.7, 56.7.

(E)-(3-methoxyprop-1-ene-1,3-diyl)dibenzene

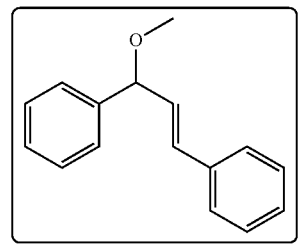 [SMILES: COC(/C=C/c1ccccc1)c1ccccc1]

Compound 3-Sn was subjected to acid hydrolysis lead to formation of (E)-(3-methoxyprop-1-ene-1,3-diyl)dibenzene. $^{1}$H NMR (400 MHz, CDCl3): δ 7.39-7.22 (m, 10H), 6.63 (d, J=15.8 Hz, 1H), 6.28 (dd, J=7.2, 15.8 Hz, 1H), 4.80 (d, J=6.92 Hz, 1H), 3.38 (s, 3H). (please see SI *Adv. Synth. Catal.* 2009, 351, 865-868. for C$^{13}$ and mass spectra)

6-iodo-11-phenyl-11H-benzo[a]fluorene (5a)

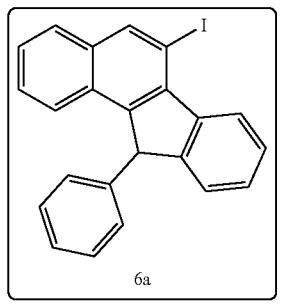 [SMILES: Ic1cc2ccccc2c2c1-c1ccccc1C2c1ccccc1]

Synthetic Procedure for Compound 6a:

Compound 2a-Sn (80.0 mg) was dissolved in 20 mL dry-DCM and Iodine (1.5 eq) was added to above mixture and stirred for 4 h at room temperature. Then the reaction mixture was quenched with saturated Na$_2$S$_2$O$_3$.5H$_2$O solution, the reaction mixture was extracted with DCM (15 mL). The extract was washed with brine solution, dried over Na$_2$SO$_4$, and concentrated under reduced pressure. The residue was eluted through a silica column to afford compound purified by column chromatography over silica gel, which yielded 6-iodo-11-phenyl-11H-benzo[a]fluorene (6a) (57.00 mg, 0.13 mmol, 80%).

Pale brown solid; IR (neat, cm-1): 3080, 3020, 2860, 1534, 1090, 800, 510; $^{1}$H-NMR (600 MHz, CDCl$_3$): δ 8.94 (d, J=7.9 Hz, 1H), 8.50 (s, 1H), 7.75 (d, J=8.1 Hz, 1H), 7.65 (d, J=8.1 Hz, 1H), 7.47-7.39 (m, 1H), 7.38-7.37 (m, 1H), 7.33-7.28 (m, 3H), 7.27-7.22 (m, 3H), 7.13-7.08 (m, 2H), 5.24 (s, 1H); $^{13}$C-NMR (100 MHz, CDCl$_3$): δ 149.4, 145.5, 141.5, 140.7, 140.2, 139.0, 134.1, 129.3, 128.9 (2×C), 127.8 (2×C), 127.5 (2×C), 126.9, 126.8, 126.3, 126.0, 124.8, 124.7, 122.2, 85.5, 53.6; HRMS calcd for C$_{23}$H$_{15}$I: 418.0218. found: 418.0226.

6-(3,5-dimethoxyphenyl)-11-phenyl-11H-benzo[a]fluorene (7a)

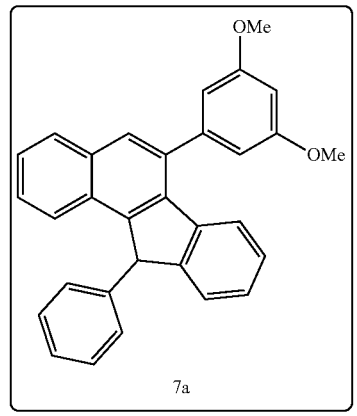 [SMILES: COc1cc(OC)cc(-c2cc3ccccc3c3c2-c2ccccc2C3c2ccccc2)c1]

Procedure for the Heck Coupling Reaction:

A flame-dried RBF with a magnetic stirring bar was charged with Pd(OAc)$_2$ (2.0 mg, 0.0086 mmol), LiCl (1 mg, 0.023 mmol), CuCl (3 mg, 0.017 mmol), aryl iodide (0.094 mmol), and N,N-dimethylacetamide (10 mL) under N$_2$. After the mixture was stirred at room temperature for 5 min, arylstanne 50 mg (0.086 mol) was added. The resulting mixture was heated at 80° C. for 12 h and then cooled to ambient temperature. The solvent was evaporated and the residue was diluted with 30 mL CH$_2$Cl$_2$, filtered through a Celite pad, and washed with CH$_2$Cl$_2$ (10-20 mL). The combined organic phases were concentrated and the resulting residue was purified by column chromatography on silica gel to provide the desired product.

Procedure for the Suzuki Coupling Reaction:

To a solution of Na$_2$CO$_3$ (75 mg, 0.717 mmol) in toluene (4.5 ml), ethanol (1.5 ml) and water (1.5 ml) was added 6-iodo-11-phenyl-11H-benzo[a]fluorene (50 mg, 0.119 mmol) at room temperature, and the solution was degassed with nitrogen. To this mixture was added (3,5-dimethoxyphenyl)boronic acid (26 mg, 0.14 mmol) and Pd(PPh$_3$)$_4$ (8 mg, 5 mol %), and the resulting mixture was heated to 100° C. for 8 h. After completion of the reaction, the solution was cooled to room temperature, washed with water, and the organic layer was separated. The aqueous layer was extracted with ethyl acetate, washed with brine solution, dried over MgSO$_4$, and concentrated. The residues were eluted through a silica column to give the desired 6-(3,5-dimethoxyphenyl)-11-phenyl-11H-benzo[a]fluorene.

Pale yellow liquid; IR (neat, cm-1): 3056, 2910, 2840, 1640, 1510, 1254, 1230, 1050, 750; $^{1}$H-NMR (400 MHz, CDCl$_3$): δ 7.89 (d, J=8.1 Hz, 1H), 7.81 (s, 1H), 7.74 (d, J=8.3 Hz, 1H), 7.42 (t, J=7.2 Hz, 1H), 7.35-7.23 (m, 5H), 7.21-7.14 (m, 3H), 7.12-7.10 (m, 2H), 6.83 (s, 1H), 6.75 (s, 1H), 6.66 (t, J=2.2 Hz, 1H), 5.40 (s, 1H), 3.89 (s, 3H), 3.86 (s, 3H); $^{13}$C-NMR (100 MHz, CDCl$_3$): δ 160.7 (2×C), 149.4, 143.5, 143.0, 141.9, 140.6, 137.0, 136.0, 132.7, 129.5, 129.3, 128.9 (2×CH), 128.6, 128.0, 126.8, 126.6, 126.3 (2×CH), 125.7 (2×CH), 124.7, 124.6, 123.0, 107.4 (2×C), 100.1, 55.4, 53.8 (2×C); HRMS calcd for C$_{31}$H$_{24}$O$_2$: 428.1776. found: 428.1779.

3,3'-dimethoxy-11,11'-diphenyl-11H,11'H-4,4'-bibenzo[a]fluorene (8)

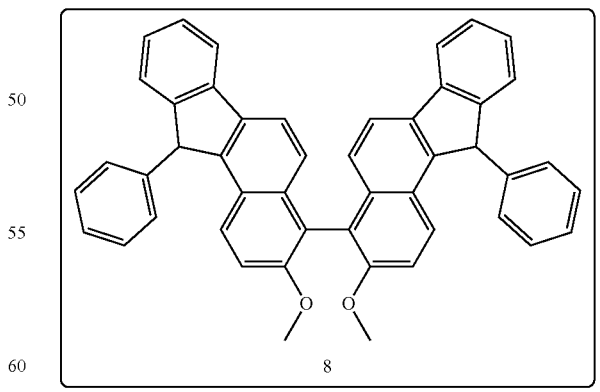

Beige solid (m.p.: 175-178° C.); IR (neat, cm-1): 3024, 2923, 1454, 1260, 1070, 733; $^{1}$H-NMR (400 MHz, CDCl$_3$): δ 7.86 (d, J=8 Hz, 1H), 7.7 (d, J=8 Hz, 1H), 7.67 (d, J=12 Hz, 1H), 7.35-7.29 (m, 5H), 7.25-7.17 (m, 5H), 5.41 (s, 1H), 3.73 (s, 3H); $^{13}$C-NMR (150 MHz, CDCl$_3$): δ 154.6, 148.9, 142.9, 142.1, 141.2, 137.2, 134.2, 128.9 (2×CH), 128.3 (2×CH), 127.1, 126.8, 126.5, 126.2 (2×CH), 126.0, 124.5, 120.9, 119.3, 119.0, 114.5, 56.7, 54.3, 29.7 (grease); MALDI calcd for $C_{48}H_{34}O_2$: 642.79. found: 642.04.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above compositions and processes without departing from the scope of the invention, it is intended that all matter contained in the above description and shown in the accompanying drawings shall be interpreted as illustrative and not in a limiting sense.

What is claimed is:

1. A method of preparing a polycyclic aromatic compound, the method comprising:
   contacting a compound having structure (I) with a stannane compound in the presence of a radical initiator to thereby prepare the polycyclic aromatic compound;
   wherein the polycyclic aromatic compound has a structure (1-a) as follows:

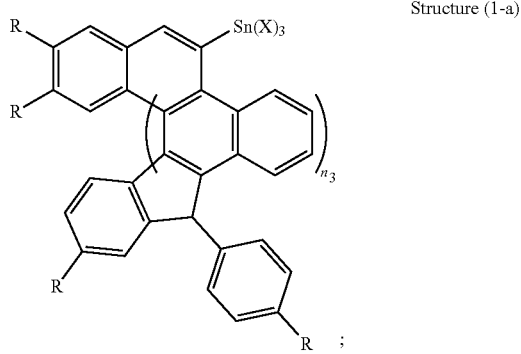

Structure (1-a)

wherein the compound having structure (I) is as follows:

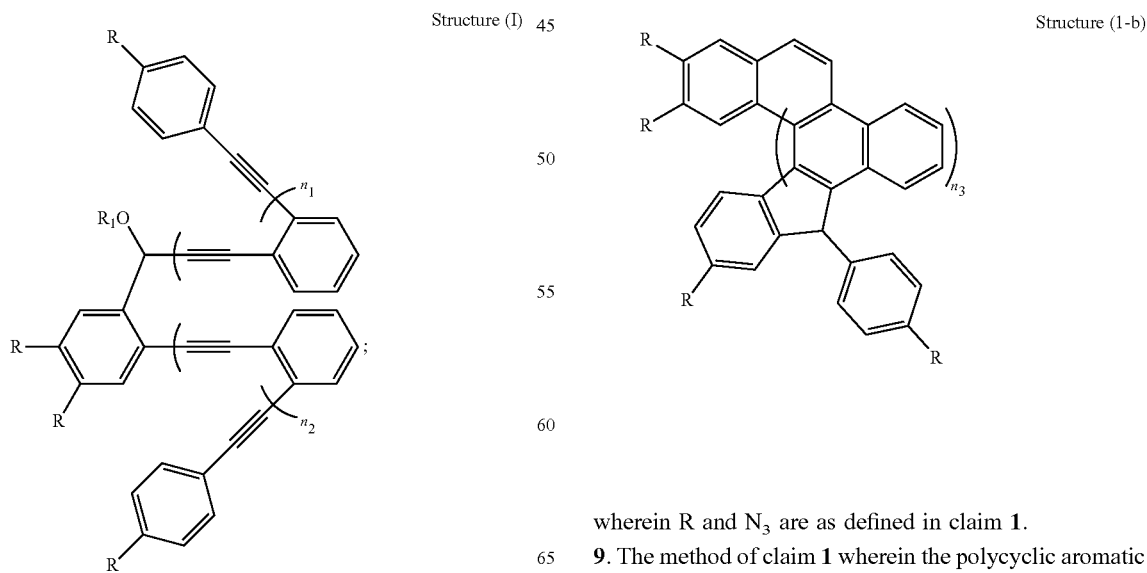

and further wherein:
   each R is independently selected from the group consisting of hydrogen, halogen, cyano, $C_1$-$C_6$ alkyl, and $C_1$-$C_6$ alkoxy;
   $R_1$ is selected from the group consisting of $C_1$-$C_6$ alkyl, —$CH_2OCH_3$, and —$CH_2CH_2OCH_3$;
   X is a $C_1$-$C_6$ alkyl or phenyl;
   $n_1$ and $n_2$ each independently have a value between 0 and 50, and further wherein either $n_1$ and $n_2$ have the same value or $n_1=n_2+1$; and
   $n_3$ has a value of $n_1+n_2$.

2. The method of claim 1 wherein the stannane compound is selected from the group consisting of trimethyl stannane, triethyl stannane, tri(n-propyl)stannane, tri(isopropyl)stannane, tri(n-butyl)stannane, tri(isobutyl)stannane, triphenyl stannane, and any combination there.

3. The method of claim 1 wherein the stannane compound is tri(n-butyl)stannane.

4. The method of claim 1 wherein the radical initiator is selected from the group consisting of an azo compound, an inorganic peroxide, an organic peroxide, and any combination thereof.

5. The method of claim 1 wherein $R_1$ is methyl.

6. The method of claim 1 wherein $n_1$ and $n_2$ each independently have a value between 0 and 25, and further wherein $n_1$ and $n_2$ have the same value.

7. The method of claim 1 wherein $n_1$ and $n_2$ each independently have a value between 0 and 25, and further wherein $n_1=n_2+1$.

8. The method of claim 1 further comprising contacting the polycyclic aromatic compound having structure (1-a) with an acid to thereby prepare a polycyclic aromatic compound having structure (1-b):

Structure (1-b)

wherein R and $N_3$ are as defined in claim 1.

9. The method of claim 1 wherein the polycyclic aromatic compound having structure (1-a) has the following structure (1-c):

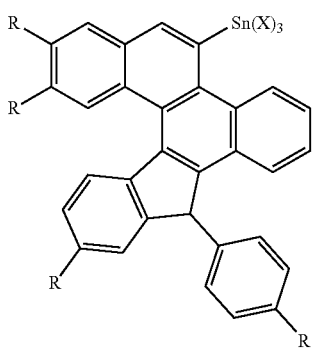

Structure (1-c)

wherein R and X are as defined in claim 1.

10. The method of claim 9 further comprising contacting the polycyclic aromatic compound having structure (1-c) with an acid to thereby prepare a polycyclic aromatic compound having structure (1-d):

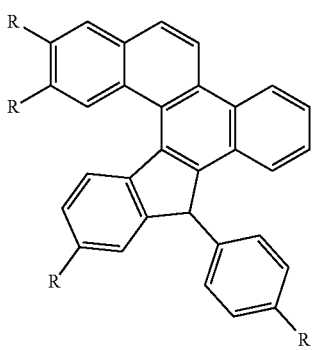

Structure (1-d)

wherein R is as defined in claim 1.

11. The method of claim 1 wherein the polycyclic aromatic compound having structure (1-a) has the following structure (1-e):

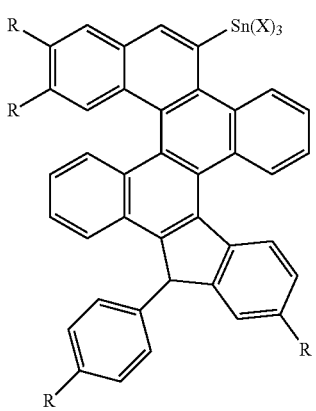

Structure (1-e)

wherein R and X are as defined in claim 1.

12. The method of claim 11 further comprising contacting the polycyclic aromatic compound having structure (1-e) with an acid to thereby prepare a polycyclic aromatic compound having structure (1-f):

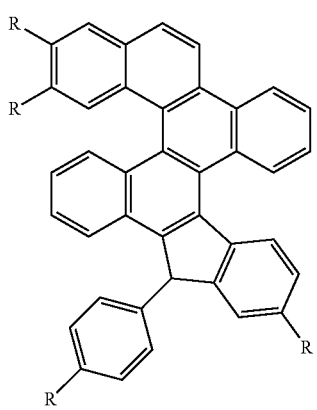

Structure (1-f)

wherein R is as defined in claim 1.

13. A method of preparing a polycyclic aromatic compound, the method comprising:

contacting a compound having structure (II) with a stannane compound in the presence of a radical initiator to thereby prepare the polycyclic aromatic compound;

wherein the polycyclic aromatic compound has a structure (1-g) as follows:

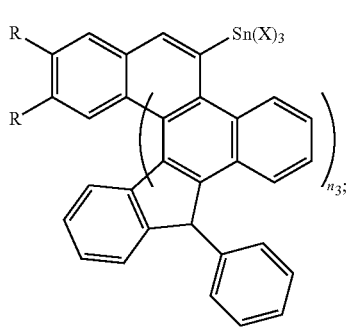

Structure (1-g)

wherein the compound having structure (II) is as follows:

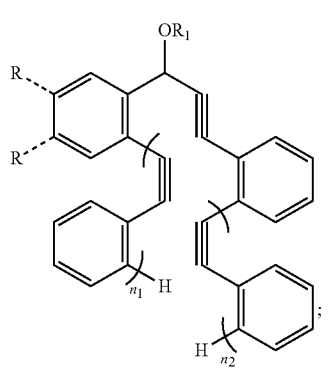

Structure (II)

and further wherein:

each R is independently selected from the group consisting of hydrogen, halogen, cyano, $C_1$-$C_6$ alkyl, and $C_1$-$C_6$ alkoxy;

$R_1$ is selected from the group consisting of $C_1$-$C_6$ alkyl, —$CH_2OCH_3$, and —$CH_2CH_2OCH_3$;

X is a $C_1$-$C_6$ alkyl or phenyl;

$n_1$ and $n_2$ each independently have a value between 0 and 50, and further wherein either $n_1$ and $n_2$ have the same value or $n_1=n_2+1$; and $n_3$ has a value of $n_1+n_2$.

14. The method of claim 13 wherein the stannane compound is selected from the group consisting of trimethyl stannane, triethyl stannane, tri(n-propyl)stannane, tri(isopropyl)stannane, tri(n-butyl)stannane, tri(isobutyl)stannane, triphenyl stannane, and any combination there.

15. The method of claim 13 wherein the stannane compound is tri(n-butyl)stannane.

16. The method of claim 13 wherein the radical initiator is selected from the group consisting of an azo compound, an inorganic peroxide, an organic peroxide, and any combination thereof.

17. The method of claim 13 further comprising contacting the polycyclic aromatic compound having structure (1-g) with an acid to thereby prepare a polycyclic aromatic compound having structure (1-h):

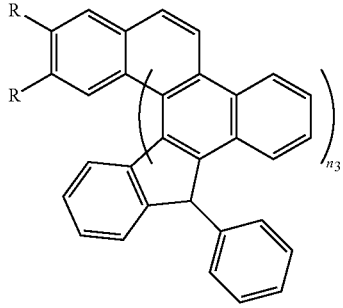

Structure (1-h)

wherein R and $N_3$ are as defined in claim 1.

18. A method of preparing a polycyclic aromatic compound, the method comprising:
contacting a compound having structure (III) with a stannane compound in the presence of a radical initiator to thereby prepare the polycyclic aromatic compound;
wherein the polycyclic aromatic compound has a structure (2-a) as follows:

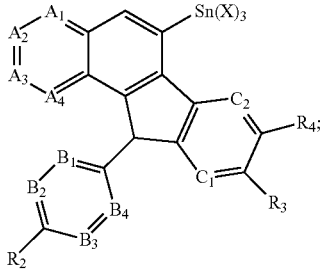

Structure (2-a)

wherein the compound having structure (III) is as follows:

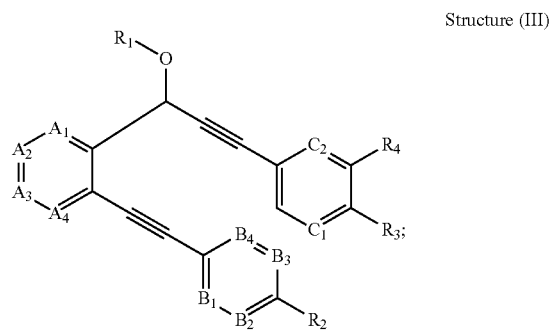

Structure (III)

and further wherein:

$A_1$, $A_2$, $A_3$, and $A_4$ are either C—R or N, wherein at least two of $A_1$, $A_2$, $A_3$, and $A_4$ are C—R, and each R is independently selected from the group consisting of hydrogen, halogen, $C_1$-$C_6$ alkyl, and $C_1$-$C_6$ alkoxy;

$B_1$, $B_2$, $B_3$, and $B_4$ are either C—R or N, wherein at least two of $B_1$, $B_2$, $B_3$, and $B_4$ are C—R, and each R is independently selected from the group consisting of hydrogen, halogen, $C_1$-$C_6$ alkyl, and $C_1$-$C_6$ alkoxy;

$C_1$ and $C_2$ are either C—R or N, and each R is independently selected from the group consisting of hydrogen, halogen, $C_1$-$C_6$ alkyl, and $C_1$-$C_6$ alkoxy;

$R_1$ is selected from the group consisting of $C_1$-$C_6$ alkyl, —$CH_2OCH_3$, and —$CH_2CH_2OCH_3$;

$R_2$, $R_3$, and $R_4$ are each independently selected from the group consisting of hydrogen, halogen, cyano, nitro, $C_1$-$C_6$-alkyl, $C_1$-$C_6$ alkoxy, hydroxy-$C_1$-$C_6$-alkyl, halo-$C_1$-$C_6$-alkyl, cyano-$C_1$-$C_6$-alkyl, $C_1$-$C_6$-alkoxy-$C_1$-$C_6$-alkyl, $C_1$-$C_6$-alkylcarbonyl, $C_1$-$C_6$-alkoxycarbonyl, $C_1$-$C_6$-alkoxycarbonyl-$C_1$-$C_6$-alkyl, $C_3$-$C_6$-cycloalkyl, $C_3$-$C_6$-cycloalkyl-$C_1$-$C_6$-alkyl, $C_5$-$C_{10}$-cycloalkenyl, aryl, aryl-$C_1$-$C_6$-alkyl, 4- to 10-membered ring heterocyclyl, 4- to 10-membered ring heterocyclyl-$C_1$-$C_6$-alkyl, 5- to 10-membered ring heteroaryl, 5- to 10-membered ring heteroaryl-$C_1$-$C_6$-alkyl, —$OR^{104}$, —$C(O)OR^{105}$, —$N(R^{106})C(O)R^{107}$, —$N(R^{108})C(O)NR^{109}R^{110}$, —$S(O)_2R^{111}$, —$S(O)_2NR^{112}R^{113}$, and —$NS(O)_2NR^{112}R^{113}$;

wherein $R^{104}$, $R^{105}$, $R^{106}$, $R^{107}$, $R^{107}$, $R^{109}$, $R^{110}$, $R^{111}$, $R^{112}$, and $R^{113}$ are independently selected from the group consisting of hydrogen, $C_1$-$C_8$-alkyl, $C_1$-$C_8$-alkoxy, halo-$C_1$-$C_8$-alkyl, cyano-$C_1$-$C_8$-alkyl, $C_3$-$C_6$-cycloalkyl, halo-$C_3$-$C_6$-cycloalkyl, 4- to 10-membered ring heterocyclyl, 4- to 10-membered ring heterocyclyl-$C_1$-$C_8$-alkyl, aryl, haloaryl, and $C_1$-$C_8$-alkylaryl; and X is a $C_1$-$C_6$ alkyl or phenyl.

19. The method of claim 18 wherein the stannane compound is selected from the group consisting of trimethyl stannane, triethyl stannane, tri(n-propyl)stannane, tri(isopropyl)stannane, tri(n-butyl)stannane, tri(isobutyl)stannane, triphenyl stannane, and any combination there.

20. The method of claim 18 wherein the stannane compound is tri(n-butyl)stannane.

21. The method of claim 18 wherein the radical initiator is selected from the group consisting of an azo compound, an inorganic peroxide, an organic peroxide, and any combination thereof.

22. The method of claim 18 wherein the compound having structure (III) has the following structure (IV):

Structure (IV)

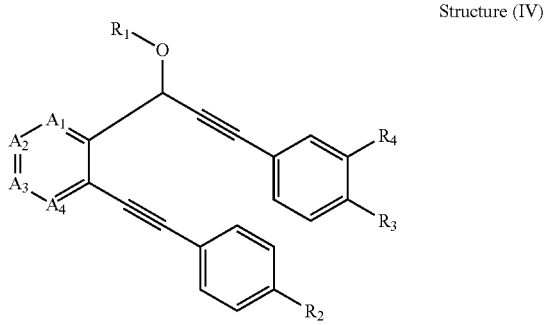

wherein $R_1$, $R_2$, $R_3$, $R_4$, $A_1$, $A_2$, $A_3$, and $A_4$ are as defined in claim 18.

23. The method of claim 18 wherein $R_1$ is methyl.
24. The method of claim 18 wherein $A_1$, $A_2$, $A_3$, and $A_4$ are each C—H.
25. The method of claim 18 wherein $A_1$, $A_2$, $A_3$ are each C—H and $D_1$ is N.
26. The method of claim 18 wherein $R_2$, $R_3$, and $R_4$ are each independently selected from the group consisting of hydrogen, methoxy, trifluoromethyl, cyano, fluoro, and n-butyl carbonyl.
27. The method of claim 18 wherein $R_2$, $R_3$, and $R_4$ are each hydrogen.
28. The method of claim 18 wherein $R_2$ is hydrogen, and $R_3$, and $R_4$ together with the phenyl ring to which they are bonded form a naphthalene ring.
29. The method of claim 18 further comprising contacting the polycyclic aromatic compound having structure (2-a) with an acid to thereby prepare a polycyclic aromatic compound having structure (2-b):

Structure (2-b)

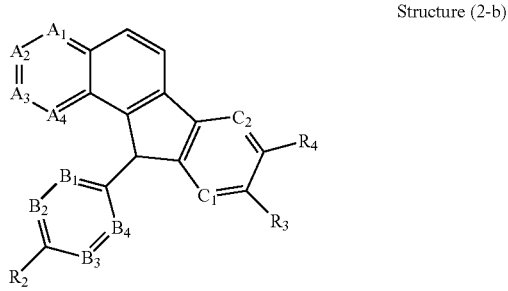

wherein $R_1$, $R_2$, $R_3$, $R_4$, $A_1$, $A_2$, $A_3$, and $A_4$ are as defined in claim 18.

30. The method of claim 18 wherein the polycyclic aromatic compound having structure (2-a) has the following structure (2-c):

Structure (2-c)

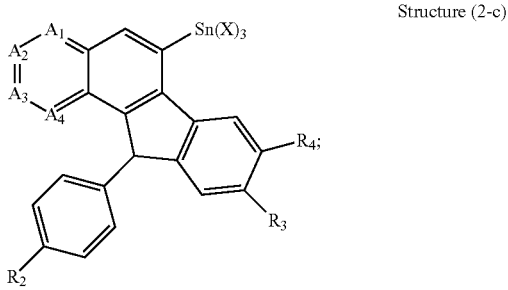

wherein X, $R_1$, $R_2$, $R_3$, $R_4$, $A_1$, $A_2$, $A_3$, and $A_4$ are as defined in claim 18.

31. The method of claim 30 further comprising contacting the polycyclic aromatic compound having structure (2-c) with an acid to thereby prepare a polycyclic aromatic compound having structure (2-d):

Structure (2-d)

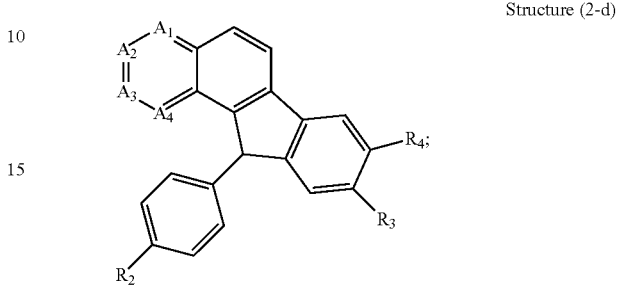

wherein $R_1$, $R_2$, $R_3$, $R_4$, $A_1$, $A_2$, $A_3$, and $A_4$ are as defined in claim 18.

32. The method of claim 18 wherein the polycyclic aromatic compound having structure (2-a) is selected from the group consisting of 11-H-phenyl-11H-benzo[a]fluorene, 11-H-phenyl-11H-indeno[1,2-h]quinoline, 11-H-phenyl-11H-indeno[1,2-h]isoquinoline, 11-H-phenyl-11H-indeno[2,1-f]isoquinoline, and 11-H-phenyl-11H-indeno[2,1-h]quinolone, each of which is substituted or unsubstituted.

33. The method of claim 18 further comprising contacting the polycyclic aromatic compound having structure (2-a) with iodine to thereby prepare a polycyclic aromatic compound having structure (2-e):

Structure (2-e)

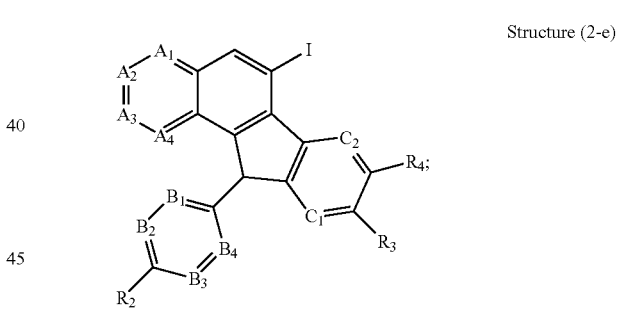

wherein $R_1$, $R_2$, $R_3$, $R_4$, $A_1$, $A_2$, $A_3$, $A_4$, $B_1$, $B_2$, $B_3$, $B_4$, $C_1$, and $C_2$ are as defined in claim 18.

34. A method of preparing a 11-phenyl-11H-benzo[a]fluorene, the method comprising:
    contacting a 1-(2-ethynylphenyl)propargyl alkyl ether with a stannane compound in the presence of a radical initiator, wherein said contact of the 1-(2-ethynylphenyl)propargyl alkyl ether with the stannane compound initiates a cascade reaction that yields a stannyl-11-phenyl-11H-benzo[a]fluorene; and
    contacting the stannyl-11-phenyl-11H-benzo[a]fluorene with an acid to thereby prepare the 11-phenyl-11H-benzo[a]fluorene, wherein the 11-phenyl-11H-benzo[a]fluorene is substituted or unsubstituted.

35. The method of claim 34 wherein the stannane compound is selected from the group consisting of trimethyl stannane, triethyl stannane, tri(n-propyl)stannane, tri(isopropyl)stannane, tri(n-butyl)stannane, tri(isobutyl)stannane, triphenyl stannane, and any combination there.

36. The method of claim 34 wherein the stannane compound is tri(n-butyl)stannane.

37. The method of claim 34 wherein the radical initiator is selected from the group consisting of an azo compound, an inorganic peroxide, an organic peroxide, and any combination thereof.

38. The method of claim 34 wherein the 1-(2-ethynylphenyl)propargyl alkyl ether has the following general structure (V):

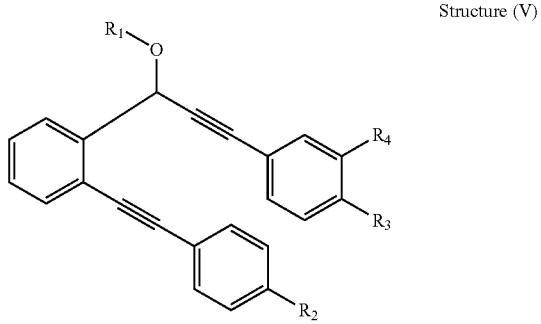

Structure (V)

wherein:
$R_1$ is selected from the group consisting of $C_1$-$C_6$ alkyl, —$CH_2OCH_3$, and —$CH_2CH_2OCH_3$;
$R_2$, $R_3$, and $R_4$ are each independently selected from the group consisting of hydrogen, halogen, cyano, nitro, $C_1$-$C_6$-alkyl, $C_1$-$C_6$ alkoxy, hydroxy-$C_1$-$C_6$-alkyl, halo-$C_1$-$C_6$-alkyl, cyano-$C_1$-$C_6$-alkyl, $C_1$-$C_6$-alkoxy-$C_1$-$C_6$-alkyl, $C_1$-$C_6$-alkylcarbonyl, $C_1$-$C_6$-alkoxycarbonyl, $C_1$-$C_6$-alkoxycarbonyl-$C_1$-$C_6$-alkyl, $C_3$-$C_6$-cycloalkyl, $C_3$-$C_6$-cycloalkyl-$C_1$-$C_6$-alkyl, $C_5$-$C_{10}$-cycloalkenyl, aryl, aryl-$C_1$-$C_6$-alkyl, 4- to 10-membered ring heterocyclyl, 4- to 10-membered ring heterocyclyl-$C_1$-$C_6$-alkyl, 5- to 10-membered ring heteroaryl, 5- to 10-membered ring heteroaryl-$C_1$-$C_6$-alkyl, —$OR^{104}$, —$C(O)OR^{105}$, —$N(R^{106})C(O)R^{107}$, —$N(R^{108})C(O)NR^{109}R^{110}$, —$S(O)_2R^{111}$, —$S(O)_2NR^{112}R^{113}$, and —$NS(O)_2NR^{112}R^{113}$;
wherein $R^{104}$, $R^{105}$, $R^{106}$, $R^{107}$, $R^{107}$, $R^{109}$, $R^{110}$, $R^{111}$, $R^{112}$, and $R^{113}$ are independently selected from the group consisting of hydrogen, $C_1$-$C_8$-alkyl, $C_1$-$C_8$-alkoxy, halo-$C_1$-$C_8$-alkyl, cyano-$C_1$-$C_8$-alkyl, $C_3$-$C_6$-cycloalkyl, halo-$C_3$-$C_6$-cycloalkyl, 4- to 10-membered ring heterocyclyl, 4- to 10-membered ring heterocyclyl-$C_1$-$C_8$-alkyl, aryl, haloaryl, and $C_1$-$C_8$-alkylaryl.

39. The method of claim 38 wherein $R_1$ is methyl.

40. The method of claim 38 wherein $R_2$, $R_3$, and $R_4$ are each independently selected from the group consisting of hydrogen, methoxy, trifluoromethyl, cyano, fluoro, and n-butyl carbonyl.

41. The method of claim 38 wherein $R_2$, $R_3$, and $R_4$ are each hydrogen.

42. The method of claim 38 wherein $R_2$ is hydrogen, and $R_3$ and $R_4$ together with the phenyl ring to which they are bonded form a naphthalene ring.

43. The method of claim 38 wherein the stannyl-11-phenyl-11H-benzo[a]fluorene has the following structure (3-a):

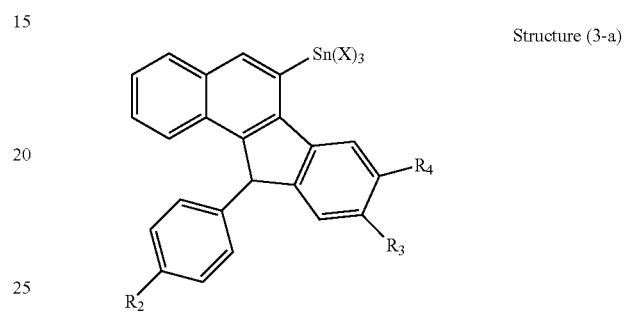

Structure (3-a)

wherein $R_2$, $R_3$, and $R_4$ are as defined in claim 38; and X is a $C_1$-$C_6$ alkyl or phenyl.

44. The method of claim 43 wherein the stannyl-11-phenyl-11H-benzo[a]fluorene having the structure (3-a) is contacted with the acid to thereby prepare a 11-phenyl-11H-benzo[a]fluorene having structure (3-b):

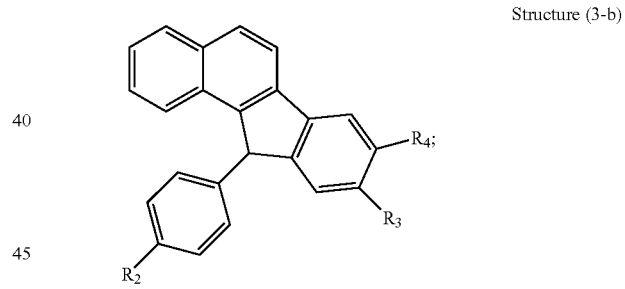

Structure (3-b)

wherein $R_2$, $R_3$, and $R_4$ are as defined in claim 38.

* * * * *